(12) United States Patent
Han

(10) Patent No.: US 12,025,589 B2
(45) Date of Patent: Jul. 2, 2024

(54) INDENTATION METHOD TO MEASURE MULTIPLE ROCK PROPERTIES

(71) Applicant: Saudi Arabian Oil Company, Dhahran (SA)

(72) Inventor: Yanhui Han, Houston, TX (US)

(73) Assignee: Saudi Arabian Oil Company, Dhahran (SA)

( * ) Notice: Subject to any disclaimer, the term of this patent is extended or adjusted under 35 U.S.C. 154(b) by 205 days.

(21) Appl. No.: 17/543,348

(22) Filed: Dec. 6, 2021

(65) Prior Publication Data
US 2023/0175937 A1   Jun. 8, 2023

(51) Int. Cl.
| | |
|---|---|
| *G01N 3/08* | (2006.01) |
| *G01N 3/02* | (2006.01) |
| *G01N 3/42* | (2006.01) |
| *G01N 33/24* | (2006.01) |

(52) U.S. Cl.
CPC .............. *G01N 3/08* (2013.01); *G01N 3/02* (2013.01); *G01N 33/24* (2013.01); *G01N 2203/0019* (2013.01); *G01N 2203/04* (2013.01)

(58) Field of Classification Search
CPC .. G01N 3/08; G01N 3/42; G01N 3/46; G01N 33/24; G01N 1/28; G01N 21/84; G01N 3/00; G01N 3/44; G01N 23/20025; G01N 3/24; G01N 3/40; G01N 3/20; G01N 3/18; G01N 3/32; G01N 3/02; G01N 29/07; G01N 2291/0232; G01N 2291/0421; G01N 2291/0422; G06F 30/13; E21B 49/006
See application file for complete search history.

(56) References Cited

U.S. PATENT DOCUMENTS

| | | | |
|---|---|---|---|
| 701,154 A | 5/1902 | Cole | |
| 830,437 A | 9/1906 | Humphrey | |
| 2,649,710 A | 8/1953 | Dale | |
| 2,706,406 A | 4/1955 | Vincent et al. | |
| 2,788,373 A | 4/1957 | Mills et al. | |
| 2,801,698 A | 8/1957 | Bond | |

(Continued)

FOREIGN PATENT DOCUMENTS

| | | |
|---|---|---|
| AU | 2014278762 | 9/2015 |
| CA | 2322118 | 12/2007 |

(Continued)

OTHER PUBLICATIONS

U.S. Appl. No. 15/243,312, Chen, filed Aug. 22, 2016.
(Continued)

*Primary Examiner* — Brandi N Hopkins
(74) *Attorney, Agent, or Firm* — Fish & Richardson P.C.

(57) ABSTRACT

A method for measuring multiple rock properties using a multi-stage indentation test is provided. The method includes measuring load and displacement versus time on an indentation measurement unit, while preforming the multi-stage indentation test. The multi-stage indentation test includes indenting a saturated specimen to full load to generate a line segment 1, releasing the load on the saturated specimen to generate a line segment 2, indenting the saturated specimen to full load to generate a line segment 3, holding the loading until the displacement curve levels off to generate a line segment 4, and reducing the loading to zero to generate a line segment 5.

14 Claims, 5 Drawing Sheets

(56) References Cited

U.S. PATENT DOCUMENTS

| | | |
|---|---|---|
| 2,900,269 A | 8/1959 | Bauman et al. |
| 2,904,445 A | 9/1959 | Sellers |
| 3,066,739 A | 12/1962 | Saurenman et al. |
| 3,176,511 A | 4/1965 | Widmyer |
| 3,284,281 A | 11/1966 | Thomas |
| 3,316,965 A | 5/1967 | Watanabe |
| 3,402,770 A | 9/1968 | Messenger |
| 3,456,183 A | 7/1969 | Codrington et al. |
| 3,601,197 A | 8/1971 | Ayers et al. |
| 3,616,855 A | 11/1971 | Colgate |
| 3,690,622 A | 9/1972 | Brunner et al. |
| 3,716,387 A | 2/1973 | Simmons et al. |
| 3,789,217 A | 1/1974 | Youmans |
| 3,807,557 A | 4/1974 | Miller |
| 3,834,122 A | 9/1974 | Allison et al. |
| 3,875,606 A | 4/1975 | Landers |
| 3,912,330 A | 10/1975 | Carnahan et al. |
| 3,926,575 A | 12/1975 | Meyers |
| 3,937,283 A | 2/1976 | Blauer et al. |
| 3,938,594 A | 2/1976 | Rhudy et al. |
| 3,977,472 A | 8/1976 | Graham et al. |
| 3,980,136 A | 9/1976 | Plummer et al. |
| 3,996,062 A | 12/1976 | Frost |
| 4,043,599 A | 8/1977 | Lingane |
| 4,043,885 A | 8/1977 | Yen et al. |
| 4,044,833 A | 8/1977 | Volz |
| 4,047,988 A | 9/1977 | Weill |
| 4,135,579 A | 1/1979 | Rowland et al. |
| 4,137,182 A | 1/1979 | Golinkin |
| 4,193,451 A | 3/1980 | Dauphine |
| 4,195,010 A | 3/1980 | Russell et al. |
| 4,216,829 A | 8/1980 | Murphy |
| 4,220,550 A | 9/1980 | Frenier et al. |
| 4,223,726 A | 9/1980 | Cha |
| 4,252,189 A | 2/1981 | Bodine |
| RE30,738 E | 9/1981 | Bridges et al. |
| 4,289,639 A | 9/1981 | Buske |
| 4,324,560 A | 4/1982 | Fonseca |
| 4,345,650 A | 8/1982 | Wesley |
| 4,381,950 A | 5/1983 | Lawson |
| 4,389,461 A | 6/1983 | Scott |
| 4,389,878 A | 6/1983 | Manzie, Jr. |
| 4,444,058 A | 4/1984 | Ratigan |
| 4,452,076 A | 6/1984 | Gavignet et al. |
| 4,480,696 A | 11/1984 | Almond et al. |
| 4,485,071 A | 11/1984 | Larter |
| 4,485,869 A | 12/1984 | Sresty |
| 4,493,875 A | 1/1985 | Beck et al. |
| 4,519,455 A | 5/1985 | Holtmyer |
| 4,554,082 A | 11/1985 | Holtmyer |
| 4,587,739 A | 5/1986 | Holcomb |
| 4,594,170 A | 6/1986 | Brown et al. |
| 4,627,495 A | 12/1986 | Harris |
| 4,629,702 A | 12/1986 | Fan et al. |
| 4,640,692 A | 2/1987 | Audeh |
| 4,665,982 A | 5/1987 | Brown |
| 4,665,990 A | 5/1987 | Perlman |
| 4,681,914 A | 7/1987 | Olson et al. |
| 4,708,805 A | 11/1987 | D'Muhala |
| 4,718,489 A | 1/1988 | Hallam et al. |
| 4,725,372 A | 2/1988 | Teot et al. |
| 4,735,731 A | 4/1988 | Rose et al. |
| 4,745,139 A | 5/1988 | Haasl et al. |
| 4,749,038 A | 6/1988 | Shelley et al. |
| 4,780,223 A | 10/1988 | Baranet et al. |
| 4,800,752 A | 1/1989 | Piers |
| 4,830,773 A | 5/1989 | Olson |
| 4,830,779 A | 5/1989 | Maeno et al. |
| 4,836,284 A | 6/1989 | Tinker |
| 4,846,277 A | 7/1989 | Khalil et al. |
| 4,864,472 A | 9/1989 | Yoshimura |
| 4,882,128 A | 11/1989 | Hukvari et al. |
| 4,887,670 A | 12/1989 | Lord et al. |
| 5,007,481 A | 4/1991 | Williams et al. |
| 5,023,551 A | 6/1991 | Kleinberg et al. |
| 5,031,700 A | 7/1991 | McDougall et al. |
| 5,069,283 A | 12/1991 | Mack |
| 5,082,056 A | 1/1992 | Tackett, Jr. |
| 5,180,556 A | 1/1993 | Nolte et al. |
| 5,193,396 A | 3/1993 | Gorski |
| 5,199,490 A | 4/1993 | Surles et al. |
| 5,203,413 A | 4/1993 | Zerhbouh |
| 5,213,705 A | 5/1993 | Olson |
| 5,224,543 A | 7/1993 | Watkins |
| 5,232,490 A | 8/1993 | Bender et al. |
| 5,251,286 A | 10/1993 | Wiener et al. |
| 5,256,315 A | 10/1993 | Lockhart |
| 5,271,465 A | 12/1993 | Schmidt et al. |
| 5,293,905 A | 3/1994 | Friedrich |
| 5,302,297 A | 4/1994 | Barthrope |
| 5,384,064 A | 1/1995 | Peterson |
| 5,387,865 A | 2/1995 | Jerosch-Herold et al. |
| 5,390,529 A | 2/1995 | Ghiselli |
| 5,435,187 A | 7/1995 | Ewy |
| 5,478,802 A | 12/1995 | Moradi-Araghi |
| 5,486,762 A | 1/1996 | Freedman et al. |
| 5,529,123 A | 6/1996 | Carpenter et al. |
| 5,551,516 A | 9/1996 | Norman et al. |
| 5,586,027 A | 12/1996 | Carlson et al. |
| 5,604,184 A | 2/1997 | Ellis et al. |
| 5,613,555 A | 3/1997 | Sorem et al. |
| 5,661,237 A | 8/1997 | Dussan et al. |
| 5,757,473 A | 5/1998 | Kanduth et al. |
| 5,759,964 A | 6/1998 | Shuchart |
| 5,831,177 A | 11/1998 | Waid et al. |
| 5,869,750 A | 2/1999 | Onan |
| 5,912,219 A | 6/1999 | Carrie et al. |
| 5,944,104 A | 8/1999 | Riese |
| 5,964,295 A | 10/1999 | Brown et al. |
| 5,967,233 A | 10/1999 | Riese |
| 5,999,887 A | 12/1999 | Giannakopoulos et al. |
| 6,012,520 A | 1/2000 | Yu et al. |
| 6,035,936 A | 3/2000 | Whalen |
| 6,076,046 A | 6/2000 | Vassudevan |
| 6,095,679 A | 8/2000 | Hammiche et al. |
| 6,119,777 A | 9/2000 | Runia |
| 6,121,336 A | 9/2000 | Okoroafor et al. |
| 6,131,661 A | 10/2000 | Conner et al. |
| 6,138,760 A | 10/2000 | Lopez et al. |
| 6,140,816 A | 10/2000 | Heron et al. |
| 6,143,698 A | 11/2000 | Murphey et al. |
| 6,165,295 A | 12/2000 | Wagaman |
| 6,176,315 B1 | 1/2001 | Reddy et al. |
| 6,193,396 B1 | 2/2001 | Gorski |
| 6,207,620 B1 | 3/2001 | Gonzalez et al. |
| 6,227,295 B1 | 5/2001 | Mitchell et al. |
| 6,258,859 B1 | 7/2001 | Dahayanake et al. |
| 6,263,729 B1 | 7/2001 | Catala |
| 6,283,214 B1 | 9/2001 | Guinot |
| 6,306,800 B1 | 10/2001 | Samuel et al. |
| 6,349,595 B1 | 2/2002 | Lorenzo et al. |
| 6,399,546 B1 | 6/2002 | Chang et al. |
| 6,410,489 B1 | 6/2002 | Zhang et al. |
| 6,411,902 B1 | 6/2002 | Wiltshire |
| 6,435,277 B1 | 8/2002 | Qu et al. |
| 6,468,945 B1 | 10/2002 | Zhang |
| 6,478,971 B1 | 11/2002 | Koefod et al. |
| 6,482,866 B1 | 11/2002 | Dahayanake et al. |
| 6,488,091 B1 | 12/2002 | Weaver |
| 6,491,099 B1 | 12/2002 | Di Lullo Arias et al. |
| 6,491,425 B1 | 12/2002 | Hammiche et al. |
| 6,494,263 B2 | 12/2002 | Todd |
| 6,516,080 B1 | 2/2003 | Nur |
| 6,579,572 B2 | 6/2003 | Espin et al. |
| 6,605,570 B2 | 8/2003 | Miller et al. |
| 6,609,067 B2 | 8/2003 | Tare et al. |
| 6,613,720 B2 | 9/2003 | Feraud et al. |
| 6,640,898 B2 | 11/2003 | Lord et al. |
| 6,652,682 B1 | 11/2003 | Fawls |
| 6,663,778 B1 | 12/2003 | Bader |
| 6,694,262 B2 | 2/2004 | Rozak |
| 6,705,398 B2 | 3/2004 | Weng |
| 6,715,553 B2 | 4/2004 | Reddy et al. |
| 6,729,409 B1 | 5/2004 | Gupta et al. |

(56) References Cited

U.S. PATENT DOCUMENTS

| | | |
|---|---|---|
| 6,747,270 B2 | 6/2004 | Pereira et al. |
| 6,749,022 B1 | 6/2004 | Fredd |
| 6,776,054 B1 | 8/2004 | Stephenson et al. |
| 6,776,235 B1 | 8/2004 | England |
| 6,831,108 B2 | 12/2004 | Dahanayake et al. |
| 6,832,158 B2 | 12/2004 | Mese et al. |
| 6,846,420 B2 | 1/2005 | Reddy et al. |
| 6,866,048 B2 | 3/2005 | Mattox |
| 6,875,728 B2 | 4/2005 | Gupta et al. |
| 6,881,709 B2 | 4/2005 | Nelson et al. |
| 6,884,760 B1 | 4/2005 | Brand et al. |
| 6,947,843 B2 | 9/2005 | Fisher et al. |
| 6,986,391 B2 | 1/2006 | Funkhouser et al. |
| 6,989,391 B2 | 1/2006 | Funkhouser |
| 7,001,872 B2 | 2/2006 | Pyecroft et al. |
| 7,007,752 B2 | 3/2006 | Reddy et al. |
| 7,011,154 B2 | 3/2006 | Maher et al. |
| 7,044,220 B2 | 5/2006 | Nguyen et al. |
| 7,052,901 B2 | 5/2006 | Crews |
| 7,063,150 B2 | 6/2006 | Slabaugh et al. |
| 7,077,199 B2 | 7/2006 | Vinegar et al. |
| 7,081,439 B2 | 7/2006 | Sullivan et al. |
| 7,086,484 B2 | 8/2006 | Smith |
| 7,091,719 B2 | 8/2006 | Freedman |
| 7,093,663 B1 | 8/2006 | Bader |
| 7,098,663 B1 | 8/2006 | Bader |
| 7,134,497 B1 | 11/2006 | Chatterji et al. |
| 7,148,185 B2 | 12/2006 | Fu et al. |
| 7,188,058 B2 | 3/2007 | Hardy |
| 7,198,722 B2 | 4/2007 | Hussain |
| 7,207,388 B2 | 4/2007 | Samuel et al. |
| 7,210,528 B1 | 5/2007 | Brannon et al. |
| 7,216,709 B2 | 5/2007 | McElfresh et al. |
| 7,252,146 B2 | 8/2007 | Slabaugh et al. |
| 7,255,169 B2 | 8/2007 | Van Batenburg et al. |
| 7,261,158 B2 | 8/2007 | Middaugh et al. |
| 7,281,580 B2 | 10/2007 | Parker et al. |
| 7,281,581 B2 | 10/2007 | Nyuyen et al. |
| 7,291,651 B2 | 11/2007 | Chen et al. |
| 7,299,874 B2 | 11/2007 | Welton et al. |
| 7,326,670 B2 | 2/2008 | DiLullo et al. |
| 7,334,635 B2 | 2/2008 | Nguyen |
| 7,334,636 B2 | 2/2008 | Nguyen |
| 7,341,980 B2 | 3/2008 | Lee et al. |
| 7,344,889 B2 | 3/2008 | Kelemen et al. |
| 7,369,980 B2 | 5/2008 | Deffenbaugh et al. |
| 7,373,977 B1 | 5/2008 | Berger et al. |
| 7,387,987 B2 | 6/2008 | Chen et al. |
| 7,424,911 B2 | 9/2008 | McCarthy et al. |
| 7,426,961 B2 | 9/2008 | Stephenson et al. |
| 7,451,812 B2 | 11/2008 | Cooper et al. |
| 7,472,748 B2 | 1/2009 | Gdanski et al. |
| 7,472,751 B2 | 1/2009 | Brannon et al. |
| 7,491,444 B2 | 2/2009 | Smith et al. |
| 7,500,517 B2 | 3/2009 | Looney et al. |
| 7,513,306 B2 | 4/2009 | Pfefferle et al. |
| 7,521,400 B2 | 4/2009 | Samuel |
| 7,526,418 B2 | 4/2009 | Pita et al. |
| 7,527,097 B2 | 5/2009 | Patel |
| 7,544,643 B2 | 6/2009 | Huang |
| 7,565,831 B2 | 7/2009 | Miyahara |
| 7,571,767 B2 | 8/2009 | Parker et al. |
| 7,581,590 B2 | 9/2009 | Lesko et al. |
| 7,588,085 B2 | 9/2009 | Acock et al. |
| 7,595,284 B2 | 9/2009 | Crews |
| 7,610,962 B2 | 11/2009 | Fowler |
| 7,615,517 B2 | 11/2009 | Huang et al. |
| 7,621,173 B2 | 11/2009 | Hsu |
| 7,642,223 B2 | 1/2010 | Santra et al. |
| 7,645,724 B2 | 1/2010 | Crews |
| 7,645,883 B1 | 1/2010 | Hawkins et al. |
| 7,654,159 B2 | 2/2010 | Enoksson |
| 7,655,603 B2 | 2/2010 | Crews |
| 7,678,723 B2 | 3/2010 | Duenckel et al. |
| 7,703,531 B2 | 4/2010 | Huang |
| 7,767,628 B2 | 8/2010 | Kippie et al. |
| 7,770,647 B2 | 8/2010 | Watson et al. |
| 7,771,549 B1 | 8/2010 | Christe et al. |
| 7,789,164 B2 | 9/2010 | Looney et al. |
| 7,803,740 B2 | 9/2010 | Bicerano et al. |
| 7,803,744 B2 | 9/2010 | Chen et al. |
| 7,806,182 B2 | 10/2010 | Waters et al. |
| 7,823,656 B1 | 11/2010 | Williams et al. |
| 7,825,053 B2 | 11/2010 | Duenckel et al. |
| 7,828,057 B2 | 11/2010 | Kearl et al. |
| 7,845,409 B2 | 12/2010 | Shinbach et al. |
| 7,857,055 B2 | 12/2010 | Li |
| 7,867,613 B2 | 1/2011 | Smith et al. |
| 7,878,246 B2 | 2/2011 | Samuel et al. |
| 7,878,248 B2 | 2/2011 | Abad et al. |
| 7,886,826 B2 | 2/2011 | Robinson et al. |
| 7,887,918 B2 | 2/2011 | Smith et al. |
| 7,908,230 B2 | 3/2011 | Bailey et al. |
| 7,918,277 B2 | 4/2011 | Brannon et al. |
| 7,921,911 B2 | 4/2011 | Fuller et al. |
| 7,933,018 B2 | 4/2011 | Vannuffelen et al. |
| 7,983,845 B2 | 7/2011 | Minh |
| 7,997,342 B2 | 8/2011 | Welton et al. |
| 8,003,212 B2 | 8/2011 | Smith et al. |
| 8,003,577 B2 | 8/2011 | Li et al. |
| 8,006,760 B2 | 8/2011 | Fleming et al. |
| 8,012,358 B2 | 9/2011 | Salbaugh et al. |
| 8,024,124 B2 | 9/2011 | Sayers |
| 8,047,288 B2 | 11/2011 | Skala et al. |
| 8,061,424 B2 | 11/2011 | Willberg et al. |
| 8,066,068 B2 | 11/2011 | Lesko et al. |
| 8,081,802 B2 | 12/2011 | Dvorkin et al. |
| 8,100,190 B2 | 1/2012 | Weaver |
| 8,104,536 B2 | 1/2012 | Looney et al. |
| 8,119,576 B2 | 2/2012 | Reyes et al. |
| 8,127,850 B2 | 3/2012 | Brannon et al. |
| 8,146,416 B2 | 4/2012 | Pisio et al. |
| 8,165,817 B2 | 4/2012 | Betancourt et al. |
| 8,177,422 B2 | 5/2012 | Kjoller et al. |
| 8,204,727 B2 | 6/2012 | Dean et al. |
| 8,205,675 B2 | 6/2012 | Brannon et al. |
| 8,216,675 B2 | 7/2012 | Palamara et al. |
| 8,225,866 B2 | 7/2012 | Rouffignac et al. |
| 8,278,931 B2 | 10/2012 | Fang et al. |
| 8,309,498 B2 | 11/2012 | Funkhouser et al. |
| 8,352,228 B2 | 1/2013 | Walters et al. |
| 8,380,437 B2 | 2/2013 | Abousleiman et al. |
| 8,408,305 B2 | 4/2013 | Brannon et al. |
| 8,450,252 B2 | 5/2013 | Funkhouser et al. |
| 8,473,213 B2 | 6/2013 | Zhu et al. |
| 8,490,700 B2 | 7/2013 | Lesko et al. |
| 8,573,302 B2 | 11/2013 | Robb et al. |
| 8,584,755 B2 | 11/2013 | Willberg et al. |
| 8,606,524 B2 | 12/2013 | Soliman et al. |
| 8,614,157 B2 | 12/2013 | Pope et al. |
| 8,614,573 B2 | 12/2013 | Minh |
| 8,616,294 B2 | 12/2013 | Zubrin et al. |
| 8,619,500 B2 | 12/2013 | Gray et al. |
| 8,636,065 B2 | 1/2014 | Lesko et al. |
| 8,646,524 B2 | 2/2014 | Al-Buriak |
| 8,653,011 B2 | 2/2014 | Samuel et al. |
| 8,701,760 B2 | 4/2014 | Parsche |
| 8,701,770 B2 | 4/2014 | Schultz |
| 8,701,788 B2 | 4/2014 | Wigand et al. |
| 8,729,903 B2 | 5/2014 | Srnka et al. |
| 8,731,889 B2 | 5/2014 | Du et al. |
| 8,757,259 B2 | 6/2014 | Lesko et al. |
| 8,763,699 B2 | 7/2014 | Medvedev et al. |
| 8,763,703 B2 | 7/2014 | Saini et al. |
| 8,778,852 B2 | 7/2014 | Huang |
| 8,796,187 B2 | 8/2014 | Reyes et al. |
| 8,815,096 B2 | 8/2014 | Zuback et al. |
| 8,821,806 B2 | 9/2014 | Hersherwitz et al. |
| 8,822,386 B2 | 9/2014 | Quintero et al. |
| 8,834,726 B2 | 9/2014 | Keister |
| 8,835,363 B2 | 9/2014 | Amanullah et al. |
| 8,839,860 B2 | 9/2014 | Wigand et al. |
| 8,844,366 B2 | 9/2014 | Warren |
| 8,851,177 B2 | 10/2014 | Wigand |

(56) References Cited

U.S. PATENT DOCUMENTS

| | | |
|---|---|---|
| 8,865,482 B2 | 10/2014 | Wang et al. |
| 8,868,385 B2 | 10/2014 | Fertig et al. |
| 8,877,041 B2 | 11/2014 | Parsche |
| 8,883,693 B2 | 11/2014 | Eldred et al. |
| 8,899,331 B2 | 12/2014 | Burnham et al. |
| 8,936,083 B2 | 1/2015 | Nguyen |
| 8,936,089 B2 | 1/2015 | Wigand |
| 8,967,249 B2 | 3/2015 | Akkurt et al. |
| 8,985,213 B2 | 3/2015 | Saini et al. |
| 9,006,151 B2 | 4/2015 | Amanullah et al. |
| 9,006,153 B2 | 4/2015 | Lin et al. |
| 9,033,033 B2 | 5/2015 | Thomas et al. |
| 9,033,043 B2 | 5/2015 | Hinkel |
| 9,034,802 B2 | 5/2015 | Ahrenst et al. |
| 9,046,509 B2 | 6/2015 | Dvorkin et al. |
| 9,057,797 B2 | 6/2015 | Omeragic et al. |
| 9,080,440 B2 | 7/2015 | Panga et al. |
| 9,085,477 B2 | 7/2015 | Banerjee et al. |
| 9,085,727 B2 | 7/2015 | Litvinets et al. |
| 9,091,161 B2 | 7/2015 | Brannon |
| 9,097,818 B2 | 8/2015 | Hursan |
| 9,128,210 B2 | 9/2015 | Pomerantz |
| 9,133,398 B2 | 9/2015 | Wigand et al. |
| 9,152,745 B2 | 10/2015 | Glinsky |
| 9,181,789 B2 | 11/2015 | Nevison |
| 9,222,902 B2 | 12/2015 | Gruber et al. |
| 9,266,754 B2 | 2/2016 | Fazrie et al. |
| 9,297,244 B2 | 3/2016 | Mahoney et al. |
| 9,341,052 B2 | 5/2016 | Gadberry et al. |
| 9,447,673 B2 | 9/2016 | Medvedev et al. |
| 9,453,156 B2 | 9/2016 | Wu |
| 9,523,268 B2 | 12/2016 | Potapenko et al. |
| 9,611,416 B2 | 4/2017 | Wang et al. |
| 9,644,137 B2 | 5/2017 | Dean et al. |
| 9,653,812 B2 | 5/2017 | Yan |
| 9,664,018 B2 | 5/2017 | Vandeponseele et al. |
| 9,670,764 B2 | 6/2017 | Lesko et al. |
| 9,688,904 B2 | 6/2017 | Wang et al. |
| 9,696,270 B1 | 7/2017 | Roy et al. |
| 9,725,639 B2 | 8/2017 | Vo et al. |
| 9,725,645 B2 | 8/2017 | Monastiriotis et al. |
| 9,739,905 B2 | 8/2017 | Sena |
| 9,753,016 B1 | 9/2017 | Daugela |
| 9,784,882 B2 | 10/2017 | Vinegar et al. |
| 9,816,365 B2 | 11/2017 | Nguyen et al. |
| 9,822,639 B2 | 11/2017 | Jandhyala |
| 9,834,721 B2 | 12/2017 | Chang et al. |
| 9,845,670 B2 | 12/2017 | Surjaatmadja et al. |
| 9,863,211 B2 | 1/2018 | Gamage et al. |
| 9,863,230 B2 | 1/2018 | Litvinets et al. |
| 9,863,231 B2 | 1/2018 | Hull et al. |
| 9,869,649 B2 | 1/2018 | Hull et al. |
| 9,885,691 B1 | 2/2018 | Daugela |
| 9,895,670 B2 | 2/2018 | Anders et al. |
| 9,896,919 B1 | 2/2018 | Chen |
| 9,902,898 B2 | 2/2018 | Nelson et al. |
| 9,909,404 B2 | 3/2018 | Hwang et al. |
| 9,927,344 B2 | 3/2018 | Chertov |
| 9,945,220 B2 | 4/2018 | Saini et al. |
| 9,995,125 B2 | 6/2018 | Madasu et al. |
| 9,995,220 B2 | 6/2018 | Hawie et al. |
| 10,001,769 B2 | 6/2018 | Huang et al. |
| 10,023,782 B2 | 7/2018 | Wang et al. |
| 10,030,495 B2 | 7/2018 | Litvinets et al. |
| 10,047,281 B2 | 8/2018 | Nguyen et al. |
| 10,066,149 B2 | 9/2018 | Li et al. |
| 10,077,396 B2 | 9/2018 | Nguyen et al. |
| 10,082,013 B2 | 9/2018 | Nguyen |
| 10,087,364 B2 | 10/2018 | Kaufman et al. |
| 10,100,245 B1 | 10/2018 | Bulekbay et al. |
| 10,113,396 B2 | 10/2018 | Nelson et al. |
| 10,144,866 B2 | 12/2018 | Liang |
| 10,151,715 B2 | 12/2018 | Hull et al. |
| 10,180,054 B2 | 1/2019 | Chen |
| 10,202,827 B2 | 2/2019 | Delchambre |
| 10,208,239 B2 | 2/2019 | Ballard |
| 10,273,398 B2 | 4/2019 | Liu et al. |
| 10,309,202 B2 | 6/2019 | Soliman |
| 10,329,478 B2 | 6/2019 | Schnoor et al. |
| 10,345,764 B2 | 7/2019 | Early et al. |
| 10,351,758 B2 | 7/2019 | Hull et al. |
| 10,379,068 B2 | 8/2019 | Hull et al. |
| 10,415,367 B2 | 9/2019 | Galford |
| 10,417,561 B2 | 9/2019 | Mohaghegh |
| 10,421,897 B2 | 9/2019 | Skiba et al. |
| 10,428,262 B2 | 10/2019 | Chakraborty et al. |
| 10,442,980 B2 | 10/2019 | Li |
| 10,443,367 B2 | 10/2019 | Chen |
| 10,451,601 B2 | 10/2019 | Han et al. |
| 10,472,555 B2 | 11/2019 | Hutchins et al. |
| 10,479,927 B2 | 11/2019 | Hull et al. |
| 10,501,680 B2 | 12/2019 | Li et al. |
| 10,550,314 B2 | 2/2020 | Liang et al. |
| 10,571,384 B2 | 2/2020 | Liu et al. |
| 10,611,967 B2 | 4/2020 | Inan |
| 10,619,469 B2 | 4/2020 | Han et al. |
| 10,647,909 B2 | 5/2020 | Li et al. |
| 10,655,443 B2 | 5/2020 | Gomma et al. |
| 10,669,829 B2 | 6/2020 | Liang et al. |
| 10,711,606 B2 | 7/2020 | Hull et al. |
| 10,775,360 B2 | 9/2020 | Han et al. |
| 10,781,360 B2 | 9/2020 | Hull et al. |
| 10,836,956 B2 | 11/2020 | Bulekbay et al. |
| 10,837,279 B2 | 11/2020 | Han et al. |
| 10,858,578 B2 | 12/2020 | Bulekbay et al. |
| 10,865,342 B2 | 12/2020 | Li et al. |
| 10,871,060 B2 | 12/2020 | Han et al. |
| 10,871,061 B2 | 12/2020 | Hull |
| 10,883,042 B2 | 1/2021 | Bulekbay |
| 10,895,140 B2 | 1/2021 | Cairns et al. |
| 11,001,750 B2 | 5/2021 | Li et al. |
| 11,028,312 B2 | 6/2021 | Li et al. |
| 11,098,564 B2 | 8/2021 | Li et al. |
| 11,162,357 B2 | 11/2021 | Liu et al. |
| 2001/0032055 A1 | 10/2001 | Omar |
| 2002/0003115 A1 | 1/2002 | Conaway et al. |
| 2002/0023752 A1 | 2/2002 | Qu |
| 2002/0147114 A1 | 10/2002 | Dobson, Sr. et al. |
| 2003/0171879 A1 | 9/2003 | Pittalwala |
| 2003/0173081 A1 | 9/2003 | Vinegar |
| 2003/0173082 A1 | 9/2003 | Vinegar |
| 2003/0192693 A1 | 10/2003 | Wellington |
| 2003/0209248 A1 | 11/2003 | Ward |
| 2003/0212465 A1 | 11/2003 | Howard et al. |
| 2003/0216263 A1 | 11/2003 | Tibbles et al. |
| 2003/0221831 A1 | 12/2003 | Reddy |
| 2004/0020642 A1 | 2/2004 | Vinegar |
| 2004/0033905 A1 | 2/2004 | Shinbach et al. |
| 2004/0101457 A1 | 5/2004 | Pahlman et al. |
| 2004/0173244 A1 | 9/2004 | Strothoff et al. |
| 2004/0211567 A1 | 10/2004 | Aud |
| 2004/0211568 A1 | 10/2004 | Funkhouser et al. |
| 2005/0016732 A1 | 1/2005 | Brannon |
| 2005/0039919 A1 | 2/2005 | Harris et al. |
| 2005/0059558 A1 | 3/2005 | Blauch et al. |
| 2005/0060130 A1 | 3/2005 | Shapiro et al. |
| 2005/0103118 A1 | 5/2005 | Workman |
| 2005/0137094 A1 | 6/2005 | Weaver et al. |
| 2005/0194147 A1 | 9/2005 | Metcalf et al. |
| 2005/0197257 A1 | 9/2005 | Bouwmeester |
| 2005/0274523 A1 | 12/2005 | Brannon et al. |
| 2006/0025321 A1 | 2/2006 | Treybig |
| 2006/0030632 A1 | 2/2006 | Krueger |
| 2006/0035808 A1 | 2/2006 | Ahmed et al. |
| 2006/0041411 A1 | 2/2006 | Yong et al. |
| 2006/0047489 A1 | 3/2006 | Scheidt et al. |
| 2006/0073980 A1 | 4/2006 | Brannon et al. |
| 2006/0084579 A1 | 4/2006 | Berger et al. |
| 2006/0092766 A1 | 5/2006 | Shelley et al. |
| 2006/0234871 A1 | 10/2006 | Dalrymple et al. |
| 2006/0265204 A1 | 11/2006 | Wallis et al. |
| 2007/0012437 A1 | 1/2007 | Clingman et al. |
| 2007/0054054 A1 | 3/2007 | Svoboda et al. |
| 2007/0087940 A1 | 4/2007 | Qu et al. |

(56) References Cited

U.S. PATENT DOCUMENTS

| | | |
|---|---|---|
| 2007/0137858 A1 | 6/2007 | Considine |
| 2007/0203677 A1 | 8/2007 | Awwiller |
| 2007/0235181 A1 | 10/2007 | Lecampion et al. |
| 2007/0298979 A1 | 12/2007 | Perry et al. |
| 2008/0006410 A1 | 1/2008 | Looney et al. |
| 2008/0059140 A1 | 3/2008 | Salmon et al. |
| 2008/0070806 A1 | 3/2008 | Lin et al. |
| 2008/0081771 A1 | 4/2008 | Lin et al. |
| 2008/0093073 A1 | 4/2008 | Bustos et al. |
| 2008/0103068 A1 | 5/2008 | Parris |
| 2008/0135242 A1 | 6/2008 | Lesko |
| 2008/0149329 A1 | 6/2008 | Cooper |
| 2008/0153718 A1 | 6/2008 | Heidenfelder et al. |
| 2008/0217012 A1 | 9/2008 | Delorey |
| 2008/0234147 A1 | 9/2008 | Li et al. |
| 2009/0032252 A1 | 2/2009 | Boney et al. |
| 2009/0044945 A1 | 2/2009 | Wilberg et al. |
| 2009/0071239 A1 | 3/2009 | Rojas et al. |
| 2009/0087912 A1 | 4/2009 | Ramos et al. |
| 2009/0095469 A1 | 4/2009 | Dozier |
| 2009/0132218 A1 | 5/2009 | Ledgerwood, III |
| 2009/0143252 A1 | 6/2009 | Lehmann |
| 2009/0145607 A1 | 6/2009 | Li et al. |
| 2009/0151944 A1 | 6/2009 | Fuller et al. |
| 2009/0193881 A1 | 8/2009 | Finnberg |
| 2009/0203557 A1 | 8/2009 | Barnes et al. |
| 2009/0205817 A1 | 8/2009 | Gustafson |
| 2009/0242196 A1 | 10/2009 | Pao |
| 2009/0248309 A1 | 10/2009 | Nelville et al. |
| 2009/0253595 A1 | 10/2009 | Qu |
| 2009/0277634 A1 | 11/2009 | Case |
| 2009/0283257 A1 | 11/2009 | Becker |
| 2009/0298720 A1 | 12/2009 | Nguyen et al. |
| 2009/0313772 A1 | 12/2009 | Talley |
| 2010/0010106 A1 | 1/2010 | Crews |
| 2010/0030527 A1 | 2/2010 | Prasad et al. |
| 2010/0043823 A1 | 2/2010 | Lee |
| 2010/0044049 A1 | 2/2010 | Leshchyshyn |
| 2010/0048430 A1 | 2/2010 | Funkhouser et al. |
| 2010/0049625 A1 | 2/2010 | Biebesheimer et al. |
| 2010/0051511 A1 | 3/2010 | Faerman |
| 2010/0121623 A1 | 5/2010 | Yogeswaren |
| 2010/0126936 A1 | 5/2010 | Jones |
| 2010/0128982 A1 | 5/2010 | Dvorkin et al. |
| 2010/0154514 A1 | 6/2010 | Algive |
| 2010/0186520 A1 | 7/2010 | Wheeler |
| 2010/0213579 A1 | 8/2010 | Henry |
| 2010/0224365 A1 | 9/2010 | Abad |
| 2010/0243242 A1 | 9/2010 | Boney et al. |
| 2010/0243248 A1 | 9/2010 | Golomb |
| 2010/0258265 A1 | 10/2010 | Karanikas et al. |
| 2010/0263867 A1 | 10/2010 | Horton et al. |
| 2010/0276142 A1 | 11/2010 | Skildum et al. |
| 2010/0279136 A1 | 11/2010 | Bonucci |
| 2010/0282468 A1 | 11/2010 | Willberg et al. |
| 2010/0294500 A1 | 11/2010 | Lesko |
| 2010/0312529 A1 | 12/2010 | Souche |
| 2010/0314113 A1 | 12/2010 | Huang |
| 2010/0323933 A1 | 12/2010 | Fuller et al. |
| 2011/0005969 A1 | 1/2011 | Giffin |
| 2011/0065612 A1 | 3/2011 | Stokes et al. |
| 2011/0083849 A1 | 4/2011 | Medvedev |
| 2011/0105369 A1 | 5/2011 | Reddy |
| 2011/0108277 A1 | 5/2011 | Dudley et al. |
| 2011/0257944 A1 | 10/2011 | Du et al. |
| 2011/0259588 A1 | 10/2011 | Ali |
| 2012/0006551 A1 | 1/2012 | Carman et al. |
| 2012/0018143 A1 | 1/2012 | Lembcke |
| 2012/0018159 A1 | 1/2012 | Gulta et al. |
| 2012/0022802 A1* | 1/2012 | Sakuma ............ G01N 3/42 702/43 |
| 2012/0026037 A1 | 2/2012 | Thomson et al. |
| 2012/0061081 A1 | 3/2012 | Sultenfuss et al. |
| 2012/0085534 A1 | 4/2012 | MorVan et al. |
| 2012/0097392 A1 | 4/2012 | Reyes et al. |
| 2012/0125618 A1 | 5/2012 | Willberg |
| 2012/0129737 A1 | 5/2012 | Lesko et al. |
| 2012/0160486 A1 | 6/2012 | Wigand |
| 2012/0179444 A1 | 7/2012 | Ganguly et al. |
| 2012/0193578 A1 | 8/2012 | Pan et al. |
| 2012/0205313 A1 | 8/2012 | Sathrugnan et al. |
| 2012/0214714 A1 | 8/2012 | Whitwell |
| 2012/0247764 A1 | 10/2012 | Panga |
| 2012/0247774 A1 | 10/2012 | Li et al. |
| 2012/0261129 A1 | 10/2012 | Becker |
| 2012/0261617 A1 | 10/2012 | Pan et al. |
| 2012/0267102 A1 | 10/2012 | Huang et al. |
| 2012/0273193 A1 | 11/2012 | Sen et al. |
| 2012/0305247 A1 | 12/2012 | Chen et al. |
| 2012/0318498 A1 | 12/2012 | Parsche |
| 2013/0013209 A1 | 1/2013 | Zhu et al. |
| 2013/0025867 A1 | 1/2013 | Sun et al. |
| 2013/0031971 A1 | 2/2013 | Freese et al. |
| 2013/0048562 A1 | 2/2013 | Keister |
| 2013/0056213 A1 | 3/2013 | Medvedev et al. |
| 2013/0084643 A1 | 4/2013 | Commarieu et al. |
| 2013/0090270 A1 | 4/2013 | Crews et al. |
| 2013/0118740 A1 | 5/2013 | Sherman et al. |
| 2013/0118744 A1 | 5/2013 | Gamage |
| 2013/0137610 A1 | 5/2013 | Huang et al. |
| 2013/0140031 A1 | 6/2013 | Cohen et al. |
| 2013/0160994 A1 | 6/2013 | Alsop et al. |
| 2013/0161002 A1 | 6/2013 | Wigand |
| 2013/0161003 A1 | 6/2013 | Mikhailovich et al. |
| 2013/0161008 A1 | 6/2013 | Klingler |
| 2013/0213120 A1 | 8/2013 | Lebedev |
| 2013/0213638 A1 | 8/2013 | Keller |
| 2013/0228019 A1 | 9/2013 | Meadows |
| 2013/0231908 A1 | 9/2013 | Williams et al. |
| 2013/0233536 A1 | 9/2013 | Alqam |
| 2013/0238304 A1 | 9/2013 | Glinsky |
| 2013/0260649 A1 | 10/2013 | Thomson |
| 2013/0264121 A1 | 10/2013 | Young |
| 2013/0269933 A1 | 10/2013 | Pomerantz et al. |
| 2013/0274149 A1 | 10/2013 | Lafitte et al. |
| 2013/0275099 A1 | 10/2013 | Frydman |
| 2013/0282386 A1 | 10/2013 | Vilermo et al. |
| 2013/0290064 A1 | 10/2013 | Altamirano et al. |
| 2013/0306321 A1 | 11/2013 | Lanctot-Downs et al. |
| 2013/0310492 A1 | 11/2013 | Morgan |
| 2013/0336612 A1 | 12/2013 | Pearce |
| 2013/0341028 A1 | 12/2013 | Christian et al. |
| 2014/0000899 A1 | 1/2014 | Nevison |
| 2014/0008305 A1 | 1/2014 | Nichols et al. |
| 2014/0014327 A1 | 1/2014 | Badri et al. |
| 2014/0027109 A1 | 1/2014 | Al-Baraik |
| 2014/0039797 A1 | 2/2014 | Gonzales |
| 2014/0045732 A1 | 2/2014 | Mazyar |
| 2014/0048694 A1 | 2/2014 | Pomerantz |
| 2014/0090850 A1 | 4/2014 | Benicewicz |
| 2014/0096964 A1 | 4/2014 | Chakraborty et al. |
| 2014/0116710 A1 | 5/2014 | Naser-El-Din et al. |
| 2014/0131040 A9 | 5/2014 | Panga |
| 2014/0144633 A1 | 5/2014 | Nguyen |
| 2014/0144634 A1 | 5/2014 | Nguyen |
| 2014/0144635 A1 | 5/2014 | Nguyen |
| 2014/0158632 A1 | 6/2014 | Govind et al. |
| 2014/0195215 A1 | 7/2014 | Chen et al. |
| 2014/0214326 A1 | 7/2014 | Samuel |
| 2014/0221257 A1 | 8/2014 | Roddy |
| 2014/0224472 A1 | 8/2014 | Parsche |
| 2014/0225607 A1 | 8/2014 | Edwards |
| 2014/0231077 A1 | 8/2014 | Rivero et al. |
| 2014/0239956 A1 | 8/2014 | Hoversten |
| 2014/0243246 A1 | 8/2014 | Hendrickson |
| 2014/0246244 A1 | 9/2014 | Shen |
| 2014/0247997 A1 | 9/2014 | Nishyama |
| 2014/0251605 A1 | 9/2014 | Hera |
| 2014/0260694 A1 | 9/2014 | Szlendak |
| 2014/0271321 A1 | 9/2014 | Maderud |
| 2014/0290943 A1 | 10/2014 | Ladva |
| 2014/0296113 A1 | 10/2014 | Reyes |
| 2014/0352954 A1 | 12/2014 | Lakhtychkin et al. |
| 2014/0353042 A1 | 12/2014 | Karale et al. |

(56) References Cited

U.S. PATENT DOCUMENTS

| | | |
|---|---|---|
| 2014/0364343 A1 | 12/2014 | Nelson et al. |
| 2014/0367100 A1 | 12/2014 | Oliveria et al. |
| 2014/0367111 A1 | 12/2014 | Gamage |
| 2014/0374104 A1 | 12/2014 | Kushal |
| 2015/0019183 A1 | 1/2015 | Suzuki |
| 2015/0039919 A1 | 2/2015 | Lim et al. |
| 2015/0041136 A1 | 2/2015 | Martin |
| 2015/0055438 A1 | 2/2015 | Yan et al. |
| 2015/0057097 A1 | 2/2015 | Cho |
| 2015/0057196 A1 | 2/2015 | Debord et al. |
| 2015/0065398 A1 | 3/2015 | Gartland et al. |
| 2015/0068749 A1 | 3/2015 | Wernimont |
| 2015/0071750 A1 | 3/2015 | Foster |
| 2015/0072902 A1 | 3/2015 | Lafitte et al. |
| 2015/0075782 A1 | 3/2015 | Sharma |
| 2015/0080271 A1 | 3/2015 | De Wolf et al. |
| 2015/0083405 A1 | 3/2015 | Dobroskok |
| 2015/0083420 A1 | 3/2015 | Gupta et al. |
| 2015/0083669 A1 | 3/2015 | Matherly et al. |
| 2015/0101808 A1 | 4/2015 | Saini et al. |
| 2015/0103624 A1 | 4/2015 | Thompson |
| 2015/0112488 A1 | 4/2015 | Hoehn et al. |
| 2015/0152724 A1 | 6/2015 | Amendt |
| 2015/0167439 A1 | 6/2015 | Kasevich et al. |
| 2015/0167440 A1 | 6/2015 | Kasevich |
| 2015/0192005 A1 | 7/2015 | Saeedfar |
| 2015/0198038 A1 | 7/2015 | Bartetzko |
| 2015/0211346 A1 | 7/2015 | Potapenko |
| 2015/0259593 A1 | 9/2015 | Kaufman et al. |
| 2015/0284625 A1 | 10/2015 | Silveira |
| 2015/0293256 A1 | 10/2015 | Dusterhoft |
| 2015/0300140 A1 | 10/2015 | Eoff et al. |
| 2015/0300968 A1 | 10/2015 | Bae et al. |
| 2015/0322759 A1 | 11/2015 | Okoniewski |
| 2015/0344771 A1 | 12/2015 | Jiang et al. |
| 2015/0368541 A1 | 12/2015 | Monclin et al. |
| 2015/0369028 A1 | 12/2015 | Potapenko |
| 2015/0369029 A1 | 12/2015 | Potapenko |
| 2016/0017202 A1 | 1/2016 | Yang et al. |
| 2016/0024367 A1 | 1/2016 | Zha |
| 2016/0040518 A1 | 2/2016 | Potapenko |
| 2016/0060504 A1 | 3/2016 | Dawson et al. |
| 2016/0061017 A1 | 3/2016 | Nguyen et al. |
| 2016/0103047 A1 | 4/2016 | Liu |
| 2016/0103049 A1 | 4/2016 | Liu |
| 2016/0130496 A1 | 5/2016 | Holtsclaw et al. |
| 2016/0137904 A1 | 5/2016 | Drake |
| 2016/0153274 A1 | 6/2016 | Hull et al. |
| 2016/0154133 A1 | 6/2016 | Donderici et al. |
| 2016/0170067 A1 | 6/2016 | Heaton |
| 2016/0177674 A1 | 6/2016 | Shetty et al. |
| 2016/0194551 A1 | 7/2016 | Waters et al. |
| 2016/0203239 A1 | 7/2016 | Samuel et al. |
| 2016/0208591 A1 | 7/2016 | Weaver et al. |
| 2016/0208602 A1 | 7/2016 | Donderici et al. |
| 2016/0215202 A1 | 7/2016 | Weaver et al. |
| 2016/0215205 A1 | 7/2016 | Nguyen |
| 2016/0215604 A1 | 7/2016 | Potapenko et al. |
| 2016/0230549 A1 | 8/2016 | Minh et al. |
| 2016/0237338 A1 | 8/2016 | Bianchi |
| 2016/0251567 A1 | 9/2016 | Lin et al. |
| 2016/0256583 A1 | 9/2016 | Yamada |
| 2016/0265331 A1 | 9/2016 | Weng et al. |
| 2016/0289543 A1 | 10/2016 | Chang et al. |
| 2016/0319187 A1 | 11/2016 | Lawrence et al. |
| 2016/0319189 A1 | 11/2016 | Dusterhoft |
| 2016/0341020 A1 | 11/2016 | Al-Buriak |
| 2016/0347994 A1 | 12/2016 | Purdy et al. |
| 2016/0362965 A1 | 12/2016 | Parlar et al. |
| 2016/0376494 A1 | 12/2016 | Li et al. |
| 2016/0379356 A1 | 12/2016 | Louis |
| 2017/0015895 A1 | 1/2017 | Cox |
| 2017/0030819 A1 | 2/2017 | Mccarty et al. |
| 2017/0031048 A1 | 2/2017 | Hilpert et al. |
| 2017/0032078 A1 | 2/2017 | Stelzer et al. |
| 2017/0051598 A1 | 2/2017 | Ouenes |
| 2017/0066959 A1 | 3/2017 | Hull et al. |
| 2017/0066962 A1 | 3/2017 | Ravi et al. |
| 2017/0067836 A1 | 3/2017 | Hull et al. |
| 2017/0121593 A1 | 5/2017 | Pantsurkin |
| 2017/0137699 A1 | 5/2017 | Song et al. |
| 2017/0137703 A1 | 5/2017 | Leverson et al. |
| 2017/0138190 A1 | 5/2017 | Elkatatny et al. |
| 2017/0145303 A1 | 5/2017 | Fontenelle et al. |
| 2017/0145793 A1 | 5/2017 | Ouenes |
| 2017/0154135 A1 | 6/2017 | Huang et al. |
| 2017/0175505 A1 | 6/2017 | Curlett |
| 2017/0176639 A1 | 6/2017 | Mosse et al. |
| 2017/0187177 A1 | 6/2017 | Mangum |
| 2017/0197853 A1 | 7/2017 | Chudasama et al. |
| 2017/0198207 A1 | 7/2017 | Li et al. |
| 2017/0241251 A1 | 8/2017 | Rodrigues et al. |
| 2017/0247997 A1 | 8/2017 | Kovalevsky |
| 2017/0248011 A1 | 8/2017 | Craddock et al. |
| 2017/0260848 A1 | 9/2017 | Xia |
| 2017/0275525 A1 | 9/2017 | Koep et al. |
| 2017/0235181 A1 | 10/2017 | Lecampion et al. |
| 2017/0328179 A1 | 11/2017 | Dykatra et al. |
| 2017/0336528 A1 | 11/2017 | Badri et al. |
| 2017/0370197 A1 | 12/2017 | Han et al. |
| 2017/0370895 A1* | 12/2017 | Han .................. G01N 3/42 |
| 2018/0037810 A1 | 2/2018 | Han et al. |
| 2018/0087350 A1 | 3/2018 | Sherman |
| 2018/0094519 A1 | 4/2018 | Stephens |
| 2018/0112126 A1 | 4/2018 | Yang et al. |
| 2018/0120213 A1 | 5/2018 | Dyshlyuk |
| 2018/0155602 A1 | 6/2018 | Zhang |
| 2018/0155615 A1 | 6/2018 | Rahy et al. |
| 2018/0179881 A1 | 6/2018 | Thompson |
| 2018/0195982 A1 | 7/2018 | Hull et al. |
| 2018/0196005 A1 | 7/2018 | Fanini |
| 2018/0202278 A1 | 7/2018 | Nelson et al. |
| 2018/0244981 A1 | 8/2018 | Panga et al. |
| 2018/0274312 A1 | 9/2018 | Zhou |
| 2018/0282616 A1 | 10/2018 | Debord et al. |
| 2018/0305208 A1 | 10/2018 | Mason |
| 2018/0319708 A1 | 11/2018 | Haque et al. |
| 2018/0321416 A1 | 11/2018 | Freedman |
| 2018/0322227 A1 | 11/2018 | Yateem et al. |
| 2018/0334612 A1 | 11/2018 | Bulekbay et al. |
| 2018/0348111 A1 | 12/2018 | Hannon |
| 2018/0355707 A1 | 12/2018 | Herrera et al. |
| 2018/0371882 A1 | 12/2018 | Delange |
| 2019/0010795 A1 | 1/2019 | Cascio et al. |
| 2019/0017203 A1 | 1/2019 | Andoh et al. |
| 2019/0062619 A1 | 2/2019 | Li et al. |
| 2019/0078424 A1 | 3/2019 | Copeland et al. |
| 2019/0112912 A1 | 4/2019 | Thompson et al. |
| 2019/0211658 A1 | 7/2019 | Hull et al. |
| 2019/0226970 A1 | 7/2019 | Dusterhoft et al. |
| 2019/0249066 A1 | 8/2019 | Monclin et al. |
| 2019/0257179 A1 | 8/2019 | Assaad |
| 2019/0257187 A1 | 8/2019 | Aljubran |
| 2019/0257729 A1 | 8/2019 | Han |
| 2019/0264095 A1 | 8/2019 | Qu et al. |
| 2019/0292436 A1 | 9/2019 | Mason et al. |
| 2019/0345377 A1 | 11/2019 | Haque et al. |
| 2019/0368346 A1 | 12/2019 | Liu et al. |
| 2020/0011169 A1 | 1/2020 | Haghshenas |
| 2020/0032636 A1 | 1/2020 | Chen et al. |
| 2020/0048531 A1 | 2/2020 | Hull et al. |
| 2020/0056464 A1 | 2/2020 | Li et al. |
| 2020/0095855 A1 | 3/2020 | Hughes |
| 2020/0339871 A1 | 10/2020 | Obot et al. |
| 2020/0378246 A1 | 12/2020 | Rodrigues |
| 2020/0386080 A1 | 12/2020 | Xu |
| 2021/0024808 A1 | 1/2021 | Schipper et al. |
| 2021/0024814 A1 | 1/2021 | Schipper et al. |
| 2021/0062071 A1 | 3/2021 | Li |
| 2021/0087915 A1 | 3/2021 | Han et al. |
| 2021/0124809 A1 | 4/2021 | Han et al. |
| 2021/0198553 A1 | 7/2021 | Hull et al. |
| 2021/0198558 A1 | 7/2021 | Hull et al. |
| 2021/0198559 A1 | 7/2021 | Hull et al. |

(56) References Cited

U.S. PATENT DOCUMENTS

| | | |
|---|---|---|
| 2021/0277762 A1 | 9/2021 | Liu et al. |
| 2021/0332686 A1 | 10/2021 | Safariforoshani |
| 2021/0355372 A1 | 11/2021 | Haque et al. |
| 2021/0406426 A1 | 12/2021 | Han et al. |
| 2022/0010667 A1 | 1/2022 | Han et al. |

FOREIGN PATENT DOCUMENTS

| | | |
|---|---|---|
| CA | 2635868 | 12/2008 |
| CN | 102221503 | 6/2011 |
| CN | 101819111 | 12/2011 |
| CN | 1621803 | 5/2012 |
| CN | 102737137 | 10/2012 |
| CN | 103387827 | 11/2013 |
| CN | 102183410 | 5/2014 |
| CN | 104346498 | 2/2015 |
| CN | 104727799 | 6/2015 |
| CN | 105445440 | 3/2016 |
| CN | 105567213 | 5/2016 |
| CN | 108751997 | 11/2018 |
| CN | 105131934 | 12/2018 |
| CN | 209841536 | 12/2019 |
| EA | 036572 | 3/2016 |
| EP | 0247669 | 12/1987 |
| EP | 0278540 | 8/1988 |
| EP | 0306546 | 3/1989 |
| EP | 0460927 | 12/1991 |
| EP | 0805260 | 11/1997 |
| EP | 2480625 | 4/2013 |
| EP | 2480626 | 4/2013 |
| EP | 3752315 | 12/2020 |
| FR | 2920435 | 8/2007 |
| GB | 2063840 | 6/1981 |
| GB | 2163790 | 3/1986 |
| GB | 2161269 | 8/1988 |
| GB | 2332223 | 6/1999 |
| JP | 2003113883 | 10/2001 |
| JP | 2014196444 | 10/2014 |
| RU | 2076204 | 3/1997 |
| WO | WO 1997028098 | 8/1997 |
| WO | WO 2000060379 | 10/2000 |
| WO | WO 2001094749 | 12/2001 |
| WO | WO 2002064702 | 8/2002 |
| WO | WO 2003025340 | 3/2003 |
| WO | WO 2004005435 | 1/2004 |
| WO | WO 2004061046 | 7/2004 |
| WO | WO 2005080012 | 9/2005 |
| WO | WO 2016108161 | 10/2006 |
| WO | WO 2008001218 | 1/2008 |
| WO | WO 2008018966 | 2/2008 |
| WO | WO 2008035253 | 3/2008 |
| WO | WO 2010026553 | 3/2010 |
| WO | WO 2010041025 | 4/2010 |
| WO | WO 2010138914 | 12/2010 |
| WO | WO 2011035292 | 3/2011 |
| WO | WO 2011035294 | 3/2011 |
| WO | WO 2012051647 | 4/2012 |
| WO | WO 2012057910 | 5/2012 |
| WO | WO 2012087887 | 6/2012 |
| WO | WO 2012087898 | 6/2012 |
| WO | WO 2012088476 | 6/2012 |
| WO | WO 2012104582 | 8/2012 |
| WO | WO 2012122505 | 9/2012 |
| WO | WO 2012171857 | 12/2012 |
| WO | WO 2013041633 | 3/2013 |
| WO | WO 2013052359 | 4/2013 |
| WO | WO 2013112114 | 8/2013 |
| WO | WO 2013149122 | 10/2013 |
| WO | WO 2013154926 | 10/2013 |
| WO | WO 2013155061 | 10/2013 |
| WO | WO 2014008496 | 1/2014 |
| WO | WO 2014008598 | 1/2014 |
| WO | WO 2014116305 | 7/2014 |
| WO | WO 2014123672 | 8/2014 |
| WO | WO 2014178504 | 11/2014 |
| WO | WO 2014190226 | 11/2014 |
| WO | WO 2014200611 | 12/2014 |
| WO | WO 2015012818 | 1/2015 |
| WO | WO 2015034478 | 3/2015 |
| WO | WO 2015041664 | 3/2015 |
| WO | WO 2015041669 | 3/2015 |
| WO | WO 2015071750 | 5/2015 |
| WO | WO 2015097116 | 7/2015 |
| WO | WO 2015103096 | 7/2015 |
| WO | WO 2015113302 | 8/2015 |
| WO | WO 2015126082 | 8/2015 |
| WO | WO 2015163858 | 10/2015 |
| WO | WO 2015181028 | 12/2015 |
| WO | WO 2015200060 | 12/2015 |
| WO | WO 2016032578 | 3/2016 |
| WO | WO 2016089813 | 6/2016 |
| WO | WO 2016094153 | 6/2016 |
| WO | WO 2016163983 | 10/2016 |
| WO | WO 2016182553 | 11/2016 |
| WO | WO 2017035371 | 3/2017 |
| WO | WO 2017040553 | 3/2017 |
| WO | WO 2017040824 | 3/2017 |
| WO | WO 2017040834 | 3/2017 |
| WO | WO 2017049039 | 3/2017 |
| WO | WO 2017065331 | 4/2017 |
| WO | WO 2017078674 | 5/2017 |
| WO | WO 2017086975 | 5/2017 |
| WO | WO 2017096055 | 6/2017 |
| WO | WO 2017106513 | 6/2017 |
| WO | WO 2017136641 | 8/2017 |
| WO | WO 2017161157 | 9/2017 |
| WO | WO 2018025010 | 2/2018 |
| WO | WO 2018045290 | 3/2018 |
| WO | WO 2018081477 | 5/2018 |
| WO | WO 2018118024 | 6/2018 |
| WO | WO 2018170065 | 9/2018 |
| WO | WO 2019140058 | 7/2019 |

OTHER PUBLICATIONS

U.S. Appl. No. 17/394,547, Schipper, filed Aug. 5, 2021.
U.S. Appl. No. 17/452,913, Shanmugam, filed Oct. 29, 2021.
U.S. Appl. No. 63/160,244, Cairns, filed Mar. 12, 2021.
"Hydraulic Fracturing Fluid Product Component Information Disclosure," Jan. 2012, 2 pages.
Abad et al., "Evaluation of the Material Properties of the Multilayered Oxides formed on HCM12A using New and Novel Techniques," Manuscript Draft, Manuscript No. OXID-D-15-00019, 2015, 44 pages.
Abass et al., "Wellbore Instability of Shale Formation, Zuluf Field, Saudi Arabia," Society of Petroleum Engineers (SPE), presented at the SPE Technical Symposium on Saudi Arabia Section, Dhahran, Saudi Arabia, May 21-23, 2006, 10 pages.
Abdelmalek et al., "Gas permeability measurements from pressure pulse decay laboratory data using pseudo-pressure and pseudo-time transformations." Journal of Petroleum Exploration and Production Technology 8.3, Jul. 2017, 839-847, 9 pages.
Abousleiman and Nguyen, "Poromechanics Response of Inclined Wellbore Geometry in Fractured Porous Media," Journal of Engineering Mechanics, vol. 131, No. 11, Nov. 2005, 14 pages.
Abousleiman et al., "A Micromechanically Consistent Poroviscoelasticity Theory for Rock Mechanics Applications," Int. J. Rock Mech. Min. Sci. & Geomech. Abstr., 1993, 30:7 (1177-1180), 4 pages.
Abousleiman et al., "Anisotropic Porothermoelastic Solution and Hydro-Thermal Effects on Fracture Width in Hydraulic Fracturing," International Journal for Numerical and Analytical Methods in Geomechanics, 2013, 25 pages.
Abousleiman et al., "GeoGenome Industry Consortium (G2IC)," JIP, 2004-2006, 6 pages.
Abousleiman et al., "Geomechanics Field and Laboratory Characterization of Woodford Shale: The Next Gas Play," SPE 110120, Society of Petroleum Engineers (SPE), presented at the 2007 SPE Annual Technical Conference and Exhibition on Nov. 11-14, 2007, 14 pages.

(56) References Cited

OTHER PUBLICATIONS

Abousleiman et al., "GeoMechanics Field Characterization of the Two Prolific U.S. Mid-West Gas Plays with Advanced Wire-Line Logging Tools," SPE 124428, Society of Petroleum Engineers (SPE), presented at the 2009 SPE Annual Technical Conference and Exhibition, Oct. 4-7, 2009, 19 pages.
Abousleiman et al., "Geomechanics Field Characterization of Woodford Shale and Barnett Shale with Advanced Logging Tools and Nano-indentation on Drill Cuttings," The Leading Edge, Special Section: Borehole Geophysics, Jun. 2010, 6 pages.
Abousleiman et al., "Mandel's Problem Revisited," Geotechnique, 1996, 46:2 (187-195), 9 pages.
Abousleiman et al., "Mechanical Characterization of Small Shale Samples subjected to Fluid Exposure using the Inclined Direct Shear Testing Device," International Journal of Rock Mechanics and Mining Sciences, 2010, 47:3 (355-367), 13 pages.
Abousleiman et al., "Modeling Real-Time Wellbore Stability within the Theory of Poromechanics," AADE-03-NTCE-11, American Association of Drilling Engineers (AADE), presented at the AADE 2003 National Technology Conference, Practical Solutions for Drilling Challenges, Texas, Apr. 1-3, 2003, 14 pages.
Abousleiman et al., "Poroelastic Solutions in Transversely Isotropic Media for Wellbore and Cylinder," Int. J. Solids Structures, 1998, 35:34-35 (4905-4929), 25 pages.
Abousleiman et al., "Poromechanics response of an inclined borehole subject to in-situ stress and finite length fluid discharge," Journal of Mechanics of Materials and Structures, Apr. 2010, 5(1):47-66.
Abousleiman et al., "Poroviscoelastic Analysis of Borehole and Cylinder Problems," ACTA Mechanica, 1996, 119: 199-219, 21 pages.
Abousleiman et al., "The Granular and Polymer Nature of Kerogen Rich Shale," Acta Geotechnica 2016, 11:3 (573-594), 24 pages.
Abousleiman et al., "Time-Dependent wellbore (in)stability predictions: theory and case study," IADC/SPE 62796, International Association of Drilling Contractors (IADC), Society of Petroleum Engineers (SPE), presented at the 2000 IADC/SPE Asia Pacific Drilling Technology held in Kuala Lumur, Malaysia, Sep. 11-13, 2000, 8 pages.
Agenet et al., "Fluorescent Nanobeads: a First Step Toward Intelligent Water Tracers," SPE 157019, Society of Petroleum Engineers (SPE), SPE International Oilfield Nanotechnology Conference, Jun. 12-14, 2012, 13 pages.
Agilent Technologies, "Field-Deployable Solution for Nanoporosity Measurements in Mud Logging Operations and a Novel Method for Fracability Analysis Using Mud Cuttings," Gulf Coast Conference, Agilent Restricted, Oct. 2013, 44 pages.
Ahmed et al. "7.2.2 Information Required to Move to a Pilot Project," Unconventional Resources Exploitation and Development, 2016, 1 page.
Alda, "Laser and Gaussian Beam Propagation and Transformation," Encyclopedia of Optical Engineering, Marcel Dekker, Inc., 2003, 15 pages.
AlDuailej et al., "CO 2 Emulsified Fracturing Fluid for Unconventional Applications," SPE-177405, Society of Petroleum Engineers, Abu Dhabi International Petroleum Exhibition and Conference held in Abu Dhabi, UAE, Nov. 9-12, 2015, 12 pages.
Al-Ghamdi et al., "Impact of Acid Additives on the Rheological Properties of Viscoelastic Surfactants and Their Influence on Field Application" SPE-89418-MS, Society of Petroleum Engineers, Presented at the SPE/DOE Symposium on Improved Oil Recovery, Tulsa, Apr. 17-21, 2004, 13 pages.
Alharbi, "Experimental Evaluation of the Effect of Carbonate Heterogeneity on Oil Recovery to Water and Gas Injections," University of Calgary, Sep. 9, 2013, 258 pages.
Allan et al., "A Multiscale Methodology for the Analysis of Velocity Anisotropy in Organic-Rich Shale," Geophysics, Jul.-Aug. 2015, 80:4 (C73-C88), 16 pages.
Alleman et al., "The Development and Successful Field Use of Viscoelastic Surfactant-based Diverting Agents for Acid Stimulation" SPE-80222-MS, Society of Petroleum Engineers, Presented at the International Symposium on Oilfield Chemistry, Houston, Feb. 5-7, 2004, 10 pages.
Al-Muntasheri, "A Critical Review of Hydraulic-Fracturing Fluids for Moderate- to Ultralow-Permeability Formations Over the Last Decade," SPE-169552-PA, Society of Petroleum Engineers, SPE Prod & Oper 29, Nov. 2014, (4):243-260, 18 pages.
Al-Munthasheri, "A Critical Review of Hydraulic Fracturing Fluids over the Last Decade," SPE 169552, Society of Petroleum Engineers (SPE), presented at the SPE Western North American and Rocky Mountain Joint Regional Meeting, Apr. 16-18, 2014, 25 pages.
Alnoaimi and Kovscek, "Experimental and Numerical Analysis of Gas Transport in Shale including the Role of Sorption," SPE-166375, Society of Petroleum Engineers (SPE), presented at the SPE Annual Technical Conference and Exhibition, Sep. 30-Oct. 2, 2013, 16 pages.
Althaus et al., "Permeability Estimation of a Middle-East Tight Gas Sand with NMR Logs," URTec: 2669857, Unconventional Resources Technology Conference (URTeC), proceedings of the 5th Unconventional Resources Technology Conference, Jul. 24, 2017, 7 pages.
Altowairqi, "Shale elastic property relationships as a function of total organic carbon content using synthetic samples," Journal of Petroleum Science and Engineering, Sep. 2015, 133: 392-400, 9 pages.
Al-Yami et al., "Engineered Fit-for-Purpose Cement System to Withstand Life-of-the-Well Pressure and Temperature Cycling," SPE-188488-MS, Society of Petroleum Engineers (SPE), presented at the Abu Dhabi International Petroleum Exhibition & Conference, Nov. 2017, 14 pages.
Amabeoku et al., "Calibration of Permeability Derived from NMR Lobs in Carbonate Reservoirs," SPE 68085, Society of Petroleum Engineers (SPE), presented at the 2001 SPE Middle East Oil Show, Mar. 17-20, 2001, 11 pages.
An et al., "A new study of magnetic nanoparticle transport and quantifying magnetization analysis in fractured shale reservoir using numerical modeling," Journal of Natural Gas Science and Engineering, 28:502-521, Jan. 2016, 21 pages.
Ananthan et al., "Influence of Strain Softening on the Fracture of Plain Concrete Beams," International Journal of Fracture, 1990, 45: 195-219, 25 pages.
Anisimov, "The Use of Tracers for Reservoir Characterization," SPE 118862, Society of Petroleum Engineers (SPE), presented at SPE Middle East Oil and Gas Show and Conference, Mar. 15-18, 2009, 8 pages.
APMonitor.com [online], "Proportional integral derivative (PID)," Sep. 2020, retrieved Oct. 13, 2021 from URL<https://apmonitor.com/pdc/index.php/Main/ProportionalIntegralDerivative>, 3 pages.
Arias et al., "New Viscoelastic Surfactant Fracturing Fluids Now Compatible with CO2 Drastically Improve Gas Production in Rockies," SPE-111431-MS, Presented at the SPE International Symposium and Exhibition on Formation Damage Control, Lafayette, Louisiana, Feb. 13-15, 2008, 5 pages.
Arns et al., "Computation of linear elastic properties from microtomographic images: Methodology and agreement between theory and experiment," Geophysics, Sep. 1, 2002, 67:5 (1396-1405), 10 pages.
Aslan et al., "Fluorescent Core—Shell AG@SiO$_2$ Nanocomposites for Metal-Enhanced Fluorescence and Single Nanoparticle Sensing Platforms," American Chemical Society (ACS), J. Am. Chem. Soc., JACS Communications, Jan. 19, 2007, 129: 1524-1525, 2 pages.
Atarita et al., "Predicting Distribution of Total Organic Carbon (TOC) and S2 with Δ Log Resistivity and Acoustic Impedance Inversion on Talang Akar Formation, Cipunegara Sub Basin, West Java," Procedia Engineering, 2017, 170: 390-397, 8 pages.
Ballice, "Solvent Swelling Studies of Goynuk (Kerogen Type-I) and Beypazari Oil Shales (Kerogen Type-II)," Science Direct, 2003, Fuel 82: 1317-1321, 5 pages.
Bandyopadhyay et al., "Effect of Silica Colloids on the Rheology of Viscoelastic Gels Formed by the Surfactant Cetyl Trimethylammonium Tosylate," J. Colloid Interf. Sci., 2005, 283(2):585-591, 7 pages.

(56) References Cited

OTHER PUBLICATIONS

Barati and Liang, "A Review of Fracturing Fluid Systems Used for Hydraulic Fracturing of Oil and Gas Wells," Journal of Applied Polymer Science, Aug. 15, 2014, 131:16, 11 pages.
Barenblatt et al., "Basic Concepts in the Theory of Seepage of Homogeneous Liquids in Fissured Rocks (Strata)," PMM 1960, 24:5 (852-864), 18 pages.
Barree et al., "Realistic Assessment of Proppant Pack Conductivity for Material Selection," Presented at the Annual Technical Conference, Denver, Colorado, SPE-84306-MS, Oct. 5-8, 2003, 12 pages.
Barton et al., "In-situ stress orientation and magnitude at the Fenton Geothermal Site, New Mexico, determined from wellbore breakouts," Geophysical Research Letters, May 1988, 15(5):467-470.
Basu et al., "Best Practices for Shale Core Handling: Transportation, Sampling and Storage for Conduction of Analyses," Journal of Marine Science and Engineering, Feb. 2020, 8(2):136, 17 pages.
Batarseh et al., "Well Perforation using High Power Laser," SPE 84418, SPE Annual Technical Conference and Exhibition, in Denver, Colorado, Oct. 5-8, 2003, 10 pages.
Bazant et al., "Deformation of Progressively Cracking Reinforced Concrete Beams," ACI Materials Journal, Technical Paper, Title No. 81-26, May-Jun. 1984, 81:3, 11 pages.
Bazant et al., "Size Effect in Brazilian Split-Cylinder Tests: Measurements and Fracture Analysis," ACI Materials Journal, Technical Paper, Title No. 88-M40, May 31, 1991, 88:3 (325-332), 8 pages.
Bazant et al., "Strain-Softening Bar and Beam: Exact Non-Local Solution," Int. J. Solids Structures, 1988, 24:7 (659-673), 15 pages.
Bell, "Perforating Underbalance—Evolving Techniques," SPE 13413, Distinguished Author Series, Journal of Petroleum Technology, vol. 36, Issue 10, Oct. 1984, 14 pages.
Bennett et al., "Instrumented Nanoindentation and 3D Mechanistic Modeling of a Shale at Multiple Scales," Acta Geotechnica, 10:21, Jan. 9, 2015, 14 pages.
Berger et al., "Effect of eccentricity, voids, cement channels, and pore pressure decline on collapse resistance of casing," SPE-90045-MS, Society of Petroleum Engineers (SPE), presented at the SPE Annual Technical Conference and Exhibition, Jan. 2004, 8 pages.
Bernheim-Groswasser et al., "Micellar Growth, Network Formation, and Criticality in Aqueous Solutions of the Nonionic Surfactant C12E5," Langmuir, Apr. 2000, 16(9):4131-4140, 10 pages.
Berryman, "Extension of Poroelastic Analysis to Double-Porosity Materials: New Technique in Microgeomechanics," Journal of Engineering Mechanics, 128:8 (840), Aug. 2002, 8 pages.
Bhandari et al., "Two-Dimensional DEM Analysis of Behavior of Geogrid-Reinforced Uniform Granular Bases under a Vertical Cyclic Load," Acta Geotechnica, Research Paper, 2015, 10: 469-480, 12 pages.
Bhandari et al., "Permeability Behavior and the Effective Stress Law for a Partially Fractured Eagle Ford Shale Sample." Poromechanics VI. 2017, 3 pages.
Biot et al., "Temperature analysis in hydraulic fracturing," Journal of Petroleum Technology, 39:11, Nov. 1987, 9 pages.
Biot, "General Theory of Three-Dimensional Consolidation," the Ernest Kempton Adams Fund for Physical Research of Columbia University, Reprint Series, Journal of Applied Physics, 12:2 (155-164), Feb. 1941, 11 pages.
Bisnovat et al., "Mechanical and petrophysical behavior of organic-rich chalk from the Judea Plains, Israel," Marine and Petroleum Geology, 64: 152-164, Jun. 2015, 13 pages.
Blanz et al., "Nuclear Magnetic Resonance Logging While Drilling (NMR-LWD): From an Experiment to a Day-to-Day Service for the Oil Industry," Diffusion Fundamentals, 2010, 14(2), 5 pages.
Bobko et al., "The Nanogranular Origin of Friction and Cohesion in Shale—A Strength Homogenization Approach to Interpretation of Nanoindentation Results," International Journal For Numerical and Analytical Methods in Geomechanics, 2010, 23 pages.
Borovik et al., "Computer-Aided, Single-Specimen Controlled Bending Test for Fracture-Kinetics Measurement in Ceramics," Journal of the American Ceramic Society, 1995, 78: 1305-1312, 8 pages.

Boskey et al., "Perspective—Collagen and Bone Strength," Journal of Bone and Mineral Research, 14:3, Nov. 3, 1999, 6 pages.
Bourbie and Walls, "Pulse decay permeability: analytical solution and experimental test," SPE Journal, 22:5, Oct. 1982, 11 pages.
Bourbie and Zinszner, "Hydraulic and Acoustic Properties as a Function of Porosity in Fontainebleau Sandstone," Journal of Geophysical Research, 90(B13):11,524-11,532, Nov. 1985, 9 pages.
Brace et al., "Permeability of granite under high pressure," Journal of Geophysics Res. 73:6, Mar. 15, 1968, 12 pages.
Bratton et al., "The Nature of Naturally Fractured Reservoirs," Oilfield Review, Jun. 2006, 21 pages.
Brezovski and Cui, "Laboratory permeability measurements of unconventional reservoirs: useless or full of information? A montney example from the western canadian sedimentary basin," Society of Petroleum Engineers, presented at the SPE Unconventional Resources Conference and Exhibition—Asia Pacific, Nov. 11-13, 2013, 12 pages.
Brochard et al., "Fracture Properties of Kerogen and Importance for Organic-Rich Shales," Annual World Conference on Carbon (Carbon 2013), Jul. 2013, 5 pages.
Brown et al., "Use of a Viscoelastic Carrier Fluid in Frack-Pack Applications," SPE-31114-MS, Society of Petroleum Engineers, Presented at the SPE Formation Damage Control Symposium, Lafayette, Louisiana, Feb. 14-15, 1996, 10 pages.
Bunzil et al., "Taking Advantage of Luminescent Lanthanide Ions," Chemical Society Reviews (CSR), Critical Review, 34: 1048-1077, Dec. 2005, 30 pages.
Bustos et al., "Case Study: Application of a Viscoelastic Surfactant-Based CO2 Compatible Fracturing Fluid in the Frontier Formation, Big Horn Basin, Wyoming," SPE-107966-MS, Society of Petroleum Engineers, Presented at the Rocky Mountain Oil & Gas Technology Symposium, Denver, Apr. 16-18, 2007, 11 pages.
Caenn et al., "Chapter 9: Wellbore Stability," p. 359, in Composition and Properties of Drilling and Completion Fluids, 7th Edition: Gulf Professional Publishing, 2016, 1 page.
Cahill et al., "Nanoscale Thermal Transport II," Applied Physics Reviews 1.1:011305, 2014, 46 pages.
Cahill et al., "Nanoscale Thermal Transport," Journal of Applied Physics 93:2, Jan. 15, 2003, 28 pages.
California Council on Science and Technology Lawrence Berkeley National Laboratory Pacific Institute, "Advanced Well Stimulation Technologies in California: An Independent Review of Scientific and Technical Information," CCST, Jul. 2016, 400 pages.
Carcione and Avseth, "Rock-physics templates for clay-rich source rocks," Geophysics 80:5 (D481-D500), Sep. 2015, 21 pages.
Carcione et al., "Theory of borehole stability when drilling through salt formations," Geophysics, 71:3, May-Jun. 2006, 17 pages.
Carter and Hanson, "Fake Moon Dirt, HOOD Solar System Science," UT Dallas Magazine, 6:2, Spring 2016, 1 page.
Cates, "Nonlinear Viscoelasticity of Wormlike Micelles (and Other Reversibly Breakable Polymers)," J. Phys. Chem., 1990, 94(1):371-375, 5 pages.
Cates, "Statics and Dynamics of Worm-Like Surfactant Micelles," J. Phys-Condens., 1990, Mat. 2(33):6869-6892, 25 pages.
Chang et al., "A Novel Self-Diverting-Acid Developed for Matrix Stimulation of Carbonate Reservoirs," SPE-65033-MS, Society of Petroleum Engineers, Presented at the SPE International Symposium on Oilfield Chemistry, Houston, Feb. 13-16, 2001, 6 pages.
Chang et al., "Experience in Acid Diversion in High Permeability Deep Water Formations Using Visco-Elastic-Surfactant," SPE-68919-MS, Society of Petroleum Engineers, Presented at the SPE European Formation Damage Conference, The Hague, The Netherlands, 21-22 May 21-22, 2001, 5 pages.
Chang et al., "Magnetic SERS Composite Nanoparticles for Microfluidic Detection," abstract to 251st ACE National Meeting, Mar. 13-17, 2016, 1 page (abstract).
Chang, "In-Situ Formation of Proppant and Highly Permeable Blocks for Hydraulic Fracturing," SPE-173328-MS, Society of Petroleum Engineers (SPE), SPE Hydraulic Fracturing Technology Conference Feb. 3-5, 2015, 11 pages.
Chatterji et al., "Applications of Water-Soluble Polymers in the Oil Field," SPE-9288-PA, J Pet Technol, Nov. 1981, 33(11): 2042-2056.

(56) References Cited

OTHER PUBLICATIONS

Chen et al, "Assessing Tensile Strength of Unconventional Tight Rocks Using Microwaving," URTec: 2154488, Unconventional Resources Technology Conference (URTeC), presented at the Unconventional Resources Technology Conference, Jul. 20-22, 2015, San Antonio, Texas, USA, 12 pages.

Chen et al, "Fracturing Tight Rocks by Elevated Pore-Water Pressure Using Microwaving and its Applications," SPWLA 56th Annual Logging Symposium, Jul. 18-22, 2015, Long Beach, California, USA, 13 pages.

Chen et al., "Novel CO2-Emulsified Viscoelastic Surfactant Fracturing Fluid System," SPE-94603-MS, Society of Petroleum Engineers, Presented at the SPE European Formation Damage Conference, Scheveningen, The Netherlands, May 25-27, 2005, 6 pages.

Chen et al., "Optimization of NMR Permeability Transform and Application to Middle East Tight Sands," Society of Petrophysicists and Well-Log Analysts, SPWLA 58th Annual Logging Symposium, Jun. 17-21, 2017, 11 pages.

Chen et al., "Size Effect in Micro-Scale Cantilever Beam Bending," Acta Mech., 219: 291-307, 2011, 17 pages.

Chen et al., "FITC functionalized magnetic core-shell $Fe_3O_4$/Ag hybrid nanoparticle for selective determination of molecular biothiols," Sensors and Actuators B: Chemical, 193: 857-863, Dec. 2013, 7 pages.

Chen, "Three-dimensional analytical poromechanical solutions for an arbitrarily inclined borehole subjected to fluid injection," Proceedings of the Royal Society A: Mathematical, Physical and Engineering Sciences, Jan. 2019, 475(2221):20180658.

Chen, et al., "Dependence of gas shale fracture permeability on effective stress and reservoir pressure: Model match and insights," Fuel, 2015, 139:383-392.

Cheng et al., "Cotton aerogels and cotton-cellulose aerogels from environmental waste for oil spillage cleanup," Materials & Design, Elsevier, May 28, 2017, 130:452-458, 7 pages.

Chern et al., "Deformation of Progressively Cracking Partially Prestressed Concrete Beams," PCI Journal, 37:1 (74-84), 1992, 11 pages.

Cheshomi et al., "Determination of uniaxial compressive strength of microcystalline limestone using single particles load test," Journal of Petroleum Science and Engineering, 111: 121-126, 2013, 6 pages.

Chevalier et al., "Micellar Properties of Zwitterionic Phosphobetaine Amphiphiles in Aqueous Solution: Influence of the Intercharge Distance," Colloid Polym. Sci., 1988, 266(5):441-448, 8 pages.

Chevalier et al., "Structure of Zwitterionic Surfactant Micelles: Micellar Size and Intermicellar Interactions," J. Phys. Chem., Jun. 1992, 96(21):8614-8619, 6 pages.

Christiawan et al., "Innovative Multi Technologies Collaboration for Ultra-HP/H Offshore Fracturing Stimulation," OTC-26663-MS, Offshore Technology Conference (OTC), presented at the Offshore Technology Conference Asia, Mar. 22-25, 2016, 26 pages.

Chuang et al., "Ultra-sensitive in-situ detection of novel near-infrared persistent luminescent tracer nanoagents in crude oil-water mixtures," a natureresearch journal, Scientific Reports, Jun. 15, 2016, 5 pages.

Chuanliang et al., "Wellbore stability analysis and its application in the Fergana basin, central Asia." Journal of Geophysics and Engineering 11.1, Feb. 2014, 9 pages.

Chun et al., "Fracture Propagation under Poroelastic Loading," ARMA 12-274, presented at the 46th US Rock Mechanics/Geomechanics Symposium, Chicago, IL, Jun. 24-27, 2012, 9 pages.

Chupin et al., "Finite Strain Analysis of Nonuniform Deformation Inside Shear Bands in Sands," International Journal for Numerical and Analytical Methods in Geomechanics, 36: 1651-1666, 2012, 16 pages.

Civan, et al., "Comparison of shale permeability to gas determined by pressure-pulse transmission testing of core plugs and crushed samples," Unconventional Resources Technology Conference, Jul. 2015.

Clarkson et al., "Use of pressure- and rate-transient techniques for analyzing core permeability tests for unconventional reservoirs: Part 2," SPE Unconventional Resources Conference, Nov. 2013.

Clough et al., "Characterization of Kerogen and Source Rock Maturation Using Solid-State NMR Spectroscopy," Energy & Fuels, 2015, 29(10): 6370-6382, 42 pages.

Cooper et al., "The effect of cracks on the thermal expansion of rocks," Earth and Planetary Science Letters, Oct. 1, 1977, 36(3):404-12, 9 pages.

Corapcioglu, "Fracturing Fluid Effects on Young's Modulus and Embedment in the Niobrara Formation," Thesis for degree of Master of Science (Petroleum Engineering), Colorado School of Mines, 2014, 189 pages.

Couillet et al., "Synergistic Effects in Aqueous Solutions of Mixed Wormlike Micelles and Hydrophobically Modified Polymers," Macromolecules, American Chemical Society, 2005, 38(12):5271-5282, 12 pages.

Crews et al., "Internal Breakers for Viscoelastic Surfactant Fracturing Fluids," SPE-106216-MS, Society of Petroleum Engineers, Presented at the International Symposium on Oilfield Chemistry, Houston, Feb. 28-Mar. 2, 2007, 8 pages.

Crews et al., "Internal Phase Breaker Technology for Viscoelastic Surfactant Gelled Fluids," SPE-93449-MS, Society of Petroleum Engineers, Presented at the SPE International Symposium on Oilfield Chemistry, Houston, 2-4 Feb. 2-4, 2005, 11 pages.

Crews et al., "New Remediation Technology Enables Removal of Residual Polymer in Hydraulic Fractures," SPE-135199-MS, Society of Petroleum Engineers, Presented at the SPE Annual Technical Conference and Exhibition, Florence, Italy, Sep. 19-22, 2010.

Crews et al., "New Technology Improves Performance of Viscoelastic Surfactant Fluids" SPE-103118-PA, Society of Petroleum Engineers, SPE Drill & Compl, SPE Annual Technical Conference and Exhibition, San Antonio, Texas, Sep. 24-27, 2008, 23(1):41-47, 7 pages.

Crews et al., "Performance Enhancements of Viscoelastic Surfactant Stimulation Fluids with Nanoparticles," SPE-113533-MS, Society of Petroleum Engineers, Presented at the Europec/EAGE Annual Conference and Exhibition, Rome, Jun. 9-12, 2008, 10 pages.

Crews et al., "The Future of Fracturing—Fluid Technology and Rates of Hydrocarbon Recovery," SPE-115475-MS, Society of Petroleum Engineers, Presented at the SPE Annual Technical Conference and Exhibition, Denver, Sep. 21-24, 2008, 13 pages.

Cronin, "Core-scale heterogeneity and dual-permeability pore structures in the Barnett Shale," Thesis for Degree of Master of Science in Geological Sciences at the University of Texas at Austin, Dec. 2014, 174 pages.

Cubillos et al., "The Value of Inter-well and Single Well Tracer Technology for De-Risking and Optimizing a CEOR Process—Caracara Field Case," SPE 174394-MS, Society of Petroleum Engineers (SPE), presented at EUROPEC 2015, Jun. 1-4, 2015, 19 pages.

Cui et al., "Measurements of gas permeability and diffusivity of tight reservoir rocks: different approaches and their applications," Geofluids, 9:3, Aug. 2009, presented at the AAPG Convention, Jun. 7-10, 2009, 18 pages.

Cui et al., "Poroelastic solution for an inclined borehole," Journal of Applied Mechanics, Mar. 1997, 64(1):32-38.

Custelcean et al., "Aqueous Sulfate Separation by Crystallization of Sulfate-Water Clusters," Angewandte Chemie, International Edition, 2015, 54: 10525-10529, 5 pages.

Dagan, "Models of Groundwater Flow in Statistically Homogeneous Porous Formations," Water Resource Search 15:1, Feb. 1979, 17 pages.

Dall'Acqua et al., "Burst and collapse responses of production casing in thermal applications." SPE Drilling & Completion 28.01, Mar. 2013, 93-104, 12 pages.

Daneshy, "Hydraulic Fracturing to Improve Production," Tech 101, The WayAhead, 6:3, Oct. 2010, 4 pages.

Daniel et al., "New Visco-Elastic Surfactant Formulations Extend Simultaneous Gravel-Packing and Cake-Cleanup Technique to Higher-Pressure and Higher-Temperature Horizontal Open-Hole Completions: Laboratory Development and a Field Case History From the North Sea," SPE-73770-MS, Society of Petroleum Engineers, Pre-

(56) References Cited

OTHER PUBLICATIONS sented at the SPE International Symposium and Exhibition on Formation Damage, Lafayette, Louisiana, Feb. 20-21, 2002, 10 pages.

Darabi et al., "Gas flow in ultra-tight shale strata," Journal of Fluid Mechanics, 710, Nov. 10, 2012, 20 pages.

Das et al., "Molecular Fluorescence, Phosphorescence, and Chemiluminescence Spectrometry," American Chemical Society Publications (ACS), Analytical Chemistry, 84: 597-625, Nov. 3, 2011, 29 pages.

De Block et al., "A New Solution for the Characterization of Unconventional Shale Resources Based on Analysis or Drill Cutting," SPE-177601-MS, Society of Petroleum Engineers (SPE), presented at the Abu Dhabi International Petroleum Exhibition and Conference, Nov. 9-12, 2015, 6 pages.

De Rocha et al., "Concentrated CO2-in-Water Emulsions with Nonionic Polymeric Surfactants," Journal of Colloid and Interface Science, 2001, 239:1 (241-253), 13 pages.

Deans, "Using Chemical Tracers To Measure Fractional Flow And Saturation In-Situ," SPE 7076, Society of Petroleum Engineers (SPE) of AIME, presented at Fifth Symposium on Improved Methods for Oil Recovery of the Society of Petroleum Engineers of AIME, Apr. 16-19, 1978, 10 pages.

Deirieh et al., "Nanochemomechanical Assessment of Shale: A Coupled WDS-Indentation Analysis," Acta Geotechnica, Research Paper, Sep. 2012, 25 pages.

Delafargue and Ulm, "Explicit approximations of the indentation modulus of elastically orthotropic solids for conical indenters," International Journal of Solids and Structures 41:26 (7351-7360), Dec. 2004, 10 pages.

Detournay and Cheng, "Poroelastic Response of a Borehole in a Non-Hydrostatic Stress Field," International Journal of Rock Mechanics, Min. Science and Geomech. Abstracts, 25:3, 1988, 12 pages.

Devarapalli et al., "Micro-CT and FIB-SEM imaging and pour structure characterization of dolomite rock at multiple scales," Arabian Journal of Geosciences 10:361, Aug. 2017, 9 pages.

Di Lullo et al., "Toward Zero Damage: New Fluid Points the Way," SPE-69453-MS, Society of Petroleum Engineers, Presented at the SPE Latin American and Caribbean Petroleum Engineering Conference, Buenos Aires, Argentina, Mar. 25-28, 2001, 8 pages.

Dicker and Smits, "A practical approach for determining permeability from laboratory pressure-pulse decay measurements," SPE-17578, Society of Petroleum Engineers (SPE), presented at the SPE international Meeting on Petroleum Engineering, Nov. 1-4, 1988, 8 pages.

Dobroskok et al., "Estimating Maximum Horizontal Stress from Multi-Arm Caliper Data in Vertical Wells in Oman," SPE 183204-MS, Society of Petroleum Engineers (SPE), presented at the Abu Dhabi International Petroleum Exhibition & Conference, Nov. 2016, 7 pages.

Dong et al., "A comparative experimental study of shale indentation fragmentation mechanism at the macroscale and mesoscale," Advances in Mechanical Engineering, Aug. 2017, 9(8): 1-11, 11 pages.

Dou et al., "Effect of joint parameters on fracturing behavior of shale in notched three-point-bending test based on discrete element model." Engineering Fracture Mechanics 205 Nov. 2019, 40-56, 17 pages.

Drdlova et al., "Effect of Nanoparticle Modification on Static and Dynamic Behavior of Foam Based Blast Energy Absorbers," Cellular Polymers, 35:3, May 2016, 16 pages.

Dreiss, "Wormlike Micelles: Where Do We Stand? Recent Developments, Linear Rheology, and Scattering Techniques," The Royal Society of Chemistry, Soft Matter, 2007, 3(8):956-970, 15 pages.

Dropek et al., "Pressure-temperature creep testing as applied to a commercial rock salt," Union Carbide, Office of Waste Isolation, prepared for the U.S. Energy Research and Development Administration, Jun. 1976, 54 pages.

Du et al., "Interwell Tracer Tests: Lessons Learned from past Field Studies," SPE 93140, Society of Petroleum Engineers (SPE), presented at SPE Asia Pacific Oil and Gas Conference and Exhibition, Apr. 5-7, 2005, 9 pages.

Ducros, "Source Rocks of the Middle East," Source Rock Kinetics: Goal and Perspectives. AAPG Geosciences Technology Workshop, Jul. 2016, 30 pages.

Dvorkin, "Kozeny-Carman Equation Revisited," 2009, 16 pages.

Eastoe et al., "Water-in-CO2 Microemulsions Studied by Small-Angle Neutron Scattering," Langmuir 1997, 13:26 (6980-6984), 5 pages.

Economides et al., Reservoir Stimulation, 2nd ed., Prentice Hall, Englewood Cliffs, New Jersey, 1989, 408 pages.

Egermann et al., "A fast and direct method of permeability measurements on drill cuttings," Society of Petroleum Engineers (SPE), SPE Reservoir Evaluation and Engineering, 8:4, Aug. 2005, 7 pages.

Ehlig-Economides and Economides, "Water as Proppant," SPE-147603, Society of Petroleum Engineers (SPE), presented at the SPE Annual Technical Conference and Exhibition, Oct. 30-Nov. 2, 2011, 8 pages.

Ekbote et al., "Porochemoelastic Solution for an Inclined Borehole in a Transversely Isotropic Formation," Journal of Engineering Mechanics, ASCE, Jul. 2006, 10 pages.

El-Aneed et al., "Mass Spectrometry, Review of the Basics: Electrospray, MALDI, and Commonly Used Mass Analyzers," Applied Spectroscopy Reviews 44:3 (210-230), Mar. 16, 2009, 22 pages.

Elijah, "Numerical Modeling of Wellbore Instability (Tensile Failure) Using Fracture Mechanics Approach," Thesis for the degree of Master of Science, African University of Science and Technology Abuja, May 2013, 77 pages.

Eliyahu et al., "Mechanical Properties of organic matter in shales mapped at the nanometer scale," Marine and Petroleum Geology, 59:294-304, Sep. 18, 2014, 11 pages.

Elsemongy et al., "Thermodynamics of Hydrochloric Acid in Ethylene Glycol + Water Mixtures from Electromotive Force Measurements," Chemistry Department, Faculty of Science, Mansoura University, Egypt, Feb. 1982, 129(2): 185-196, 12 pages.

Ertas et al., "Petroleum Expulsion Part 1. Theory of Kerogen Swelling in Multicomponent Solvents," Energy & Fuels, 20: 295-300, 2006, 6 pages.

Eseme et al., "Review of mechanical properties of oil shales: implications for exploitation and basin modeling," Oil Shale 24:2 (159-174), Jan. 2007, 16 pages.

Esfahani et al., "Quantitative nanoscale mapping of three-phase thermal conductivities in filled skutterudites via scanning thermal microscopy," Nature Science Review 5:1, Feb. 2017, 31 pages.

Ewy, "Shale Swelling/Shrinkage and Water Content Change due to Imposed Suction and Due to Direct Brine Contact," Acta Geotechnica, 9: 869-886, 2014, 18 pages.

Ewy, "Wellbore-Stability Predictions by Use of a Modified Lade Criterion," SPE Drill and Completion, 14:2, Jun. 1999, 7 pages.

Fakoya et al., "Rheological Properties of Surfactant-Based and Polymeric Nano-Fluids," SPE-163921-MS, Society of Petroleum Engineers, Presented at the SPE/ICoTA Coiled Tubing and Well Intervention Conference and Exhibition, The Woodlands, Texas, Mar. 26-27, 2013, 17 pages.

Fatahi, "Simulation of Shale Mechanical Properties in PFC2d and Calibration of Them Against Lab Results for Tensile, Uni-axial and Confined Compression Tests," Society of Petroleum Engineers, Oct. 2014, 1-12.

fekete.com [online], "Dual Porosity," retrieved from URL <www.fekete.com/SAN/WebHelp/FeketeHarmony/Harmony_WebHelp/Content/HTML_Files/Reference_Material/General_Concepts/Dual_Porosity.htm>, available on or before 2014, retrieved on Nov. 11, 2019, 6 pages.

Finney, "Random packings and the structure of simple liquids I. The geometry of random close packing," Proc. Roy. Soc. Lond. 319, 479-493, May 1970, 15 pages.

Finsterle and Persoff, "Determining permeability of tight rock samples using inverse modeling," Water Resources Research, 33:8, Aug. 1997, 9 pages.

(56) References Cited

OTHER PUBLICATIONS

Fjaer et al., "Stresses around Boreholes. Borehole Failure Criteria," in Petroleum Related Rock Mechanics, 2nd Edition, 2008, 156, 1 page.

Fontana et al., "Successful Application of a High Temperature Viscoelastic Surfactant (VES) Fracturing Fluids Under Extreme Conditions in Patagonian Wells, San Jorge Basin," SPE-107277-MS, Society of Petroleum Engineers, Presented at the EUROPEC/EAGE Annual Conference and Exhibition, London, Jun. 11-14, 2007, 15 pages.

Forni et al., "Conditioning Pre-existing Old Vertical Wells to Stimulate and Test Vaca Muerta Shale Productivity through the Application of Pinpoint Completion Techniques," SPE-172724-MS, Society of Petroleum Engineers (SPE), presented at the SPE Middle East Oil and Gas Show, Mar. 8-11, 2015, 28 pages.

Frazer et al., "Localized Mechanical Property Assessment of SiC/SiC Composite Materials," Science Direct, Composites: Part A, 70: 93-101, 2015, 9 pages.

Fredd et al., "Polymer-Free Fracturing Fluid Exhibits Improved Cleanup for Unconventional Natural Gas Well Applications" SPE-91433-MS, Society of Petroleum Engineers, Presented at the SPE Eastern Regional Meeting, Charleston, West Virginia, Sep. 15-17, 2004, 15 pages.

Funkhouser and Norman, "Synthetic Polymer Fracturing Fluid for High-Temperature Application," International Symposium on Oilfield Chemistry, Society of Petroleum Engineers, SPE 80236, Feb. 5-7, 2003, 6 pages.

Gahan et al., "Determination of Energy Required to Remove Rock," SPE 71466, presented at the 2001 SPE Annual Technical Conference and Exhibition, in New Orleans, Louisiana, Sep. 30-Oct. 3, 2001, 11 pages.

Gaillard et al., "Novel Associative Acrylamide-based Polymers for Proppant Transport in Hydraulic Fracturing Fluids", SPE 164072, Society of Petroleum Engineers (SPE), SPE International Symposium on Oilfield Chemistry, Apr. 8-10, 2013, 11 pages.

Gallegos and Varela, "Trends in Hydraulic Fracturing Distributions and Treatment Fluids, Additives, Proppants, Water Volumes Applied to Wells Drilled in the United States from 1947 through 2010—Data Analysis and Comparison to the Literature," USGS, United States Geological Survey, 2015, 24 pages.

Gandossi and Estorff, "An overview of hydraulic fracturing and other formation stimulation technologies for shale gas production," JRC Science for Policy Report, European Commission, EUR 26347 EN, Jan. 2013, 62 pages.

Ganesh et al., "A Generalized Thermal Modeling for Laser Drilling Process—I. Mathematical Modeling and Numerical Methodology," International Journal of Heat and Mass Transfer, vol. 40, Issue 14, Sep. 1997, 10 pages.

Ganjdanesh et al. "Treatment of Condensate and Water Blocks in Hydraulic-Fractured Shale-Gas/Condensate Reservoirs," SPE-175145, Society of Petroleum Engineers (SPE), presented at the SPE Annual Technical Conference and Exhibition, Sep. 28-30, 2015, SPE Journal, Apr. 2016, 10 pages.

Gao et al., "Materials Become Insensitive to Flaws at Nanoscale: Lessons from Nature," PNAS, 100:10, May 13, 2003, 4 pages.

Gardiner et al., "Chapter 1: Introduction to Raman Scattering," in Practical Raman Spectroscopy, Springer-Verlag, 1989, 9 pages.

Garnero, "The Contribution of Collagen Crosslinks to Bone Strength," Int. Bone & Mineral Society, BoneKEy Reports 1:182, Sep. 2012, 8 pages.

George et al., "Approximate relationship between frequency-dependent skin depth resolved from geoelectronnagnetic pedotransfer function and depth of investigation resolved from geoelectrical measurements: A case study of coastal formation, southern Nigeria," Journal of Earth Syst. Sci, 125:7 (1379-1390), Oct. 2016, 12 pages.

Georgi et al., "Physics and Chemistry in Nanoscale Rocks," Society of Petroleum Engineers (SPE), SPE Forum Series, Frontiers of Technology, Mar. 22-26, 2015, 4 pages.

Gholami et al., "A methodology for wellbore stability analysis of drilling into presalt formations: A case study from southern Iran." Journal of Petroleum Science and Engineering 167, Aug. 2018, 249-261, 28 pages.

Gillard et al., "A New Approach to Generating Fracture Conductivity," presented at the SPE Annual Technical Conference and Exhibition held in Florence, Italy, SPE-135034-MS, Sep. 20-22, 2010, 14 pages.

Glossary.oilfield.slb.com [online], "Oilfield Glossary: fluid-friction reducer," available on or before Jun. 15, 2017, retrieved from URL<http://www.glossary.oilfield.slb.com/Terms/f/fluid-friction_reducer.aspx>, 1 page.

Glover et al., "The Use of Measurements Made on Drill Cuttings to Construct and Apply Geomechanical Well Profiles," ARMA 16-0737, American Rock Mechanics Association (ARMA), presentation at the 50th US Rock Mechanics/Geomechanics Symposium, Jun. 26-29, 2016, 11 pages.

Godwin et al., "Simultaneous Gravel Packing and Filter-Cake Cleanup with Shunt Tubes in Openhole Completions: A Case History From the Gulf of Mexico," SPE-78806, Society of Petroleum Engineers, SPE Drill & Compl, Sep. 2002, 17(3):174-178, 5 pages.

Golomb et al, "Macroemulsion of liquid and supercritical $CO_2$-in-water and water-in-liquid $CO_2$ stabilized with fine particles," American Chemical Society (ACS), Ind. Eng. Chem. Res. 2006, 45:8 (2728-2733), 6 pages.

Gomaa et al., "Acid Fracturing: The Effect of Formation Strength on Fracture Conductivity," Paper SPE 119623 presented at the SPE Hydraulic Fracturing Technology Conference, Jan. 2009, 18 pages.

Gomaa et al., "Computational Fluid Dynamics Applied to Investigate Development and Optimization of Highly Conductive Channels within the Fracture Geometry," presented at the SPE Hydraulic Fracturing Technology Conference, Texas, SPE-179143-MS, Feb. 9-11, 2016, 18 pages.

Gomaa et al., "Improving Fracture Conductivity by Developing and Optimizing a Channels Within the Fracture Geometry: CFD Study," presented at the SPE International conference on Formation Damage Control in Layfayette, SPE-178982-MS, Feb. 24-26, 2016, 25 pages.

Gomaa et al., "New Insights Into the Viscosity of Polymer-Based In-Situ-Gelled Acids," SPE-121728-PA, Society of Petroleum Engineers, SPE Prod & Oper, Aug. 2010, 25(3):367-375, 9 pages.

Gomaa et al., "Viscoelastic Behavior and Proppant Transport Properties of a New Associative Polymer-Based Fracturing Fluid," SPE-168113-MS, Society of Petroleum Engineers, Presented at the SPE International Symposium and Exhibition on Formation Damage Control, Lafayette, Louisiana, Feb. 26-28, 2014, 17 pages.

Gomaa et al., "Viscoelastic Behavior and Proppant Transport Properties of a New High-Temperature Viscoelastic Surfactant-Based Fracturing Fluid," SPE-173745-MS, Society of Petroleum Engineers, Presented at the SPE International Symposium on Oilfield Chemistry, The Woodlands, Texas, Apr. 13-15, 2015, 25 pages.

Gomaa et al., "Viscoelastic Evaluation of a Surfactant Gel for Hydraulic Fracturing," SPE-143450-MS, Society of Petroleum Engineers, Presented at the SPE European Formation Damage Conference, Noordwijk, The Netherlands, Jun. 7-10, 2011, 18 pages.

Goodman, "Chapter 3: Rock Strength and Failure Criteria," in Introduction to Rock Mechanics, John Wiley & Sons, 1989, 21 pages.

Graves and O'Brien, "StarWars Laser Technology Applied to Drilling and Completing Gas Wells," SPE 49259, SPE Annual Technical Conference and Exhibition, Society of Petroleum Engineers, Sep. 27-30, 1998, 10 pages.

Gravsholt, "Viscoelasticity in Highly Dilute Aqueous Solutions of Pure Cationic Detergents," Journal of Colloid and Interface Science, Dec. 1976, 57(3):575-577, 3 pages.

Greenwood et al., "Evaluation and Application of Real-Time Image and Caliper Data as Part of a Wellbore Stability Monitoring Provision," IADC/SPE 9911, International Association of Drilling Contractors (IADC), Society of Petroleum Engineers (SPE), IADC/SPE Drilling Conference, Miami, Florida, Feb. 2006, 12 pages.

(56) References Cited

OTHER PUBLICATIONS

Gu and Mohanty, "Effect of Foam Quality on Effectiveness of Hydraulic Fracturing in Shales," International Journal of Rock Mechanics and Mining Sciences, 70: 273-285, 2014, 13 pages.

Gupta and Carman, "Fracturing Fluid for Extreme Temperature Conditions is Just as Easy as the Rest," SPE Hydraulic Fracturing Technology Conference, Society of Petroleum Engineers, SPE 140176-MS, Jan. 24-26, 2011, 5 pages.

Gupta et al., "Frac-Fluid Recycling and Water Conservation: A Case History," SPE-119478-PA, Society of Petroleum Engineers, SPE Prod & Oper, Feb. 2010, 25(1):65-69, 5 pages.

Gupta et al., "Surfactant Gel Foam/Emulsion: History and Field Application in the Western Canadian Sedimentary Basin," SPE-97211-MS, Society of Petroleum Engineers, Presented at the SPE Annual Technical Conference and Exhibition, Dallas, Oct. 9-12, 2005, 7 pages.

Gupta, "Unconventional Fracturing Fluids for Tight Gas Reservoirs," SPE-119424-MS, Society of Petroleum Engineers, Presented at the SPE Hydraulic Fracturing Technology Conference, The Woodlands, Texas, Jan. 19-21, 2009, 9 pages.

Gurav et al., "Silica Aerogel: Synthesis and Applications," Journal of Nanomaterials, Hindawi Publishing Corporation, 2010:409310, Jan. 1, 2010, 11 pages.

Gurluk et al., "Enhancing the Performance of Viscoelastic Surfactant Fluids Using Nanoparticles," SPE-164900-MS, Society of Petroleum Engineers, Presented at the EAGE Annual Conference and Exhibition, London, Jun. 10-13, 2013, 15 pages.

Haimson et al., "Initiation and extension of hydraulic fractures in rocks," Society of Petroleum Engineers Journal, Sep. 1967, 7(03):310-318.

Halleck and Behrmann, "Penetration of Shaped Charges in Stressed Rock," the 31st US Symposium on Rock Mechanics (USRMS), American Rock Mechanics Association, Jun. 18-20, 1990, 8 pages.

Hamley, Introduction to Soft Matter: Synthetic and Biological Self-Assembling Materials, Hoboken, New Jersey: John Wiley & Sons, 2007.

Han and Cundall, "LBM-DEM modeling of fluid-solid internation in porous media," International Journal for Numerical and Analytical Methods in Geomechanics, 37:10 (1391-1407), Jul. 2013, 17 pages.

Han et al., "Impact of Depletion on Integrity of Sand Screen in Depleted Unconsolidated Sandstone Formation," ARMA-2015-301, In 49th US Rock Mechanics/Geomechanics Symposium. American Rock Mechanics Association, 2015, 9 pages.

Han et al., "Numerical and Experimental Studies of Kerogen Rich Shales on Millimeter-Scale Single-Edge Notched Beam," ARMA-19-211, American Rock Mechanics Association (ARMA), prepared for presentation at the 53rd US Rock Mechanics and Geomechanics Symposium in New York, Jun. 23-26, 2019, 8 pages.

Han et al., "Numerical Modeling of Elastic Spherical Contact for Mohr-Coulomb Type Failures in Micro-Geomaterials," Experimental Mechanics, 2017, 57: 1091-1105, 15 pages.

Han et al., "Numerical Modeling of Thermal-Mechanical Interaction Process in Laser Heating," SPE 183836-MS, presented at the SPE Middle East Oil and Gas Show and Conference, in Manama, Kingdom of Bahrain, Mar. 6-9, 2017, 12 pages.

Han et al., "Research on the mechanical behaviour of shale based on multiscale analysis," R. Soc. Open Sci., Oct. 2018, 5: 181039, 17 pages.

Han et al., "Application of Silver-Coated Magnetic Microspheres to a SERS-Based Optofluidic Sensor," American Chemical Society Publications (ACS), the Journal of Physical Chemistry C (JPCC), 115: 6290-6296, Mar. 7, 2011, 7 pages.

Harrison et al, "Water-in-Carbon Dioxide Microemulsions with a Fluorocarbon-Hydrocarbon Hybrid Surfactant," Langmuir 1994, 10:10 (3536-3541), 6 pages.

He et al., "Hydrolysis Effect on the Properties of a New Class of Viscoelastic Surfactant-Based Acid and Damage Caused by the Hydrolysis Products," SPE-165161-MS, Society of Petroleum Engineers, Presented at the SPE European Formation Damage Conference & Exhibition, Noordwijk, The Netherlands, Jun. 5-7, 2013, 17 pages.

Helgeson et al., "Formation and Rheology of Viscoelastic "Double Networks" in Wormlike Micelle-Nanoparticle Mixtures," American Chemical Society, Langmuir, 2010, 26(11):8049-8060, 12 pages.

Heller et al., "Experimental investigation of matric permeability of gas shale," AAPG Bulletin, vol. 98, No. 5, May 2014, 21 pages.

Hiramatsu et al., "Stress around a shaft or level excavated in ground with a three-dimensional stress state," Mem Fac Eng Kyotu Univ, 1962, 24:56-76, English Abstract only, 7 pages.

Hoang et al., "Correspondence Principle Between Anisotropic Poroviscoelasticity and Poroelasticity using Micromechanics and Application to Compression of Orthotropic Rectangular Strips," Journal of Applied Physics, American Institute of Physics, 112: 044907, Aug. 30, 2012, 16 pages.

Hoek and Brown, "Empirical Strength Criterion for Rock Masses," Journal of the Geotechnical Engineering Division, Sep. 1980, 20 pages.

Hornby et al., "Anisotropic Effective-Medium Modeling of the Elastic Properties of Shales," Geophysics, 59:10 (1570-1583), Oct. 1994, 14 pages.

Hosemann et al., "An Exploratory Study to Determine Applicability of Nano-Hardness and Micro-compression Measurements for Yield Stress Estimation," Science Direct, Journal of Nuclear Materials, 375: 135-143, 2008, 9 pages.

Hosemann et al., "Mechanical Characteristics of SiC Coating Layer in TRISO Fuel Particles," Journal of Nuclear Materials, 442: 133-142, 2013, 10 pages.

Hu et al., "Smart Liquid SERS Substrates based on $Fe_3O_4$/Au Nanoparticles with Reversibility Tunable Enhancement Factor for Practical Quantitative Detection," a natureresearch journal, Scientific Reports, 4:7204, Nov. 27, 2014, 10 pages.

Huang et al., "A theoretical study of the critical external pressure for casing collapse" Journal of Natural Gas Science and Engineering, Nov. 2015, 27(1), 8 pages.

Huang et al., "Collapse strength analysis of casing design using finite element method," International Journal of Pressure Vessels and Piping 2000, 77:359-367, 8 pages.

Huang et al., "Do Viscoelastic-Surfactant Diverting Fluids for Acid Treatments Need Internal Breakers?" SPE-112484-MS, Society of Petroleum Engineers (SPE), presented at the SPE International Symposium and Exhibition on Formation Damage Control, Lafayette, Louisiana, Feb. 13-15, 2008, 8 pages.

Huang et al., "Field Case Study on Formation Fines Control with Nanoparticles in Offshore Wells," SPE-135088-MS, Society of Petroleum Engineers (SPE), presented at the SPE Annual Technical Conference and Exhibition, Florence, Italy, Sep. 19-22, 2010, 8 pages.

Huang et al., "Fluid-Loss Control Improves Performance of Viscoelastic Surfactant Fluids," SPE-106227-PA, Society of Petroleum Engineers (SPE), SPE Production and Operations, Feb. 2009, 24:1 (60-65), 6 pages.

Huang et al., "Improving Fracture Fluid Performance and Controlling Formation Fines Migration with the Same Agent: Is It Achievable?" IPTC-17044-MS, International Petroleum Technology Conference, Presented at the International Petroleum Technology Conference, Beijing, Mar. 26-28, 2013, 8 pages.

Huang et al., "Nanoparticle Pseudocrosslinked Micellar Fluids: Optimal Solution for Fluid-Loss Control With Internal Breaking," SPE-128067-MS, Society of Petroleum Engineers (SPE), presented at the SPE International Symposium and Exhibition on Formation Damage Control, Lafayette, Louisiana, Feb. 10-12, 2010, 8 pages.

Huang et al., "Nanotechnology Applications in Viscoelastic-Surfactant Stimulation Fluids," SPE-107728-PA, Society of Petroleum Engineers (SPE), SPE Production and Operations, Nov. 2008, 23:4 (512-517), 6 pages.

Hubbert et al., "Mechanics of hydraulic fracturing," Transactions of the AIME, Dec. 1957, 210(01):153-168.

Hull and Abousleiman, "Chapter 10: Insights of the Rev of Source Shale from Nano-and Micromechanics," in New Frontiers in Oil and Gas Exploration, Springer International Publishing Switzerland, 2016, 29 pages.

(56) References Cited

OTHER PUBLICATIONS

Hull et al., "Bromate Oxidation of Ammonium Salts: In Situ Acid Formation for Reservoir Stimulation," Inorganic Chemistry, 2019, 58, 3007-3014, 8 pages.
Hull et al., "Nanomechanical Characterization of the Tensile Modulus of Rupture of Kerogen-Rich Shale," SPE 177628, Society of Petroleum Engineers (SPE), presented at the Abu Dhabi International Petroleum Exhibition and Conference, Nov. 9-12, 2015, SPE Journal 2017, 22:4 (1024-1033), 10 pages.
Hull et al., "New Insights on the Mechanical Characterization of Kerogen-Rich Shale, KRS," SPE-177628-MS, Society of Petroleum Engineers (SPE), presented at the Abu Dhabi International Petroleum Exhibition and Conference held in Abu Dhabi, Nov. 9-12, 2015, UAE, 12 pages.
Hull et al., "Oxidative Kerogen Degradation: A Potential Approach to Hydraulic Fracturing in Unconventionals," Energy Fuels 2019, 33:6 (4758-4766), 9 pages.
Hull et al., "Recent Advances in Viscoelastic Surfactants for improved Production from Hydrocarbon Reservoirs," SPE 173776, Society of Petroleum Engineers (SPE), presented at the SPE International Symposium on Oilfield Chemistry, Apr. 13-15, 2015, SPE Journal, 2016, 18 pages.
Hunt et al., "Kinetics of the gelation of colloidal silica at geothermal conditions and implications for reservoir modification and management," SGP-TR-198, proceedings of the Thirty-Eighth Workshop on Geothermal Reservoir Engineering, Jan. 2013, 10 pages.
Huseby et al., "High Quality Flow Information from Tracer Data," SPE-169183-MS, Society of Petroleum Engineers (SPE), presented at the SPE Bergen One Day Seminar, Apr. 2, 2014, 9 pages.
Hutchins et al., "Aqueous Tracers for Oilfield Applications," SPE-21049, Society of Petroleum Engineers (SPE), presented at SPE International Symposium on Oilfield Chemistry, Feb. 20-22, 1991, 9 pages.
Imanishi et al., "Wormlike Micelles of Polyoxyethylene Alkyl Ether Mixtures C10E5 + C14E5 and C14E5 + C14E7: Hydrophobic and Hydrophilic Chain Length Dependence of the Micellar Characteristics," Journal of Physical Chemistry B, 2007, 111:1 (62-73), 12 pages.
Infante and Chenevert, "Stability of boreholes drilled through salt formations displaying plastic behaviour," SPE Drilling Engineering, 4:1, Mar. 1989, 9 pages.
Iqbal et al., "In situ micro-cantilver tests to study fracture properties of NiAl single crystals," Acta Materialia, 60(3):1193-1200, Feb. 2012, 8 pages.
Israelachvili et al., "Theory of Self-Assembly of Hydrocarbon Amphiphiles into Micelles and Bilayers," Journal of Chemical Society, Faraday Transactions, 1976, 2:72 (1525-1567), 44 pages.
Itasca, "Fast Lagrangian Analysis of Continua," Version 7.0. Minneapolis, Minnesota, 2011, 22 pages.
itascacg.com [online], "Particle Flow Code, Version 5.0," Itasca Consulting Group, Inc., available on or before Apr. 11, 2014, [retrieved on May 11, 2018], retrieved from URL: <https://www.itascacg.com/software/pfc>, 5 pages.
itascacg.com [online], "Three-dimensional Fast Lagrangian Analysis of Continua (FLAC3D)," available on or before 2012, [retrieved on Jun. 7, 2018], retrieved from URL: <https://www.itascacg.com/software/flac3d>, 4 pages.
Iyengar et al., "Analysis of Crack Propagation in Strain-Softening Beams," Engineering Fracture Mechanics 69: 761-778, 2002, 18 pages.
Jaeger et al., "Fundamentals of Rock Mechanics," 4th Edition, Wiley, 2007, 486 pages.
Jerath et al., "Improved assessment of in-situ fluid saturation with multi-dimensional NMR measurements and conventional well logs," SPWLA 53rd Annual Logging Symposium, Jun. 16-20, 2012, 16 pages.
Jerke et al., "Flexibility of Charged and Uncharged Polymer-Like Micelles," Langmuir 1998, 14:21 (6013-6024), 12 pages.

Jia et al., "Highly Efficient Extraction of Sulfate Ions with a Tripodal Hexaurea Receptor," Angew. Chem. Int. Ed., 2011, 50: 486-490, 5 pages.
Jianhong et al., "Estimation of the Tensile Elastic Modulus using Brazilian disc by Applying Diametrically Opposed Concentrated Loads," International Journal of Rock Mechanics & Mining Sciences 46:3 (568-576), 2009, 9 pages.
Jiantaol and Bingcheng, "Development of Silica Aerogel and Hollow Glass Microspheres Based Heat-Insulating Coatings," Paint & Coatings Industry, Jul. 1, 2013, 1 page, abstract only.
Jin et al., "Permeability Measurement of Organic-Rich Shale—Comparison of Various Unsteady-State Methods" SPE-175105-MS, Society of Petroleum Engineers, Sep. 2015, 14 pages.
Johnston et al, "Water-in-Carbon Dioxide Microemulsions: An Environment for Hydrophiles Including Proteins," Science, 271:5249 (624-626), Feb. 2, 1996, 3 pages.
Jones, "A Technique for Faster Pulse-Decay Permeability Measurements in Tight Rocks," presented at the 1994 SPE Annual Technical Conference and Exhibition, Sep. 25-28, 1994, SPE Formation Evaluation, Mar. 1997, 7 pages.
Jose et al., "Continuous multi cycle nanoindentation studies on compositionally graded $Ti_{1-x}Al_xN$ multilayer thin films," Materials Science and Engineering A, 528:21 (6438-6444), Apr. 20, 2011, 7 pages.
Jun et al., "Multifunctional Silver-Embedded Magnetic Nanoparticles as SERS Nanoprobes and Their Applications," Nano Micro Small, Multifunctional Nanoparticles, 6:1 (119-125), Jan. 4, 2010, 7 pages.
Kang et al., "An experimental study on oxidizer treatment used to improve the seepage capacity of coal reservoirs," Natural Gas Industry B, 6: 129-137, Sep. 25, 2018, 9 pages.
Keivani et al., "Synergistic Toughening in Ternary Silica/Hallow Glass Spheres/Epoxy Nanocomposites," Polymer-Plastics Technology and Engineering, Dec. 10, 2014, 54:6 (581-593), 14 pages.
Kelemen et al., "Petroleum Expulsion Part 2. Organic Matter Type and Maturity Effects on Kerogen Swelling by Solvents and Thermodynamic Parameters for Kerogen from Regular Solution Theory," Energy & Fuels 20: 310-308, 2006, 8 pages.
Kenyon, "Petrophysical Principles of Applications of NMR Logging," Society of Petrophyicists and Well-Log Analysts, 38:2, Mar. 1997, 23 pages.
Kern et al., "Propping Fractures with Aluminum Particles," Journal of Petroleum Technology, vol. 13, Issue 6, pp. 583-589, SPE-1573-G-PA, Jun. 1961, 7 pages.
Kethireddy, "Quantifying the effect of kerogen on Electrical Resistivity Measurements in Organic Rich Source Rocks," Thesis in partial fulfillment of the requirements for the degree of Master of Science, Dec. 2013, 78 pages.
Kim et al., "Numerical analysis of fracture propagation during hydraulic fracturing operations in shale gas systems," International Journal of Rock and Mechanics Mining Sciences, 76: 127-137, 2015, 11 pages.
King, "Thirty Years of Gas Shale Fracturing: What Have We Learned?" SPE-133456, Society of Petroleum Engineers (SPE), presented at the SPE Annual Technical Conference and Exhibition, Sep. 19-22, 2010, 50 pages.
Klapetek, "Chapter 11: Thermal Measurements," in Quantitative Data Processing in Scanning Probe Microscopy: SPM Applications for Nanometrology, 2018, 26 pages.
Kneipp et al., "Single Molecule Detection Using Surface-Enhanced Raman Scattering (SERS)," Physical Review Letters, American Physical Society 78:9, Mar. 3, 1997, 4 pages.
Kolymbas, "Kinematics of Shear Bands," Acta Geotechnica, 4: 315-318, 2009, 4 pages.
Kotai et al., "Beliefs and Facts in Permanganate Chemistry—An Overview on the Synthesis and the Reactivity of Simple and Complex Permanganates," Trends in Inorganic Chemistry, 2009, 11 pages.
Kreh, "Viscoelastic Surfactant-Based Systems in the Niagaran Formation," SPE-125754-MS, Society of Petroleum Engineers (SPE), presented at the SPE Eastern Regional Meeting, Charleston, West Virginia, Sep. 23-25, 2009, 7 pages.

(56) References Cited

OTHER PUBLICATIONS

Kumar et al., "Nano to Macro Mechanical Characterization of Shale," SPE 159804, Society of Petroleum Engineers (SPE), presented at the SPE Annual Technical Conference and Exhibition, Oct. 8-10, 2012, 23 pages.
Kuperkar et al., "Viscoelastic Micellar Water/CTAB/NaNO3 Solutions: Rheology, SANS and Cryo-TEM Analysis," Journal of Colloid and Interface Science, 2008, 323:2 (403-409), 7 pages.
Lai et al., "Experimental Investigation on Brazilian Tensile Strength of Organic-rich Gas Shale," SPE-177644-MS, Society of Petroleum Engineers (SPE), presented at the Abu Dhabi International Petroleum Exhibition and Conference, Nov. 9-12, 2015, 24 pages.
Lam et al., "Experiments and Theory in Strain Gradient Elasticity," Journal of Mechanics and Physics of Solids, 51: 1477-1508, 2003, 32 pages.
Larsen et al., "Changes in the Cross-Link Density of Paris Basin Toarcian Kerogen During Maturation," Organic Geochemistry 33: 1143-1152, 2002, 10 pages.
Lee et al., "An Analytical Study on Casing Design for Stabilization of Geothermal Well," Korean J. Air-Conditioning and Ref. Eng., 2012, 11:24 (11), 16 pages (English Abstract).
Lee et al., "Water-in carbon dioxide emulsions: Formation and stability," Langmuir, 1999, 15:20 (6781-6791), 11 pages.
Leitzell, "Viscoelastic Surfactants: A New Horizon in Fracturing Fluids for Pennsylvania," SPE-111182-MS, Society of Petroleum Engineers (SPE), presented at the Eastern Regional Meeting, Lexington, Kentucky, Oct. 17-19, 2007, 6 pages.
Lewan, "Evaluation of petroleum generation by hydrous pyrolysis experimentation," Phil. Trans. R. Soc. Lond. A, 1985, 315: 123-134, 13 pages.
Lewan, "Experiments on the role of water in petroleum formation," Geochimica et Cosmochimica Acta, Pergamon, 1997, 61:17 (3691-3723), 33 pages.
Li et al., "A review of crosslinked fracturing fluids prepared with produced water," KeAi Advanced Research Evolving Science, Southwest Petroleum University, Petroleum 2, 2:4 (313-323), Dec. 2016, 11 pages.
Li et al., "Differentiating Open Natural Fractures from Healed Fractures Using the New, High-Definition Oil-Based Mud Microelectrical Imager-Case Studies from Organic Rich Shales," SPE-174923-MS, Society of Petroleum Engineers (SPE), presented at the SPE Annual Technical Conference and Exhibition, Sep. 28-30, 2015, 16 pages.
Li et al., "High-Temperature Fracturing Fluids Using Produced Water with Extremely High TDS and Hardness," IPTC-17797-MS, International Petroleum Technology Conference (IPTC), presented at the International Petroleum Technology Conference, Dec. 10-12, 2014, 13 pages.
Li et al., "Maximum Horizontal Stress and Wellbore Stability While Drilling: Modeling and Case Study," SPE 139280, Society of Petroleum Engineers (SPE), presented at the SPE Latin American & Caribbean Petroleum Enginering Conference, Dec. 2010, 11 pages.
Li et al., "Mechanical Characterization of Micro/Nanoscale Structures for MEMS/NEMS Applications using Nanoindentation Techniques," Science Direct, Ultramicroscopy, 97: 481-494, 2003, 14 pages.
Li et al., "The Brazilian Disc Test for Rock Mechanics Applications: Review and New Insights," Rock Mech Rock Eng, 2013, 46: 269-287, 19 pages.
Li et al., "Well Treatment Fluids Prepared With Oilfield Produced Water: Part II," SPE-133379-MS, Society of Petroleum Engineers (SPE), presented at the SPE Annual Technical Conference and Exhibition, Sep. 19-22, 2010, 7 pages.
Liang et al., "An Experimental Study on Interactions between Imbibed Fracturing Fluid and Organic-Rich Tight Carbonate Source Rocks" SPE-188338-MS, Paper presented at the Abu Dhabi International Petroleum Exhibition & Conference, Nov. 2017, 14 pages.
Liu and Abousleiman, "Multiporosity/Multipermeability Inclined-Wellbore Solutions with Mudcake Effects," Society of Petroleum Engineers (SPE), SPE Journal 23:5, Oct. 2018, 25 pages.
Liu and Abousleiman, "N-Porosity and N-Permeability generalized wellbore stability analytical solutions and applications," ARMA 16-417, America Rock Mechanics Association (ARMA), presented at the 50th US Rock Mechanics/Geomechanics Symposium held in Houston, Texas, Jun. 26-29, 2016, 10 pages.
Liu et al., "Applications of nano-indentation methods to estimate nanoscale mechanical properties of shale reservoir rocks," Journal of Natural Gas Science and Engineering, 35: 1310-1319, Sep. 29, 2016, 10 pages.
Liu et al., "Microstructural and geomechanical analysis of Bakken shale at nanoscale," Journal of Petroleum Science and Engineering, 153: 138-144, Mar. 23, 2017, 12 pages.
Liu et al., "Numerical modelling of the heterogeneous rock fracture process using various test techniques." Rock mechanics and rock engineering 40.2, Jun. 2006, 107-144, 38 pages.
Liu et al., "Poroelastic Dual-Porosity/Dual-Permeability After-Closure Pressure-Curves Analysis in Hydraulic Fracturing," SPE 181748, Society of Petroleum Engineers (SPE), SPE Journal 2016, 21 pages.
Liu et al., "Safe Drilling in Chemically Active and Naturally Fractured Source Rocks: Analytical Solution and Case Study," IADC/SPE-189658-MS, Society of Petroleum Engineers (SPE), IADC, presented at the IADC/SPE Drilling Conference and Exhibition, Mar. 6-8, 2018, 13 pages.
Liu et al., "Graphene Lubricant," Applied Materials Today, Sep. 20, 2020, 100662, 31 pages.
Liu, "Dimension effect on mechanical behavior of silicon microcantilver beams," Measurement, 41:8 (885-895), Oct. 2008, 11 pages.
Liu, "Elastic Constants Determination and Deformation Observation Using Brazilian Disk Geometry," Experimental Mechanics, 2010, 50: 1025-1039, 15 pages.
Liu, "Fracture Toughness Assessment of Shales by Nanoindentation," Thesis for the degree of Master of Science in Civil Engineering, Geotechnical Engineering Masters Projects, University of Massachusetts Amherst, Sep. 2015, 80 pages.
Liu, "Micro-cantilver Testing to Evaluate the Mechanical Properties of Thermal Barrier Coatings," presented at the 19th European Conference on Fracture (ECF19): Fracture Mechanics for Durability, Reliability and Safety, Conference Proceedings, Aug. 26-31, 2012, 7 pages.
Long et al., "Chapter 2: Advanced Well Stimulation Technologies," in An Independent Scientific Assessment of Well Stimulation in California, vol. I, Well Stimulation Technologies and their Past, Present and Potential Future Use in California, Jan. 2015, 62 pages.
Low, "Advances in Ceramics Matrix Composites," Processing. Properties and applications of SiC1/SiC, 10-19, Nanoceramic Matric Composites, 30-41, 2014, 11 pages.
Low, "Ceramic-Matrix Composites: Microstructure, Properties and Applications," Woodhead Publishing Limited, 11-19, 30-40, 2006, 11 pages.
Lu et al, "Fabrication and characterization of ceramic coatings with alumina-silica sol-incorporated a-alumina powder coated on woven quartz fiber fabrics," Ceramics International 39:6 (6041-6050), Aug. 2013, 10 pages.
Lu et al., "Quantitative prediction of seismic rock physics of hybrid tight oil reservoirs of the Permian Lucaogou Formation, Junggar Basin, Northwest China," Journal of Asian Earth Sciences, 2019, 178: 216-223, 8 pages.
Luan et al., "Creation of synthetic samples for physical modelling of natural shale," European Association of Geoscientists and Engineers (EAGE), Geophysical Prospecting 64: 898-914, Jul. 2016, 17 pages.
Luffel et al., "Matrix permeability measurement of gas productive shales," SPE-26633-MS, Society of Petroleum Engineers (SPE), presented at the 66th Annual Technical Conference and Exhibition, Oct. 3-6, 1993, 10 pages.
Lungwitz et al., "Diversion and Cleanup Studies of Viscoelastic Surfactant-Based Self-Diverting Acid," SPE-86504-PA, Society of Petroleum Engineers (SPE), SPE Production and Operations, 2007, 22:1 (121-127), 7 pages.

(56) References Cited

OTHER PUBLICATIONS

Luo et al., 2012. "Rheological Behavior and Microstructure of an Anionic Surfactant Micelle Solution with Pyroelectric Nanoparticle," Colloid and Surface A: Physiochemical English Aspects, Feb. 5, 2012, 395: 267-275, 9 pages.

Lv et al., "Experimental and numerical study of crack behavior for capsule-based self-healing cennentitious materials," Construction and Building Materials, 2017, 219-229, 11 pages.

Lyngra et al., "Heavy Oil Characterization: Lessons Learned During Placement of a Horizontal Injector at a Tar/Oil Interface," SPE-172673-MS, Society of Petroleum Engineers (SPE), presented at the SPE Middle East Oil & Gas Show and Conference, Mar. 8-11, 2015, 20 pages.

Lynn et al., "A Core Based Comparison Of The Reaction Characteristics Of Emulsified And In-Situ Gelled Acids In Low Permeability, High Temperature, Gas Bearing Carbonates," SPE-65386-MS, Society of Petroleum Engineers (SPE), presented at the SPE International Symposium on Oilfield Chemistry, Houston, Feb. 13-16, 2001, 16 pages.

Magryta, "Effect of Aerogel on the Properties of Acrylonitrile-butadiene rubber (NBR) Vulcanizates," Polimer, 57:2, Feb. 1, 2012, 7 pages, English summary.

Mahabadi et al., "A novel approach for micro-scale characterization and modeling of geomaterials incorporating actual material heterogeneity," (XP002689941) Geophysical Research Letters 39:1 (L01303), Jan. 1, 2012, 6 pages.

Mahabadi et al., "Development of a new fully-parallel finite-discrete element code: Irazu," ARMA-2016-516, American Rock Mechanics Association (ARMA), presented at the 50th US Rock Mechanics/Geomechanics Symposium, Jun. 26-29, 2016, 9 pages.

Mahmoud et al., "Removal of Pyrite and Different Types of Iron Sulfide Scales in Oil and Gas Wells without H2S Generation," IPTC-18279-MS, International Petroleum Technology Conferences (IPTC), presented at the International Petroleum Technology Conference, Dec. 6-9, 2015, 8 pages.

Maia et al., "Triaxial creep tests in salt applied in drilling through thick salt layers in Campos basin—Brazil," SPE/IADC Drilling Conference. OnePetro, Feb. 2005, 9 pages.

Maio et al., "Measuring Fracture Toughness of Coatings using Focused-ion-beam-machined Microbeams," J. Mater. Res., 20:2, Feb. 2005, 4 pages.

Maleki et al., "An overview on silica aerogels synthesis and different mechanical reinforcing strategies," Journal of Non-Crystalline Solids, 385: 55-74, Feb. 1, 2014, 20 pages.

Mao et al., "Chemical and nanometer-scale structure of kerogen and its change during thermal maturation investigated by advanced solid-state 13C NMR spectroscopy," Geochimica et Cosmochimica Acta, 2010, 74(7): 2110-2127, 18 pages.

Marchetti et al., "Fluorous affinity chromatography for enrichment and determination of perfluoroalkyl substances," American Chemical Society (ACS), Annual Review of Analytical Chemistry 84: 7138-7145, Jul. 19, 2012, 8 pages.

MatWeb, "Chlorinated Polyethylene Data Sheet," 2021, 1 page.

Maurer, "Novel Drilling Techniques," New York: Pergamon Press, V114, 1968, 130 pages.

Mavko et al., "The rock physics handbook: Cambridge Univ. Press.," Cambridge University Press, Oct. 2003, 1 page, Abstract Only.

Maxwell, "Microseismic hydraulic fracture imaging: The path toward optimizing shale gas production," The Leading Edge, Special Section: Shales, Mar. 2011, 6 pages.

Mayerhofer al., "Proppants? We Don't Need No Proppants", Presented at the SPE Annual Technical Conference and Exhibition, San Antonio TX; Society of Petroleum Engineers, Inc, pp. 457-464, Paper SPE-38611, Oct. 5, 1997, 8 pages.

McElfresh et al., "A Single Additive Non-Ionic System for Frac Packing Offers Operators a Small Equipment Footprint and High Compatibility with Brines and Crude Oils," SPE-82245-MS, Society of Petroleum Engineers (SPE), presented at the SPE European Formation Damage Conference, The Hague, The Netherlands, May 13-14, 2003, 11 pages.

McMahon et al., "First 100% Reuse of Bakken Produced Water in Hybrid Treatments Using Inexpensive Polysaccharide Gelling Agents," SPE-173783-MS, Apr. 2015, 9 pages.

Mehrabian and Abousleiman, "Generalized Biot's Theory an Mandel's Problem of Multiple Porosity and Multiple-Permeability Poroelasticity," American Geophysical Union (AGU), Journal of Geological Research: Solid Earth, 119:4 (2745-2763), 2014, 19 pages.

Mesa, "Spherical and rounded cone nano indenters," Micro Star Technologies Inc., available on or before Jan. 23, 2018, 24 pages.

metarocklab.com [online], "Pumps," 2019, retrieved Oct. 13, 2021 from URL<https://www.metarocklab.com/product-page/pressure-generators>, 2 pages.

Meyer et al., "Identification of Source Rocks on Wireline Logs by Density/Resistivity and Sonic Transit Time/Resistivity Crossplots," AAPG Bulletin, 1984, 68(2): 121-129, 9 pages.

Meyer et al., "Theoretical Foundation and Design Formulae for Channel and Pillar Type Propped Fractures—A Method to Increase Fracture Conductivity," presented at SPE Annual Technical Conference and Exhibition, Amsterdam, The Netherlands, SPE-170781-MS, Oct. 27-29, 2014, 25 pages.

Meyers et al., "Point load testing of drill cuttings from the determination of rock strength," ARMA-05-712, presented at the 40th U.S. Symposium on Rock Mechanics (USRMS), Alaska Rocks 2005, American Rock Mechanics Association, Jun. 25-29, 2005, 2 pages, (Abstract).

Middleton et al, "Shale gas and non-aqueous fracturing fluids: Opportunities and challenges for supercritical CO 2," Applied Energy, 147: 500-509, 2015, 10 pages.

Mitchell et al., "Chapter 7: Casing and Tubing Design," Properties of Casing and Tubing, Petroleum well construction, 1998, 40 pages.

Mohammed et al., "Casing structural integrity and failure modes in a range of well types—A review," Journal of Natural Gas Science and Engineering, 2019, 68: 102898, 25 pages.

Mohammed et al., "Successful Application of Foamed Viscoelastic Surfactant-Based Acid," SPE-95006-MS, Society of Petroleum Engineers (SPE), presented at the SPE European Formation Damage Conference, Sheveningen, The Netherlands, May 25-27, 2005, 7 pages.

Montgomery and Smith, "Hydraulic Fracturing: History of Enduring Technology," Journal of Petroleum Technology, Dec. 2010, 7 pages.

Montgomery, "Chapter 1: Fracturing Fluids," in Effective and Sustainable Hydraulic Fracturing, Intech, the proceedings of the International Conference for Effective and Sustainable Hydraulic Fracturing (HF2103) on May 20-22, 2013, 23 pages.

Montgomery, "Chapter 2: Fracturing Fluid Components," in Effective and Sustainable Hydraulic Fracturing, Intech, 2013, 21 pages.

Moyer, "A Case for Molecular Recognition in Nuclear Separations: Sulfate Separation from Nuclear Wastes," American Chemical Society (ACS), Inorganic Chemistry, 2012, 52: 3473-3490, 18 pages.

Moyner et al., "The Application of Flow Diagnostics for Reservoir Management," SPE 171557, Society of Petroleum Engineers (SPE), SPE Journal, Apr. 2015, 18 pages.

Mutua et al., "Surface Modification of Hollow Glass Microspheres," Materials Sciences and Applications, 3:856-860, Dec. 2012, 5 pages.

Nagarajan, "Molecular Packing Parameter and Surfactant Self-Assembly: The Neglected Role of the Surfactant Tail," Langmuir 2002, 18:1 (18-38), 8 pages.

Najm et al., "Comparison and Applications of Three Different Maximum Horizontal Stress Predictions," SPWLA 61st Annual Logging Symposium, Jun. 2020, 11 pages.

Nasr-El-Din et al., "Investigation and Field Evaluation of Foamed Viscoelastic Surfactant Diversion Fluid Applied During Coiled-Tubing Matrix-Acid Treatment," SPE-99651-MS, Society of Petroleum Engineers (SPE), presented at the SPE/ICoTA Coiled Tubing Conference & Exhibition, The Woodlands, Texas, Apr. 4-5, 2006, 14 pages.

(56) References Cited

OTHER PUBLICATIONS

Nasr-El-Din et al., "Lessons Learned and Guidelines for Matrix Acidizing With Viscoelastic Surfactant Diversion in Carbonate Formations," SPE-102468-MS, Society of Petroleum Engineers (SPE), presented at the SPE Annual Technical Conference and Exhibition, San Antonio, Texas, Sep. 24-27, 2006, 11 pages.
Nehmer, "Viscoelastic Gravel-Pack Carrier Fluid," SPE-17168-MS, Society of Petroleum Engineers (SPE), presented at the SPE Formation Damage Control Symposium, Bakersfield, California, Feb. 8-9, 1988, 10 pages.
Nettesheim et al., "Influence of Nanoparticle Addition on the Properties of Wormlike Micellar Solutions," Langmuir 2008, 24:15 (7718-7726), 9 pages.
Nguyen and Abousleiman, "Poromechanics Response of Inclined Wellbore Geometry in Chemically Active Fractured Porous Media," Journal of Engineering Mechanics, 135:11, Nov. 2005, 14 pages.
Ning et al., "The measurement of Matrix and Fracture Properties in Naturally Fractured Cores," SPE-25898, Society of Petroleum Engineers (SPE), presented at the SPE Rocky Mountain Regional/Low Permeability Reservoirs Symposium, Apr. 26-28, 1993, 15 pages.
Norman et al., "Temperature-Stable Acid-Gelling Polymers: Laboratory Evaluation and Field Results," SPE-10260-PA, J Pet Technol, Nov. 1984, 36(11): 2011-2018.
Nwonodi et al., "A Scheme for Estimating the Magnitude of the Maximum Horizontal Stress for Geomechanical Studies," SPE 203731-MS, Society of Petroleum Engineers (SPE), presented at the Nigeria Annual International Conference and Exhibition, Aug. 2020, 10 pages.
Okiongbo et al., "Changes in Type II Kerogen Density as a Function of Maturity: Evidence from the Kimmeridge Clay Formation," Energy Fuels, 2005, 19: 2495-2499, 5 pages.
Oliver and Pharr, "An improved technique for determining hardness and elastic modulus using load and displacement sensing indentation experiments," Journal of Materials Research, Jun. 1992, 7(6): 1564-1583, 20 pages.
Oliver and Pharr, "Measurement of hardness and elastic modulus by instrumented indentation: Advances in understanding and refinements to methodology," Journal of Materials Research, 19:1, Jan. 2004, 18 pages.
Ortega et al., "The Effect of Particle Shape and Grain-Scale Properties of Shale: A Micromechanics Approach," International Journal for Numerical and Analytical Methods in Geomechanics, 34: 1124-1156, 2010, 33 pages.
Ortega et al., "The Effect of the Nanogranular Nature of Shale on their Poroelastic Behavior," Acta Geotechnica, 2: 155-182, 2007, 28 pages.
Ortega et al., "The Nanogranular Acoustic Signature of Shale," Geophysics, 74:3 (D65-D84), May-Jun. 2009, 20 pages.
Osman and Pao, "Mud Weight Prediction for Offshore Drilling," 8 pages.
Ottesen, "Wellbore Stability in Fractured Rock," IADC/SPE 128728, International Association of Drilling Contractors (IADC), Society of Petroleum Engineers (SPE), presented at the 2010 IADC/SPE Drilling Conference and Exhibition, Louisiana, Feb. 2-4, 2010, 8 pages.
Pakdaman et al., "Experimental and numerical investigation into the methods of determination of mode I static fracture toughness of rocks." Theoretical and Applied Fracture Mechanics 100, Jan. 2019, 154-170, 17 pages.
Palisch et al., "Determining Realistic Fracture Conductivity and Understanding Its Impact on Well Performance—Theory and Field Examples," SPE-106301-MS, Society of Petroleum Engineers (SPE), presented at the SPE Hydraulic Fracturing Technology Conference, College Station, Texas, Jan. 29-31, 2007, 13 pages.
Pandey et al., "Fracture Stimulation Utilizing a Viscoelastic-Surfactant Based System in the Morrow Sands in Southeast New Mexico," SPE-102677-MS, Society of Petroleum Engineers (SPE), presented at the International Symposium on Oilfield Chemistry, Houston, Feb. 28-Mar. 2, 2007, 8 pages.
Pant, "Nanoindentation characterization of clay minerals and clay-based hybrid bio-geomaterials," dissertation for degree of Doctor of Philosophy in the Department of Civil and Environmental Engineering at the Louisiana State University and Agricultural and Medical College, Dec. 2013, 111 pages.
Parker et al., "Laser Drilling: Effects of Beam Application Methods of Improving Rock Removal," SPE 84353, SPE Annual Technical Conference and Exhibition, Society of Petroleum Engineers, Oct. 5-8, 2003, 7 pages.
paroscientific.com [online], "Overview & product selection guide," no date, retrieved Oct. 13, 2021 from URL<http://paroscientific.com/products.php>, 2 pages.
Passey et al., "From Oil-Prone Source Rock to Gas-Producing Shale Reservoir—Geologic and Petrophysical Characterization of Unconventional Shale-Gas Reservoirs," SPE 131350, Society of Petroleum Engineers (SPE), presented at the CPS/SPE International Oil & Gas Conference and Exhibition, Jun. 8-10, 2010, 29 pages.
Patel et al., "Analysis of US Hydraulic Fracturing Fluid System and Proppant Trends," SPE 168645, Society of Petroleum Engineers (SPE), presented at the SPE Hydraulic Fracturing Technology Conference, Feb. 4-6, 2014, 20 pages.
Petoud et al., "Brilliant SM, Eu, Tb, and Dy Chiral Lanthanide Complexes with Strong Circularly Polarized Luminescence," Journal for the American Chemical Society (JACS), 129: 77-83, Dec. 15, 2006, 7 pages.
petrowiki.org [online], "Fluid flow in naturally fractured reservoirs," retrieved from URL <https://petrowiki.org/Fluid_flow_in_naturally_fractured_reservoirs>, available on or before Jul. 16, 2015, retrieved on Nov. 11, 2019, 12 pages.
Podio et al., "Dynamic Properties of Dry and Water-Saturated Green River Shale under Stress," SPE 1825, Society of Petroleum Engineers (SPE), presented at the SPE 42nd Annual Fall Meeting, Oct. 1-4, 1967, Society of Petroleum Engineers Journal, Jun. 11, 1968, 16 pages.
Pojanavaraphan et al., "Solution Cross-Linked Natural Rubber (NR)/Clay Aerogel Composites," Macromolecules, Feb. 22, 2011, 44:4 (923-931), 9 pages.
Pollard et al., "Fundamentals of Structural Geology," Cambridge University Press, Sep. 1, 2005, 291, 3 pages.
Pollock and Hammiche, "Micro-thermal analysis: techniques and applications," Journal of Physics D: Applied Physics, 34.9 (R23-R53), 2001, 31 pages.
Poon et al., "An Analysis of Nanoindentation in Linearly Elastic Solids," International Journal of Solids and Structures, 45:24 (6018-6033), Dec. 1, 2008, 16 pages.
Qin et al, "Applicability of nonionic surfactant alkyl polyglucoside in preparation of liquid CO2 emulsion," Journal of CO2 Utilization, 2018, 26: 503-510, 8 pages.
Raghavan et al., "Highly Viscoelastic Wormlike Micellar Solutions Formed by Cationic Surfactants with Long Unsaturated Tails," Langmuir 2001, 17:2 (300-306), 7 pages.
Rajbanshi et al., "Sulfate Separation from Aqueous Alkaline Solutions by Selective Crystallization of Alkali Metal Coordination Capsules," American Chemical Society Publications (ACS), Crystal Growth and Design, 2011, 11: 2702-2706, 5 pages.
Rawat et al., "Case Evaluating Acid Stimulated Multilayered Well Performance in Offshore Carbonate Reservoir: Bombay High," OTC-25018-MS, Offshore Technology Conference (OTC), presented at the Offshore Technology Conference—Asia, Kuala Lumpur, Mar. 25-28, 2014.
ResTech, "Development of laboratory and petrophysical techniques for evaluating shale reservoirs," GRI-95/0496, Gas Research Institute, Apr. 1996, 306 pages.
Ribeiro and Sharma, "Fluid Selection for Energized Fracture Treatments," SPE 163867, Society of Petroleum Engineers (SPE), presented at the SPE Hydraulic Fracturing Technology Conference, Feb. 4-6, 2013, 11 pages.
Richard et al, "Slow Relaxation and Compaction of Granular Systems," Nature Materials, Feb. 4, 2005, 8 pages.
Rodriguez et al., "Imagining techniques for analyzing shale pores and minerals," National Energy Technology Laboratory, Dec. 2, 2014, 44 pages.

(56) References Cited

OTHER PUBLICATIONS

Rostami et al., "DABCO tribromide immobilized on magnetic nanoparticle as a recyclable catalyst for the chemoselective oxidation of sulfide using H2O2 under metal and solvent-free condition," Catal. Commun. 2014, 43: 16-20, 20 pages.
Rotaru et al., "Performances of clay aerogel polymer composites for oil spill sorption: Experimental design and modeling," Separation and Purification Technology, Jul. 11, 2014, 133:260-275, 16 pages.
Rowan et al., "Dynamic Covalent Chemistry," Angewante Chemie International Edition, 41: 898-952, Mar. 15, 2002, 55 pages.
Rydzy et al., "Stressed Permeability in Shales: Effects of Matrix Compressibility and Fractures—A Step Towards Measuring Matrix Permeability in Fractured Shale Samples," SCA2016-027, presented at the International Symposium of the Society of Core Analysts held in Snowmass, Colorado, USA, Aug. 21-26, 2016, 12 pages.
Ryoo et al, "Water-in-Carbon Dioxide Microemulsions with Methylated Branched Hydrocarbon Surfactants," Industrial & Engineering Chemistry Research 2003, 42:25 (6348-6358), 11 pages.
Sagisaka et al, "A New Class of Amphiphiles Designed for Use in Water-in-Supercritical CO2 Microemulsions," Langmuir 2016, 32:47 (12413-12422), 44 pages.
Sagisaka et al, "Effect of Fluorocarbon and Hydrocarbon Chain Lengths In Hybrid Surfactants for Supercritical CO2," Langmuir 2015, 31:27 (7479-7487), 36 pages.
Sagisaka et al, "Nanostructures in Water-in-CO2 Microemulsions Stabilized by Double-Chain Fluorocarbon Solubilizers," Langmuir 2013, 29:25 (7618-7628), 11 pages.
Samuel et al., "A New Solids-Free Non-Damaging High Temperature Lost-Circulation Pill: Development and First Field Applications," SPE-81494-MS, Society of Petroleum Engineers (SPE), presented at the Middle East Oil Show, Bahrain, 9-12 Jun. 9-12, 2003, 12 pages.
Samuel et al., "Polymer-Free Fluid for Fracturing Applications," SPE-59478-PA, Society of Petroleum Engineers (SPE), SPE Drill & Compl 1999, 14:4 (240-246), 7 pages.
Samuel et al., "Polymer-Free Fluid for Hydraulic Fracturing," SPE-38622-MS, Society of Petroleum Engineers (SPE), presented at the SPE Annual Technical Conference and Exhibition, San Antonio, Texas, Oct. 5-8, 1997, 7 pages.
Samuel et al., "Viscoelastic Surfactant Fracturing Fluids: Application in Low Permeability Reservoirs," SPE-60322-MS, Society of Petroleum Engineers (SPE), presented at the SPE Rocky Mountain Regional/Low-Permeability Reservoirs Symposium and Exhibition, Denver, 12-15 Mar. 12-15, 2000, 7 pages.
Santarelli et al., "Drilling through Highly Fractured Formations: A Problem, a Model, and a Cure," Society of Petroleum Engineers (SPE), presented at the 67th Annual Technical Conference and Exhibition of the Society of Petroleum Engineers, Washington D.C., Oct. 4-7, 1992, 10 pages.
Sayed and Al-Muntasheri, "A Safer Generation of Wettability Alteration Chemical Treatments," SPE-184566-MS, Society of Petroleum Engineers (SPE), presented at the SPE International Conference on Oilfield Chemistry, Apr. 3-5, 2017, 25 pages.
Schubert et al., "The Microstructure and Rheology of Mixed Cationic/Anionic Wormlike Micelles," Langmuir 2003, 19:10 (4079-4089), 11 pages.
Selvin et al., "Principles and biophysical applications of lanthanide-based probes," Annual Review of Biophysics and Biomolecular Structure, Jun. 2002, 31:275-302, 28 pages.
Semmelbeck et al., "Novel CO2-Emulsified Viscoelastic Surfactant Fracturing Fluid System Enables Commercial Production from Bypassed Pay in the Olmos Formation of South Texas," SPE-100524-MS, Society of Petroleum Engineers (SPE), presented at the SPE Gas Technology Symposium, Calgary, May 15-17, 2006, 8 pages.
Sepulveda et al., "Oil-Based Foam and Proper Underbalanced-Drilling Practices Improve Drilling Efficiency in a Deep Gulf Coast Well," SPE 115536, Society of Petroleum Engineers (SPE), presented at the 2008 SPE Annual Technical Conference and Exhibition in Denver, Colorado, Sep. 21-24, 2008, 8 pages.
Serra, "No Pressure Transient Analysis Methods for Naturally Fractured Reservoirs," (includes associated papers 12940 and 13014), Journal of Petroleum Technology, Dec. 1983, 35:12, Society of Petroleum Engineers, 18 pages.
Serres-Piole et al., "Water tracers in oilfield applications: Guidelines," Elsevier Ltd., Journal of Science and Engineering, Nov. 2012, 98-99:22-39, 18 pages.
Shafer et al., "Protocols for Calibrating NMR Log-Derived Permeabilities," International Symposium of the Society of Core Analysts, Aug. 21, 2005, 15 pages.
Shahid et al., "Natural-fracture reactivation in shale gas reservoir and resulting microseismicity," SPE 178437, Journal of Canadian Petroleum Technology, Nov. 2015, 54:06, 10 pages.
Shashkina et al., "Rheology of Viscoelastic Solutions of Cationic Surfactant. Effect of Added Associating Polymer," Langmuir 2005, 21:4 (1524-1530), 7 pages.
Shi et al., "Superhydrophobic silica aerogels reinforced with polyacrylonitrile fibers for adsorbing oil from water and oil mixtures," RSC Advances, Jan. 1, 2017, 7:7 (4039), 7 pages.
Shin et al., "Development and Testing of Microcompression for Post Irradiation Characterization of ODS Steels," Journal of Nuclear Materials, 2014, 444:43-48, 6 pages.
Shook et al., "Determining Reservoir Properties and Flood Performance from Tracer Test Analysis," SPE 124614, Society of Petroleum Engineers (SPE), presented at SPE Annual Technical Conference and Exhibition, Oct. 4-7, 2009, 19 pages.
Shukla et al., "Nanoindentation Studies on Shales," ARMA 13-578, American Rock Mechanics Association (ARMA), presented at the 47th US Rock Mechanics/Geomechanics Symposium, Jun. 23-26, 2013, 10 pages.
Siddig et al., "A review of different approaches for water-based drilling fluid filter cake removal," Journal of Petroleum Science and Engineering, Apr. 2020.
Sierra et al., "Woodford Shale Mechanical Properties and the Impacts of Lithofacies," ARMA 10-461, American Rock Mechanics Association (ARMA), presented at the 44th US Rock Mechanics Symposium and 5th US-Canada Rock Mechanics Symposium, Jun. 27-30, 2010, 10 pages.
Singh et al., "Facies classification based on seismic waveform," presented at the 5th Conference & Exposition on Petroleum Geophysics, Jan. 15-17, 2004, 456-462, 7 pages.
Siskin et al., "Reactivity of organic compounds in hot water: geochemical and technological implications," Science, Oct. 11, 1991, 254, 8 pages.
Slatt et al., "Merging Sequence Stratigraphy and Geomechanics for Unconventional Gas Shales," The Leading Edge, Special Section: Shales, Mar. 2011, 8 pages.
Slatt et al., "Outcrop/Behind Outcrop (Quarry), Multiscale Characterization of the Woodford Gas Shale," in Breyer, Shale Reservoirs—Giant Resources for the 21st Century: AAPG Memoir, 2011, 97: 1-21, 22 pages.
Sone et al., "Mechanical Properties of Shale-Gas Reservoir Rocks—Part 2: Ductile Creep, Brittle Strength, and Their Relation to the Elastic Modulus," Geophysics, Sep.-Oct. 2013, 78:5 (D393-D402), 10 pages.
Sone et al., "Mechanical Properties of Shale-Gas Reservoir Rocks—Part 1: Static and Dynamic Elastic Properties and Anisotropy," Geophysics, Sep.-Oct. 2013, 78:5 (D381-D392), 13 pages.
Song et al., "SERS-Encoded Nanogapped Plasmonic Nanoparticles: Growth of Metallic Nanoshell by Templating Redox-Active Polymer Brushes," Journal of the American Chemical Society (JACS), Apr. 28, 2014, 136: 6838-6841, 4 pages.
Soni, "LPG-Based Fracturing: An Alternative Fracturing Technique in Shale Reservoirs," IADC/SPE-170542-MS, Society of Petroleum Engineers (SPE), IADC/SPE Asia Pacific Drilling Technology Conference, Aug. 25-27, 2014, 7 pages.
Stewart et al., "Use of a Solids-Free Viscous Carrying Fluid in Fracturing Applications: An Economic and Productivity Comparison in Shallow Completions," SPE-30114-MS, Society of Petro-

(56) References Cited

OTHER PUBLICATIONS leum Engineers (SPE), presented at the SPE European Formation Damage Control Conference, Hague, The Netherlands, May 15-16, 1994, 14 pages.
Stiles et al., "Surface-enhanced Raman Spectroscopy," Annual Review of Analytical Chemistry, Mar. 18, 2008, 1:601-26, 29 pages.
Sullivan et al., "Optimization of a Viscoelastic Surfactant (VES) Fracturing Fluid for Application in High-Permeability Formations," SPE-98338-MS, Society of Petroleum Engineers (SPE), presented at the SPE International Symposium and Exhibition on Formation Damage Control, Lafayette, Louisiana, Feb. 15-17, 2006, 8 pages.
Tabatabaei et al., "Well performance diagnosis with temperature profile measurements," SPE 147448, Society of Petroleum Engineers (SPE), in SPE Annual Technical Conference and Exhibition, Oct. 30-Nov. 2, 2011, published Jan. 2011, 16 pages.
Taheri et al., "Investigation of rock salt layer creep and its effects on casing collapse," International Journal of Mining Science and Technology, 2020, 9 pages.
Tang, et al., "Impact of Stress-Dependent Matrix and Fracture Properties on Shale Gas Production," Energies, Jul. 2017, 10(7):996.
Tarokh et al., "Scaling of the fracture process zone in rock." International Journal of Fracture 204.2, Nov. 2016, 191-204, 14 pages.
Tathed et al., "Hydrocarbon saturation in Bakken Petroleum System based on joint inversion of resistivity and dielectric dispersion logs," Fuel, Dec. 2018, 233: 45-55, 11 pages.
Taylor et al., "Laboratory Evaluation of In-Situ Gelled Acids for Carbonate Reservoirs," SPE-71694-MS, Society of Petroleum Engineers (SPE), presented at the SPE Annual Technical Conference and Exhibition, New Orleans, Sep. 30-Oct. 3, 2001, 10 pages.
Thomas et al., "Fractured reservoir simulation," SPE-9305-PA, Society of Petroleum Engineers (SPE), SPE Journal, 23:1, Feb. 1983, 13 pages.
Tian et al., "Off-Resonant Gold Superstructures as Ultrabright Minimally Invasive Surface-Enhanced Raman Scattering (SERS) Probes," American Chemical Society (ACS), Chemistry of Materials (CM), Jul. 2015, 27: 5678-5684, 7 pages.
Timur, "Effective Porosity and Permeability of Sandstones Investigated Through Nuclear Magnetic Resonance Principles," Society of Petrophysicists and Well-Log Analysts, presented at the SPWLA 9th Annual Logging Symposium, Jun. 23-26, 1968, 18 pages.
Tinsley and Williams, "A new method for providing increased fracture conductivity and improving stimulation results," Journal of Petroleum Technology, vol. 27, Issue 11, pp. 1317-1325, SPE-4676-PA, 1975, 7 pages.
Tran et al., "The effects of filter-cake buildup and time-dependent properties on the stability of inclined wellbores," SPE Journal, Aug. 2011, 16(04):1010-1028.
Tranggono "Wellbore Collapse Failure Criteria and Drilling Optimization," University of Stavanger, 2019, pp. 1-132, 143 pages.
Trimmer et al., "Effect of pressure and stress on the water transport in intact and fractured gabbro and granite," Journal of Geophysical Research, vol. 85, Dec. 10, 1980, 13 pages.
Trippetta et al., "The seismic signature of heavy oil on carbonate reservoir through laboratory experiments and AVA modelling," Journal of Petroleum Science and Engineering, 2019, 177: 849-860, 12 pages.
Ulboldi et al., "Rock strength measurement on cuttings as input data for optimizing drill bit selection," SPE 56441, Society of Petroleum Engineers (SPE), presented at the 1999 SPE Annual Technical Conference and Exhibition, Oct. 3-6, 1999, 9 pages.
Uleberg and Kleppe, "Dual Porosity, Dual Permeability Formulation for Fractured Reservoir Simulation," TPG4150, Reservoir Recovery Techniques, Combined Gas/Water Injection Subprogram, 1996, 12 pages.
Ulm et al., "Material Invariant Poromechanics Properties of Shales," 2005, 8 pages.
Ulm et al., "The Nanogranular Nature of Shale," Acta Geotechnica, Springer, Jun. 15, 2006, 1:2, 12 pages.

Van Poollen et al., "Hydraulic Fracturing—Fracture Flow Capacity vs Well Productivity," Petroleum Transactions AIME, Vo. 213, pp. 91-95, SPE-890-G, 1958, 5 pages.
Van Poollen, "Productivity vs Permeability Damage in Hydraulically Produced Fractures," presented at Drilling and Production Practice, New York, New York, paper 906-2-G, Jan. 1957, 8 pages.
Van Zanten et al., "Advanced Viscoelastic Surfactant Gels for High-Density Completion Brines," SPE-143844-MS, Society of Petroleum Engineers (SPE), presented at the SPE European Formation Damage Control Conference, Noordwijk, The Netherlands, Jun. 7-10, 2011, 7 pages.
Van Zanten, "Stabilizing Viscoelastic Surfactants in High-Density Brines," SPE-141447-PA, Society of Petroleum Engineers (SPE), SPE Drill & Compl 26:4 (499-505), 7 pages.
Vanlandingham, "Review of Instrumented Indentation," Journal of Research of the National Institute of Standards and Technology, Jul.-Aug. 2003, 108:4 (249-265), 17 pages.
Verhoeven et al., "Modelling Laser Induced Melting," Mathematical and Computer Modelling, vol. 37, Issue 3-4, 2003, 19 pages.
Vernik et al., "Ultrasonic Velocity and Anisotropy of Hydrocarbon Source Rocks," Geophysics, May 1992, 57:5 (727-735), 9 pages.
Vincent, "Examining our Assumptions—Have oversimplifications jeopardized our ability to design optimal fracture treatments," presented at the SPE Hydraulic Fracturing Technology Conference, The Woodlands, SPE-119143-MS, Jan. 19-21, 2009, 51 pages.
Vincent, "Five Things you Didn't Want to Know about Hydraulic Fractures, presented at the International Conference for Effective and Sustainable Hydraulic Fracturing," an ASRM specialized Conference, Australia, ISRM-ICHF-2013-045, May 20-22, 2013, 14 pages.
Voltolini et al., "Anisotropy of Experimentally Compressd Kaolinite-illite-quartz Mixtures," Geophysics, Jan.-Feb. 2009, 74:1 (D13-D23), 11 pages.
Walters et al., "Kinetic rheology of hydraulic fracturing fluids," SPE 71660, Society of Petroleum Engineers (SPE), SPE Annual Technical Conference and Exhibition, Sep. 30-Oct. 3, 2001, 12 pages.
Wang and Samuel, "Geomechanical Modelling of Wellbore Stability in Salt Formations, 3D Geomechanical Modeling of Salt-Creep Behavior on Wellbore Casing for Presalt Reservoirs," SPE Drilling and Completion, 31(04): 261-272, Sep. 2013, 13 pages.
Wang et al., "A Feasibility Analysis on Shale Gas Exploitation with Supercritical Carbon Dioxide," Energy Sources, Part A: Recovery, Utilization, and Environmental Effects 2012, 34:15 (1426-1435), 11 pages.
Wang et al., "A New Viscoelastic Surfactant for High Temperature Carbonate Acidizing," SPE-160884-MS, Society of Petroleum Engineers (SPE), presented at the SPE Saudi Arabia Section Technical Symposium and Exhibition, Al-Khobar, Saudi Arabia, Apr. 8-11, 2012, 18 pages.
Wang et al., "A Numerical Study of Factors Affecting the Characterization of Nanoindentation on Silicon," Materials Science and Engineering: A, Feb. 25, 2007, 447:1 (244-253), 10 pages.
Wang et al., "Iron Sulfide Scale Dissolvers: How Effective Are They?" SPE 168063, Society of Petroleum Engineers (SPE), presented at the SPE Saudi Arabia Section Annual Technical Symposium and Exhibition, May 19-22, 2013, 22 pages.
Wang et al., "The Flattened Brazilian Disc Specimen Used for Testing Elastic Modulus, Tensile Strength and Fracture Toughness of Brittle Rocks: Analytical and Numerical Results," International Journal of Rock Mechanics and Mining Sciences, 2004, 41:2 (245-253), 9 pages.
Wang et al., "Ultralow Electrical Percolation in Graphene Aerogel/Epoxy Composites," Chemistry of Materials, Sep. 7, 2016, 28:18 (6731-6741), 11 pages.
Warpinski, "Understanding Hydraulic Fracture Growth, Effectiveness, and Safety Through Microseismic Monitoring," Chapter 6, in Effective and Sustainable Hydraulic Fracturing, Intech, May 17, 2013, 14 pages.
Warren and Root, "The Behavior of Naturally Fractured Reservoirs," SPE 426, Society of Petroleum Engineers (SPE), SPE Journal, Sep. 1963, 3:3 (245-255), 11 pages.
Waters, "Frac Fluids on Organic Shales: What We Know, What We Don't, and What Can We Do About It," Society of Petroleum

(56) References Cited

OTHER PUBLICATIONS

Engineers (SPE) Asia Pacific Hydraulic Fracturing Conference, Aug. 24-26, 2016, Beijing, China, 29 pages.
Wegst et al., "Bioinspired Structural Materials," Nature Materials, Jan. 2015, 14, 14 pages.
Weijermars et al., "Closure of open wellbores in creeping salt sheets" Geophysical Journal International, 196: 279-290, 2014, 12 pages.
Welton et al., "Anionic Surfactant Gel Treatment Fluid," SPE-105815-MS, Society of Petroleum Engineers (SPE), presented at the SPE International Symposium on Oilfield Chemistry, Houston, Feb. 28-Mar. 2, 2007, 8 pages.
Wenk et al., "Preferred Orientation and Elastic Anisotropy of Illite-Rich Shale," Geophysics, Mar.-Apr. 2007, 72:2 (E69-E75), 7 pages.
Wessels et al., "Identifying fault activation during hydraulic stimulation in the Barnett shale: source mechanisms, b values, and energy release analyses of microseismicity," presented at the SEG San Antonio 2011 Annual Meeting, Sep. 18-23, 2011, 5 pages.
Wikipedia.org [online], "Viscometer," created on Mar. 2002, [retrieved on Aug. 30, 2021], retrieved from : URL <https://en.wikipedia.org/wiki/Viscometer>, 12 pages.
Williams et al., "Acidizing Fundamentals," Society of Petroleum Engineers of AIME, Jan. 1979, 131 pages.
Wilson and Aifantis, "On the Theory of Consolidation with Double Porosity," International Journal of Engineering Science, 1982, 20:9 (1009-1035), 27 pages.
Wilson et al., "Fracture Testing of Bulk Silicon Microcantilever Beams Subjected to a Side Load," Journal of Microelectromechanical Systems, Sep. 1996, 5:3, 9 pages.
Witten et al., "Structured Fluids: Polymers, Colloids, Surfactants," New York: Oxford University Press, 2010, 231 pages.
Wu et al., "A reusable biosensor chip for SERS-fluorescence dual mode immunoassay," Proc. SPIE 9543:954317-1, Third International Symposium on Laser Interaction with Matter, LIMIS 2014, May 4, 2015, 6 pages.
Wu et al., "A SERS-Assisted 3D Barcode Chip for High-Throughput Biosensing," Nano Micro Small Journal, Jun. 11, 2015, 11:23 (2798-2806), 9 pages.
Wu et al., "Extraction of kerogen from oil shale with supercritical carbon dioxide: Molecular dynamics simulations," the Journal of Supercritical Fluids, 107: 499-506, Jan. 2016, 8 pages.
Wurster et al., "Characterization of the fracture toughness of microsized tungsten single crystal notched specimens," Philosophical Magazine, May 2012, 92:14 (1803-1825), 23 pages.
Wurzenberger et al., "Nitrogen-Rich Copper(II) Bromate Complexes: an Exotic Class of Primary Explosives," Journal of Inorganic Chemistry, 2018, 57: 7940-7949, 10 pages.
Xu et al., "Anisotropic elasticity of jarosite: A high-P synchrotron XRD study," American Mineralogist, 2010, 95:1 (19-23), 5 pages.
Xu et al., "Study on the nnesostructure and nnesonnechanical characteristics of the soil-rock mixture using digital image processing based finite element method," 2008, International Journal of Rock Mechanics and Mining Sciences, 749-762, 15 pages.
Xu et al., "Measurement of two-photon excitation cross sections of molecular fluorophores with data from 690 to 1050 nm," Journal of the Optical Society of America B, Mar. 1996, 13:3, 11 pages.
Yaich et al., "A Case Study: The Impact of Soaking on Well Performance in the Marcellus," SPE-178614-MS, URTeC: 2154766, Society of Petroleum Engineers (SPE), Unconventional Resources Technology Conference (URTeC), presented at the Unconventional Resources Technology Conference, Jul. 20-22, 2015, 11 pages.
Yamada and Jones, "A review of pulse technique for permeability measurements," SPE Journal, 20:5, Oct. 1980, 2 pages.
Yan et al., "General multi-porosity simulation for fractured reservoir modeling," Journal of Natural Gas Science Engineering, 33, Jul. 2016, 16 pages.
Yang et al., "Nanoscale geochemical and geomechanical characterization of organic matter in shale," Nature Communications, Dec. 19, 2017, 8:2179, 9 pages.
Yang et al., "Viscoelastic Evaluation of Gemini Surfactant Gel for Hydraulic Fracturing," SPE-165177-MS, Society of Petroleum Engineers (SPE), presented at the SPE European Formation Damage Conference and Exhibition, Noordwijk, The Netherlands, Jun. 5-7, 2013, 5 pages.
Yoldas, "Alumina gels that form porous transparent Al2O2," Journal of Materials Science, 1975, 10: 1856-1860, 5 pages.
Yu et al., "Impact of Hydrolysis at High Temperatures on the Apparent Viscosity of Carboxybetaine Viscoelastic Surfactant-Based Acid: Experimental and Molecular Dynamics Simulation Studies," SPE-142264-PA, Society of Petroleum Engineers (SPE), SPE J. 2012, 17:4 (1119-1130), 12 pages.
Yu et al., "Propagation and Retention of Viscoelastic Surfactants Following Matrix-Acidizing Treatments in Carbonate Cores," SPE-128047-PA, Society of Petroleum Engineers (SPE), SPE J. 2011, 16:4 (993-1001), 9 pages.
Zamberi et al., "Improved Reservoir Surveillance Through Injected Tracers In A Saudi Arabian Field: Case Study," SPE 166005, Society of Petroleum Engineers (SPE), presented at SPE Reservoir Characterization and Simulation Conference and Exhibition, Sep. 16-18, 2013, 15 pages.
Zeilinger et al., "Improved Prediction of Foam Diversion in Matrix Acidizing," SPE-29529-MS, Society of Petroleum Engineers (SPE), presented at the Production Symposium, Oklahoma City, Oklahoma, Apr. 2-4, 1995, 13 pages.
Zemel, "Chapter 3: Interwell Water Tracers," Tracers in the Oil Field, 43:1, Elsevier Science, Jan. 13, 1995, 47 pages.
Zeszotarski et al., "Imaging and Mechanical Property Measurements of Kerogen via Nanoindentation," Geochimica et Cosmochimica Acta, Oct. 15, 2004, 68:20 (4113-4119), 7 pages.
Zhang et al., "Matrix permeability measurement from fractured unconventional source-rock samples: Method and application," J Contam Hydrol, 2020, 233:103663.
Zhao et al., "A New Fracturing Fluid for HP/HT Applications," SPE-174204-MS, Society of Petroleum Engineers (SPE), presented at the SPE European Formation Damage Conference and Exhibition, Budapest, Hungary, Jun. 3-5, 2015, 17 pages.
Zheng et al., "Relationships between permeability, porosity and effective stress for low-permeability sedimentary rock," International Journal of Rock Mechanics and Mining Sciences, 2015, 78:304-318.
Zhou et al., "Upconversion luminescent materials: advances and applications," American Chemical Society (ACS), Chemical Reviews, Jan. 14, 2015, 115: 395-465, 71 pages.
Zielinska, "Swelling of EPDM rubbers for oil-well applications as influenced by medium composition and temperature," pecznienie uszczelnien z EPDM, Elastomery, Jan. 2016, 2:20, 12 pages.
Zielinski et al, "A Small-Angle Neutron Scattering Study of Water in Carbon Dioxide Microemulsions," Langmuir 1997, 13:15 (3934-3937), 4 pages.
Zimmerman and Bodvarsson, "Hydraulic Conductivity of Rock Fractures," transport in Porous Media, Jan. 1996, 23: 1-30, 31 pages.
Zoback, "Reservoir geomechanics," Cambridge University Press, 2010, Chapter 6: 196-197, 13 pages.
Zuo et al., "Polymer/Carbon-Based Hybrid Aerogels: Preparation, Properties and Applications," Materials, Oct. 9, 2015, 8:10 (6806-6848), 43 pages.

\* cited by examiner

400

500

INDENTATION METHOD TO MEASURE MULTIPLE ROCK PROPERTIES

TECHNICAL FIELD

The present disclosure is directed to measuring geomechanical properties of rock samples.

BACKGROUND

Mechanical properties are required inputs for any geomechanics analysis in the engineering activities in both the ground surface and underground environments, such as various operations in the life cycle of hydrocarbon exploration and production. For instance, accurate information of rock stiffness, for example, Young's modulus, is required to reliably predict the reservoir compaction and ground subsidence. In the drilling of a wellbore, the cohesive strength and frictional angle are necessary mechanical properties in the evaluation of the borehole breakout risk and safe mud weight design.

Common rock properties can be measured in a rock mechanics laboratories. For example, Young's modulus, Poisson's ration, cohesive strength, and frictional angle can be measured by performing uniaxial or triaxial compression tests. Tensile strength can be measured directly in direct tensile test, or a Brazilian test in which the tensile strength is determined by crushing a rock disk. Both compression and tensile tests require inch-sized cylindrical cores or discs. However, cores are often not available, especially for the overburden and seal rocks. On the other hand, small rock cuttings are circulated to the ground surface with mud in the drilling process. These cuttings carry the mineralogical and mechanical information of the original rocks from which they came.

SUMMARY

An embodiment described herein provides a method for performing an indentation test on a rock sample. The method includes measuring load and displacement versus time on an indentation measurement unit, while preforming a multistage indentation test. The multi-stage indentation test includes indenting a saturated specimen to full load to generate a line segment 1, releasing the load on the saturated specimen to generate a line segment 2, indenting the saturated specimen to full load to generate a line segment 3, holding the loading until the displacement curve levels off to generate a line segment 4, and reducing the loading to zero to generate a line segment 5.

DETAILED DESCRIPTION

A technique is disclosed herein to measure multiple mechanical properties of rocks from their core samples or cuttings by performing a multi-step indentation test on small rock pieces. More specifically, the method allows for the measuring of two elastic properties, undrained and drained stiffness, and one hydraulic property, diffusivity or diffusion coefficient, of rock sample using a single-stage indentation on a saturated rock sample. Undrained stiffness is a critical parameter in calculating short-time deformation of rock mass in response to stress changes. Likewise, drained stiffness determines long-time deformation of rock mass caused by stress changes. Diffusivity characterizes the time scale of fluid flow from transient flow to steady state flow over a given distance.

Figure 1:
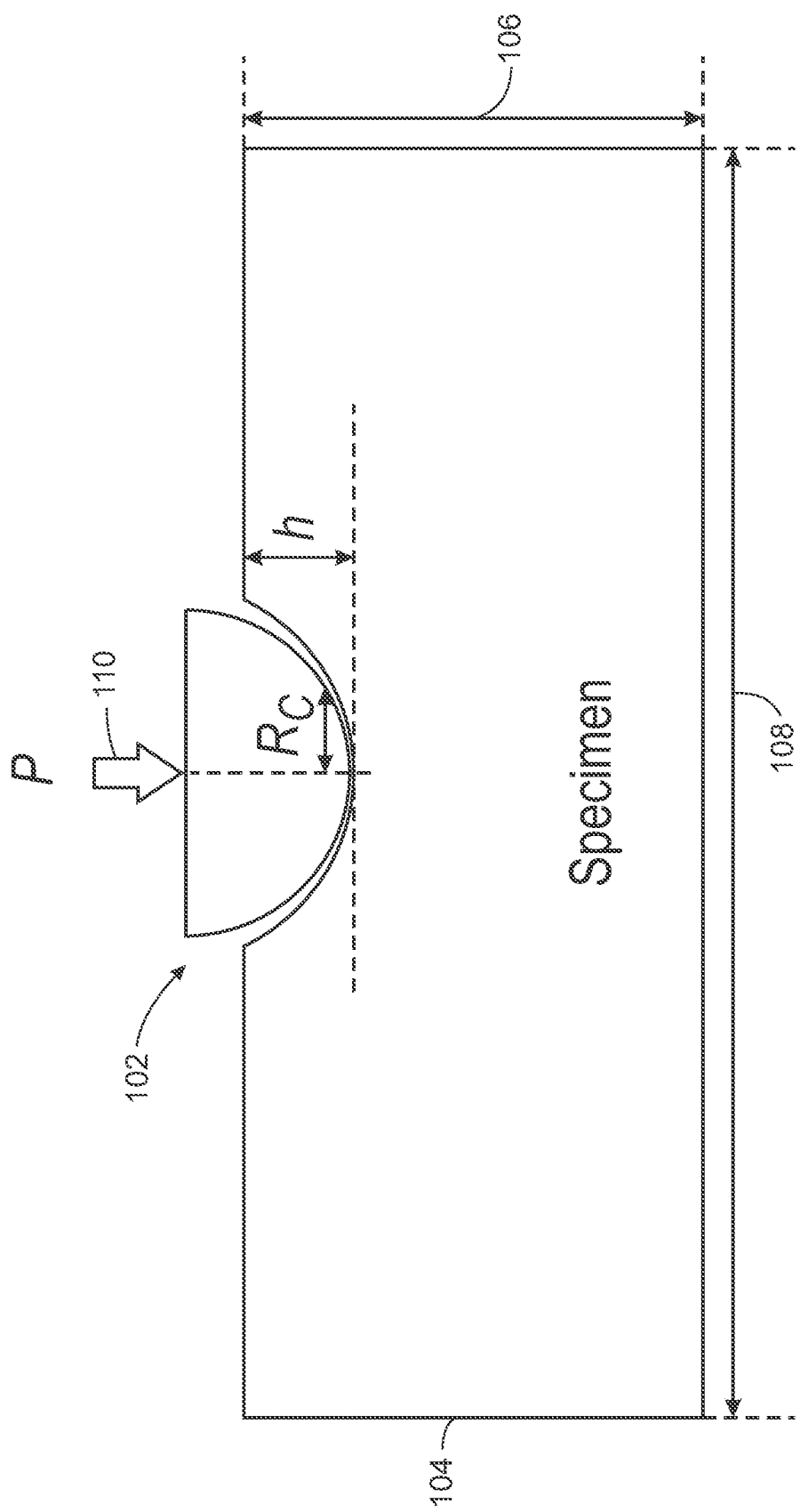
FIG. 1 is a schematic drawing of a nanoindentation test.

FIG. 1 is a schematic drawing of a nanoindentation test. In the indentation test, an indenter 102 is placed in contact with a specimen 104. In the embodiment shown, the indenter 102 has a hemispherical tip. However, any number of geometries may be used in the present techniques including a flat-tipped indenter, a cone tipped indenter, a Berkovich tipped indenter, a cubic corner tipped indenter, a Vickers indenter, or a Knoop tipped indenter.

In some embodiments, the specimen 104 is a rock sample collected during a well drilling process. For example, the specimen 104 may be collected from drilling cuttings, or a core sample, among others. In some embodiments, the specimen 104 is a rock sample collected at the surface, for example, over an oil sands field. The height (H) 106 and length (L) 108 of the specimen 104 are measured for use in the calculations described herein.

The indenter 102 is pushed into the specimen 104, or loaded, using pressure (P) 110 applied by the indentation measurement unit. In the loading process, both elastic and plastic deformation can take place, reflecting the elastoplastic response of the specimen. In the unloading process, the elastic deformation bounces back, or rebounds, so the stiffness can be extracted from unloading curve. Accordingly, after the pressure is released, the indentation has a height (h) that reflects the recovery after the elastic deformation has rebounded. After the rebound, the contact radius ($R_C$) can be used to determine the amount of the indenter 102 that is still in contact with the specimen 104.

Figure 2:
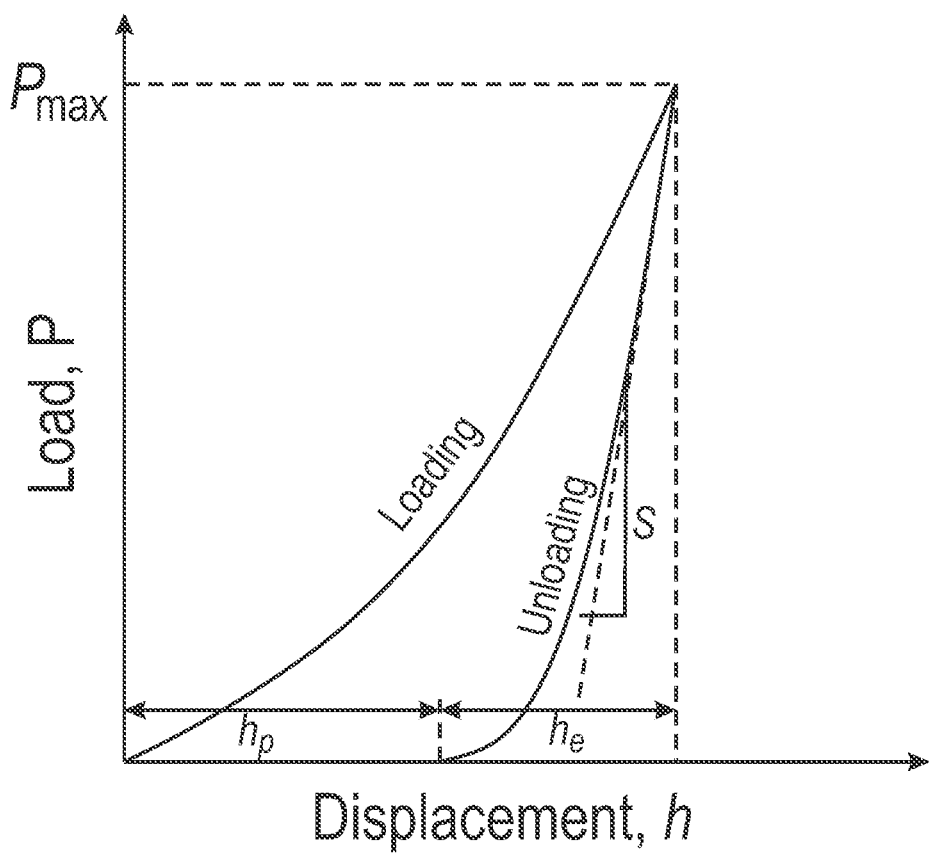
FIG. 2 is a of a load displacement curve for a single step nanoindentation test.

FIG. 2 is a 200 of a load displacement curve for a single step nanoindentation test. If the indentation does not introduce any plastic deformation, the deformation will fully recover after a complete unloading, the loading and unloading curves will overlap, and h, described with respect to FIG. 1, will be zero. In this case, the stiffness of the indented specimen is calculated using the formula of equation 1:

$$P = \frac{4}{3} E^* R^{\frac{1}{2}} h^{\frac{3}{2}} \tag{1}$$

In equation 1, P is the applied vertical load, R is the radius of the spherical indenter, and δ is the vertical displacement at the center of spherical indenter. E* is an intermediate variable determined by the stiffness parameters of the material of the indenter and sample, for example, using the formula of equation 2:

$$\frac{1}{E^*} = \frac{(1-v_s^2)}{E_s} + \frac{(1-v_p^2)}{E_p} \tag{2}$$

In equation 2, $E_s$ and $v_s$ are Young's modulus and Poisson's ratio of the indented material and $E_p$ and $v_p$ are Young's modulus and Poisson's ratio of the indenter.

If plastic deformation is induced, then only part of the deformation can be recovered after unloading. This is shown in the plot 200 of FIG. 2 as the plastic deformation term 'h$_p$', which indicates the amount of deformation that will not bounce back after the load is complete released. In this case, the stiffness can be calculated using the formula of equation 3:

$$H = \frac{P_{max}}{A_c} \quad (3)$$

In equation 3, the hardness (H) is defined as the ratio of the peak load (P$_{max}$) to the projected contact area (A$_c$=πR$_C^2$, R$_C$ is the contact radius, as shown in FIG. 1) at peak load. Then the stiffness, or reduced Young's modulus, can be calculated from the indenter geometry, and the slope of unloading curve and projected area at the peak load, using the formula of equation 4:

$$E^* = \frac{1}{\beta}\frac{\sqrt{\pi}}{2}\frac{S}{\sqrt{A_c}} \quad (4)$$

In equation 4, S is the slope of the unloading curve, and β is the geometry correction factor of the indentation tip. For example, β is 1 for spherical and cone tips, 1.034 for Berkovich and cubic corner tips, and 1.012 for Vickers and Knoop tips. Then, the stiffness of the indented material can be calculated using Eq. (2).

Figure 3:
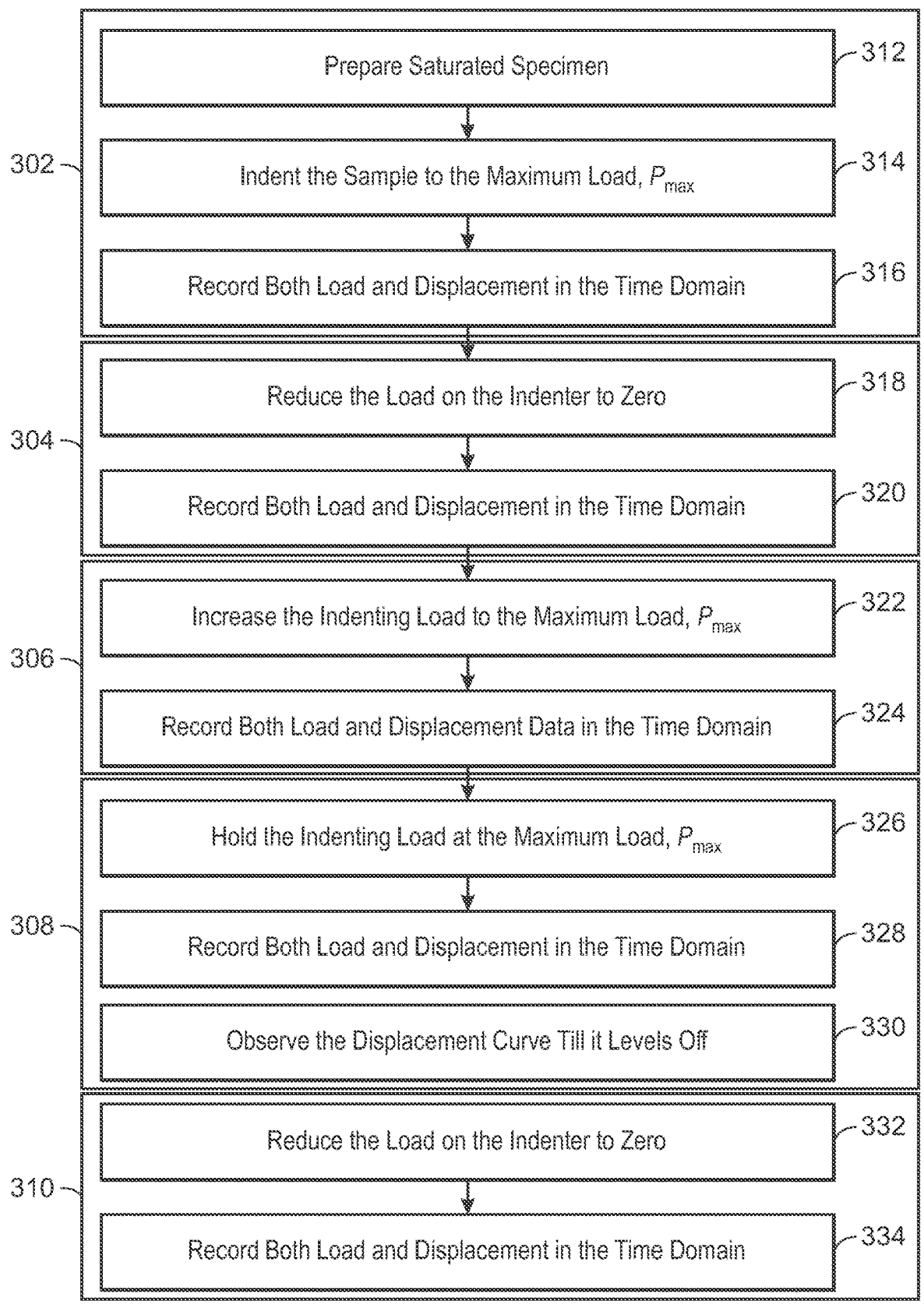
FIG. 3 is a process flow diagram of a method for performing a multistep nanoindentation test.
Figure 4:
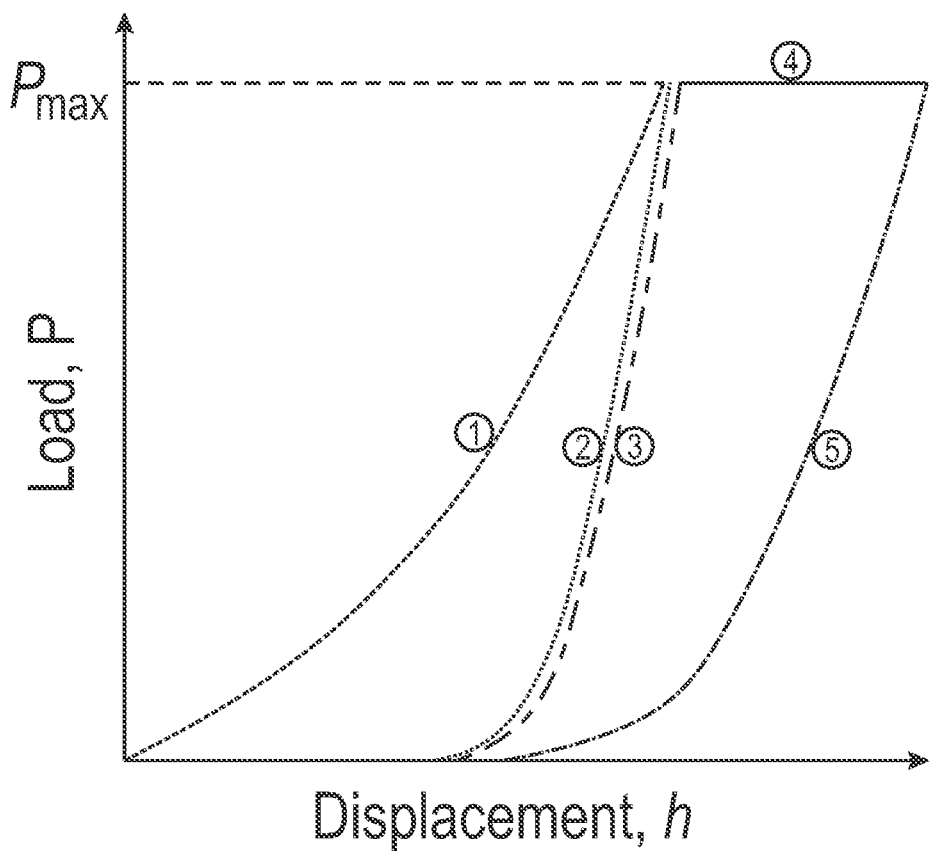
FIG. 4 is a plot of a load-displacement curve of a sample, generally illustrating the technique.
Figure 5:
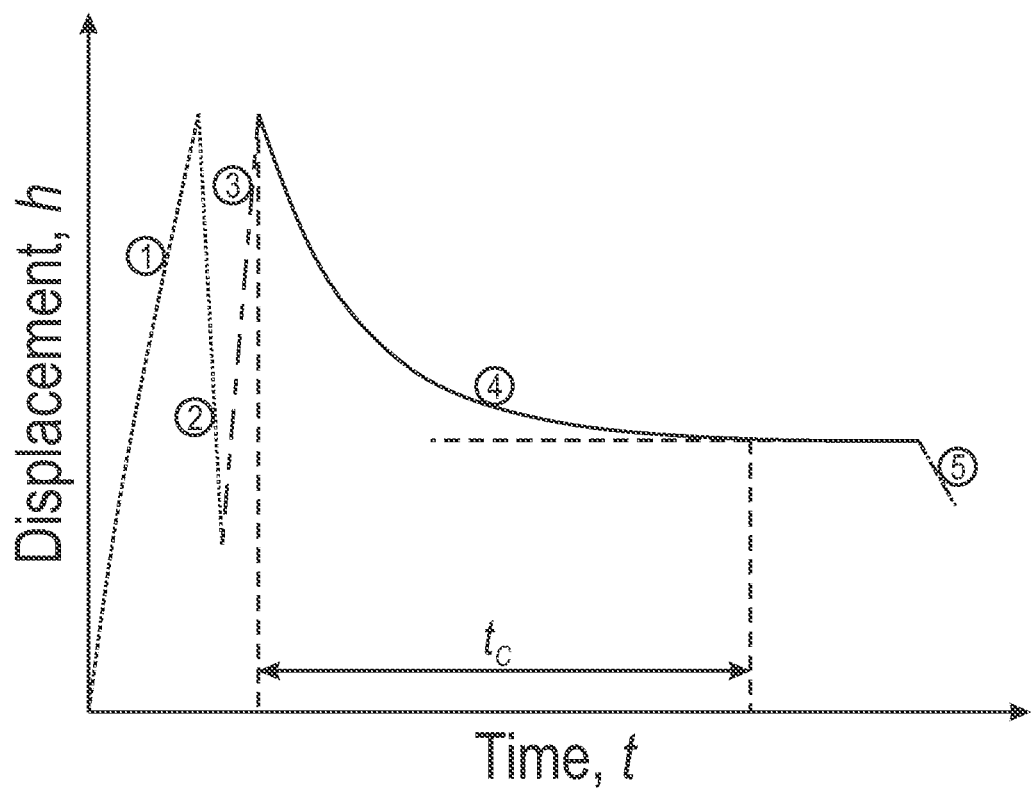
FIG. 5 is a plot of a displacement curve versus time of a sample that includes hydrocarbon fluids.

FIG. 3 is a process flow diagram of a method 300 for performing a multistep nanoindentation test. The multistep nanoindentation test can be used to measure three parameters, undrained stiffness, drained stiffness, and diffusivity. The method 300 is performed by measuring load and displacement over time on an indentation measurement unit during five testing stages. In the first stage 302, a saturated specimen is indented to full load generating a first line segment (1). As used herein, a saturated specimen includes the hydrocarbons still embedded in the rock, such as from a fresh drill cutting or core sample. In the second stage 304, the load is released on the saturated specimen, generating a second line segment (2). In the third stage 306, the saturated specimen is indented to full load, generating third line segment (3). In the fourth stage 308, the loading is held until the displacement curve has leveled off, generating a fourth line segment (4). In the fifth stage 310, the loading is reduced to zero, generating a fifth line segment (5). FIGS. 4 and 5 are plots that illustrate the data collected during the method 300 of FIG. 3. The five line segments, 1-5, are labeled in the plots of FIGS. 4 and 5.

In more detail, in the first stage 302, at block 312, the saturated specimen is prepared. This may be performed by collecting a fresh drill cutting proximate to the wellbore being drilled, or by cutting a sample out of a core sample, among others. As noted, the technique described may be used to determine hydrocarbons in oil sand fields. In these environments, the saturated specimen may be collected at ground level. At block 314, the saturated sample is indented to the maximum load, P$_{max}$, which is typically on the order of 100 mN in the indentation of rock materials. At block 316, the load and displacement are recorded in the time domain, generating line segment 1 of the plots of FIGS. 4 and 5.

In the second stage 304, at block 318, the load on the indenter is reduced to zero. At block 320, the load and displacement are recorded in the time domain, generating line segment 2 of the plots of FIGS. 4 and 5.

In the third stage 306, at block 322, the load on the indenter is increased to the maximum load, P$_{max}$. At block 324, the load and displacement are recorded in the time domain, generating line segment three of the plots of FIGS. 4 and 5.

In the fourth stage 308, at block 326, the indenting load is held at the maximum load, P$_{max}$. This allows the fluid in the specimen to fully dissipate. At block 328, load and displacement are recorded in the time domain, generating line segment 4 of the plots of FIGS. 4 and 5. At block 330, the displacement curve versus time is observed until it completely levels off, before proceeding to the fifth stage.

In the fifth stage 310, at block 332, the load on the indenter is reduced to zero. At block 334, the load and displacement are recorded in the time domain, generating line segment five of the plots of FIGS. 4 and 5.

FIG. 4 is a plot 400 of a load-displacement curve of a sample, generally illustrating the technique. Once the displacement curve is collected, it is post-processed to calculate the undrained stiffness, drained stiffness, and diffusivity. The undrained stiffness (E$_u$*) is computed from line segment 2 of FIG. 4. If no plastic deformation is present, this is performed from equation 4. If plastic deformation is present, equation 2 is used to compute the undrained stiffness (E$_u$*).

Similar to the undrained stiffness, the drained stiffness (E$_d$*) is computed from the slope of line segment 5 of FIG. 4. If no plastic deformation is present, this is performed from equation 4. If plastic deformation is present, equation 2 is used to compute the undrained stiffness (E$_d$*).

FIG. 5 is a plot 500 of a displacement curve versus time of a sample that includes hydrocarbon fluids. The plot 500 is used to calculate the diffusivity (c). This is performed by measuring the time (t$_c$) that line segment 4 of the displacement curve takes to level off after the application of maximum load. The diffusivity c can then be calculated from t$_c$ using the equation c=L$_c^2$/t$_c$, where $$L_c = \min\left\{\frac{H}{2}, \frac{L}{2}\right\},$$

H is the total height of the rock sample, and L is the total length of the rock sample, as discussed with respect to FIG. 1.

Embodiments

An embodiment described herein provides a method for performing an indentation test on a rock sample. The method includes measuring load and displacement versus time on an indentation measurement unit, while preforming a multi-stage indentation test. The multi-stage indentation test includes indenting a saturated specimen to full load to generate a line segment 1, releasing the load on the saturated specimen to generate a line segment 2, indenting the saturated specimen to full load to generate a line segment 3, holding the loading until the displacement curve levels off to generate a line segment 4, and reducing the loading to zero to generate a line segment 5.

In an aspect, the method includes computing undrained stiffness based, at least in part, on the line segment 2. In an aspect, the method includes computing the undrained stiffness (E$_u$*) for a sample that does not show plastic deformation using the equations:

$$P = \frac{4}{3}E_u^* R^{\frac{1}{2}} h^{\frac{3}{2}}$$

$$\frac{1}{E_u^*} = \frac{(1-v_s^2)}{E_s} + \frac{(1-v_p^2)}{E_p},$$

wherein $E_S$ is the Young's modulus of the indented material, $v_S$ is the Poisson's ratio of the indented material, $E_P$ is the Young's modulus of the indenter, and $v_P$ is the Poisson's ratio of the indenter. In an aspect, the method includes computing the undrained stiffness ($E_u^*$) for a sample that shows plastic deformation using the equations:

$$E_u^* = \frac{1}{\beta}\frac{\sqrt{\pi}}{2}\frac{S}{\sqrt{A_c}},$$

$$\frac{1}{E_u^*} = \frac{(1-v_s^2)}{E_s} + \frac{(1-v_p^2)}{E_p},$$

wherein S is the slope of the unloading curve; $\beta$ is the geometry correction factor of the indentation tip, and $A_c$ is the projected contact area calculated as $A_c = \pi R_C^2$, wherein $R_C$ is the contact radius at peak load.

In an aspect, the method includes draining a portion of the rock sample by holding the loading until the displacement versus time levels off.

In an aspect, the method includes computing drained stiffness ($E_d^*$) based, at least in part, on the line segment 5. In an aspect, the method includes computing the drained stiffness ($E_d^*$) for a sample that does not show plastic deformation using the equations (1) and (2):

$$P = \frac{4}{3}E_d^* R^{\frac{1}{2}} h^{\frac{3}{2}}$$

$$\frac{1}{E_d^*} = \frac{(1-v_s^2)}{E_s} + \frac{(1-v_p^2)}{E_p},$$

wherein $E_S$ is the Young's modulus of the indented material, $v_S$ is the Poisson's ratio of the indented material, $E_P$ is the Young's modulus of the indenter, and $v_P$ is the Poisson's ratio of the indenter. In an aspect, the method includes computing the drained stiffness ($E_d^*$) for a sample that shows plastic deformation using the equation:

$$E_d^* = \frac{1}{\beta}\frac{\sqrt{\pi}}{2}\frac{S}{\sqrt{A_c}},$$

$$\frac{1}{E_d^*} = \frac{(1-v_s^2)}{E_s} + \frac{(1-v_p^2)}{E_p},$$

wherein S is the slope of the unloading curve; $\beta$ is the geometry correction factor of the indentation tip, and $A_c$ is the projected contact area calculated as $A_c = \pi R_C^2$, wherein $R_C$ is the contact radius at peak load.

In an aspect, the method includes measuring time from loading to level-off of the displacement versus time ($t_c$) from line segment 4. In an aspect, the method includes calculating the diffusivity (c) by the equation $c = L_c^2/t_c$, where $$L_c = \min\left\{\frac{H}{2}, \frac{L}{2}\right\},$$

and H is the total height of the rock sample, and L is the total length of the rock sample.

In an aspect, the method includes indenting the rock sample with a hemispherical tipped indenter. In an aspect, the method includes indenting the rock sample with a flat-tipped indenter. In an aspect, the method includes indenting the rock sample with a cone tipped indenter. In an aspect, the method includes indenting the rock sample with a Berkovich, cubic corner, Vickers, or Knoop tipped indenter.

In an aspect, the method includes obtaining the rock sample from cuttings resulting from a wellbore drilling process. In an aspect, the method includes obtaining the rock sample from a core sample.

Other implementations are also within the scope of the following claims.

What is claimed is:

1. A method for performing an indentation test on a rock sample, comprising:
    measuring load and displacement versus time on an indentation measurement unit, while:
        indenting a saturated specimen to full load to generate a line segment 1;
        releasing the load on the saturated specimen to generate a line segment 2;
        indenting the saturated specimen to full load to generate a line segment 3;
        holding the loading until the displacement curve levels off to generate a line segment 4; and
        reducing the loading to zero to generate a line segment 5.

2. The method of claim 1, comprising computing undrained stiffness based, at least in part, on the line segment 2.

3. The method of claim 2, comprising computing the undrained stiffness ($E_u^*$) for a sample that does not show plastic deformation using the equations:

$$P = \frac{4}{3}E_u^* R^{\frac{1}{2}} h^{\frac{3}{2}}$$

$$\frac{1}{E_u^*} = \frac{(1-v_s^2)}{E_s} + \frac{(1-v_p^2)}{E_p},$$

wherein $E_S$ is the Young's modulus of the indented material, $v_S$ is the Poisson's ratio of the indented material, $E_P$ is the Young's modulus of the indenter, and $v_P$ is the Poisson's ratio of the indenter.

4. The method of claim 2, comprising computing the undrained stiffness ($E_u^*$) for a sample that shows plastic deformation using the equations:

$$E_u^* = \frac{1}{\beta}\frac{\sqrt{\pi}}{2}\frac{S}{\sqrt{A_c}},$$

$$\frac{1}{E_u^*} = \frac{(1-v_s^2)}{E_s} + \frac{(1-v_p^2)}{E_p},$$

wherein S is the slope of the unloading curve; $\beta$ is the geometry correction factor of the indentation tip, and $A_c$ is the projected contact area calculated as $A_c = \pi R_C^2$, wherein $R_C$ is contact radius at peak load.

5. The method of claim 1, comprising draining a portion of the rock sample by holding the loading until the displacement versus time levels off.

6. The method of claim 1, wherein comprising indenting the rock sample with a hemispherical tipped indenter.

7. The method of claim 1, comprising indenting the rock sample with a flat-tipped indenter.

8. The method of claim 1, comprising indenting the rock sample with a cone tipped indenter.

9. The method of claim 1, comprising indenting the rock sample with a Berkovich, cubic corner, Vickers, or Knoop tipped indenter.

10. The method of claim 1, comprising obtaining the rock sample from cuttings resulting from a wellbore drilling process.

11. The method of claim 1, obtaining the rock sample from a core sample.

12. A method for performing an indentation test on a rock sample, comprising:
measuring load and displacement versus time on an indentation measurement unit, while:
indenting a saturated specimen to full load to generate a line segment 1;
releasing the load on the saturated specimen to generate a line segment 2;
indenting the saturated specimen to full load to generate a line segment 3;
holding the loading until the displacement curve levels off to generate a line segment 4;
reducing the loading to zero to generate a line segment 5;
computing drained stiffness ($E_d^*$) based, at least in part, on the line segment 5; and
computing the drained stiffness ($E_d^*$) for a sample that does not show plastic deformation using the equations:

$$P = \frac{4}{3} E_d^* R^{\frac{1}{2}} h^{\frac{3}{2}}$$

$$\frac{1}{E_d^*} = \frac{(1 - v_s^2)}{E_s} + \frac{(1 - v_p^2)}{E_p},$$

wherein $E_S$ is the Young's modulus of the indented material, $v_S$ is the Poisson's ratio of the indented material, $E_P$ is the Young's modulus of the indenter, and $v_P$ is the Poisson's ratio of the indenter.

13. The method of claim 12, comprising computing the drained stiffness ($E_d^*$) for a sample that shows plastic deformation using the equation:

$$E_d^* = \frac{1}{\beta} \frac{\sqrt{\pi}}{2} \frac{S}{\sqrt{A_c}},$$

$$\frac{1}{E_d^*} = \frac{(1 - v_s^2)}{E_s} + \frac{(1 - v_p^2)}{E_p},$$

wherein S is the slope of the unloading curve; β is the geometry correction factor of the indentation tip, and $A_c$ is the projected contact area calculated as $A_c = \pi R_C^2$, wherein $R_C$ is the contact radius at peak load.

14. A method for performing an indentation test on a rock sample, comprising:
measuring load and displacement versus time on an indentation measurement unit, while:
indenting a saturated specimen to full load to generate a line segment 1;
releasing the load on the saturated specimen to generate a line segment 2;
indenting the saturated specimen to full load to generate a line segment 3;
holding the loading until the displacement curve levels off to generate a line segment 4;
reducing the loading to zero to generate a line segment 5;
measuring time from loading to level-off of the displacement versus time ($t_c$) from line segment 4; and
calculating the diffusivity (c) by the equation $c = L_c^2 / t_c$, where $$L_c = \min\left\{\frac{H}{2}, \frac{L}{2}\right\},$$

and H is the total height of the rock sample, and L is the total length of the rock sample.

* * * * *